United States Patent
Gomelsky et al.

(10) Patent No.: US 10,383,338 B2
(45) Date of Patent: Aug. 20, 2019

(54) COMPOSITIONS AND METHODS FOR MAKING AND USING HYDROLYTIC ENZYMES FOR DEGRADING POLYSACCHARIDES MADE BY FOODBORNE PATHOGENIC BACTERIA

(71) Applicant: University of Wyoming, Laramie, WY (US)

(72) Inventors: Mark Gomelsky, Laramie, WY (US); Kurt Miller, Laramie, WY (US); Volkan Köseoğlu, Charlottesville, VA (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 15/522,949

(22) PCT Filed: Oct. 29, 2015

(86) PCT No.: PCT/US2015/058038
§ 371 (c)(1),
(2) Date: Apr. 28, 2017

(87) PCT Pub. No.: WO2016/069888
PCT Pub. Date: May 6, 2016

(65) Prior Publication Data
US 2017/0332643 A1    Nov. 23, 2017

Related U.S. Application Data

(60) Provisional application No. 62/072,358, filed on Oct. 29, 2014.

(51) Int. Cl.
| | | |
|---|---|---|
| *A01N 63/00* | (2006.01) | |
| *A23L 33/10* | (2016.01) | |
| *C11D 3/386* | (2006.01) | |
| *C12P 19/02* | (2006.01) | |
| *B09C 1/10* | (2006.01) | |

(52) U.S. Cl.
CPC .............. *A01N 63/00* (2013.01); *A23L 33/10* (2016.08); *C11D 3/38636* (2013.01); *C12P 19/02* (2013.01); *C12Y 302/01* (2013.01); *A23V 2002/00* (2013.01); *B09C 1/10* (2013.01)

(58) Field of Classification Search
None
See application file for complete search history.

(56) References Cited

U.S. PATENT DOCUMENTS

| | | | |
|---|---|---|---|
| 2006/0078901 A1* | 4/2006 | Buchrieser | C07K 14/195 435/6.11 |
| 2010/0028378 A1 | 2/2010 | Lau et al. | |
| 2013/0143955 A1 | 6/2013 | Breaker et al. | |
| 2013/0295070 A1 | 11/2013 | Grallert et al. | |
| 2015/0157036 A1 | 6/2015 | Marcus-Johnson et al. | |
| 2015/0165016 A1 | 6/2015 | Pier et al. | |

FOREIGN PATENT DOCUMENTS

WO    WO2001/077335    * 10/2001

OTHER PUBLICATIONS

Pearson, An Introduction to Sequence Similarity ("Homology") Searching, Curr Protoc Bioinformatics, Jun. 2013, p. 1-9.*
Chen et al., "Cyclic di-GMP-Dependent Signaling Pathways in the Pathogenic Firmicute Listeria monocytogenes", PLoS Pathogens, Aug. 2014, vol. 10, No. 8, pp. 1-15.
Koseoglu et al., "Listeria monocytogenes exopolysaccharide: origin, structure, biosynthetic machinery and c-di-GMP-dependent regulation", Molecular Microbiology, Mar. 2015, vol. 96, No. 4, pp. 728-743.
Larsen, "Researchers Find Substance that Aids Listeria Growth", Food Poisoning Bulletin, Aug. 2014, Web Article, p. 1.
PCT International Search Report and the Written Opinion, Application No. PCT/US2015/058038, dated Jan. 29, 2016.
Simoes et al., "A review of current and emergent biofilm control strategies", LWT—Food Science and Technology, 2010, vol. 43, pp. 573-583.
UniProtKB—Q8Y5Z0, Web Article Retrieved on Jan. 13, 2016, http://www.uniprot.org/uniprot/Q8Y5Z0, Mar. 1, 2002, pp. 1-6.
UniProtKB—U6BHN2, Web Article Retrieved on Jan. 13, 2016, http://www.uniprot.org/uniprot/U6BHN2, Jan. 22, 2014, pp. 1-4.
UniProtKB—A0AK18 Web Article Retrieved on Jan. 13, 2016, http://www.uniprot.org/uniprot/A0AK18, Nov. 28, 2006, pp. 1-6.
UniProtKB—E3YRK5 Web Article Retrieved on Jan. 13, 2016, http://www.uniprot.org/uniprot/E3YRK5, Feb. 8, 2011, pp. 1-4.
UniProtKB—D6XZP1 Web Article Retrieved on Jan. 13, 2016, http://www.uniprot.org/uniprot/D6XZP1, Aug. 10, 2010, pp. 1-5.
UniProtKB—O31486, Web Article Retrieved on Jan. 13, 2016, http://www.uniprot.org/uniprot/O31486, Jan. 1, 1998, pp. 1-7.

* cited by examiner

*Primary Examiner* — Jennifer M. H. Tichy
(74) *Attorney, Agent, or Firm* — MacMillan, Sobanski & Todd, LLC

(57) ABSTRACT

Compositions and uses involving *L. monocytogenes* PssZ, as well as homologs, variants, and fragments thereof, are described.

Figure 1:
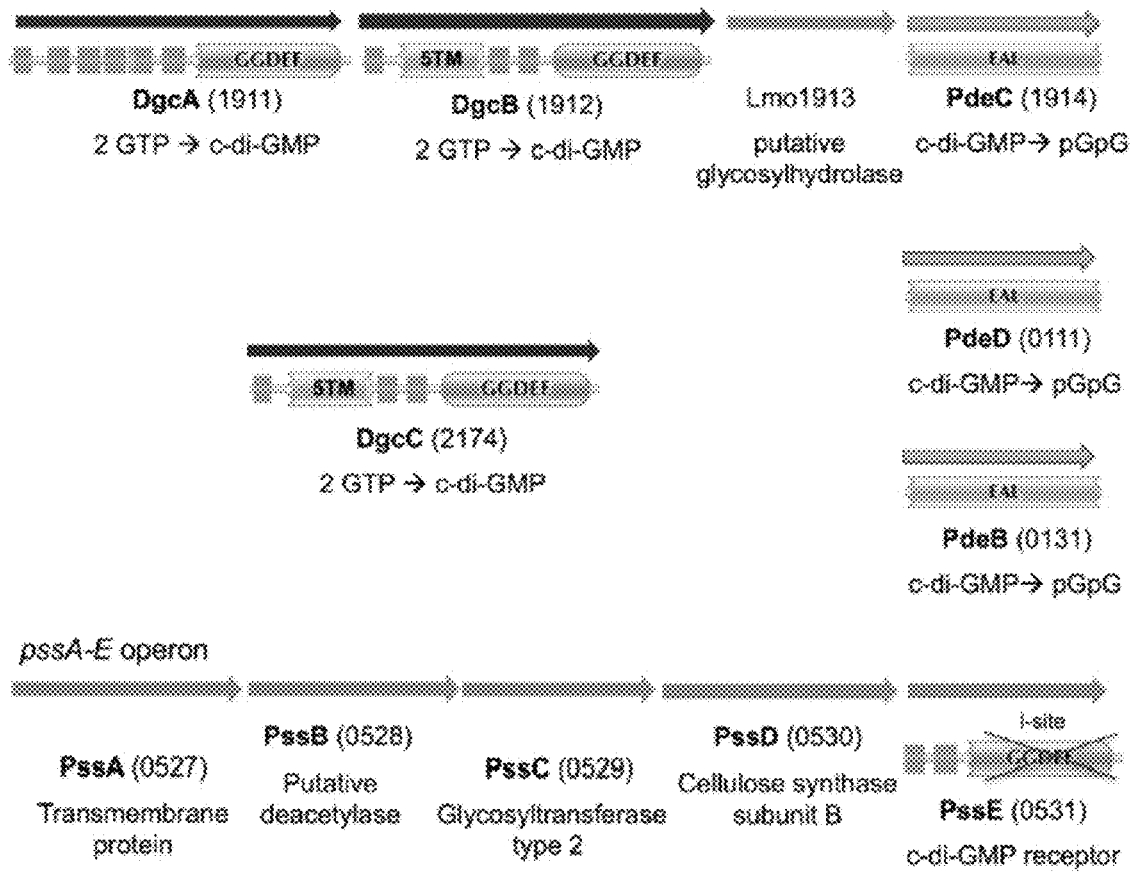

18 Claims, 35 Drawing Sheets
(19 of 35 Drawing Sheet(s) Filed in Color)
Specification includes a Sequence Listing.

```
#HMM     kskylktdgrvidtangnkdtvs.EGqgYgMllavaaadraaFdnLykwtkanlsstnek
#MATCH   k +y++++g +id  n+++ +     E  g  M   v ++d + F++   + + +   t+++
#PP      899**************9999755999*99*********************9999.99**
#Lin     KENYMTKNGLIIDYKNAQEPHYLAESIGLYMEYLVEVNDSKTFQEQVATLQKHFI-TTDN
#Lmo     KENYTAKNGLIMDYKNTEEPHYLAESIGLYMEYLVEVNDSKTFQKQVNHLEKYFI-AEDN

#HMM     LmaWrvnkskknkvedknsAtDGDlliAysLllAgkqwgsgrynylkeakniiiaiknv
#MATCH    + W  +s  + +           D  i  +L +A k+w  + y++l + +    ++++
#PP      ****998876654444......5***************99999998877665555543
#Lin     FIKWEATDSTTTNAIV-------DDFRITEALYQASKKWDHQAYQTLADTLISNTKKYSA
#Lmo     FIKWEATDSTTTNAIV-------DDFRITEALYQASEKFSFPSYKKMADKFLTNTKKYSA
```

FIG. 17B

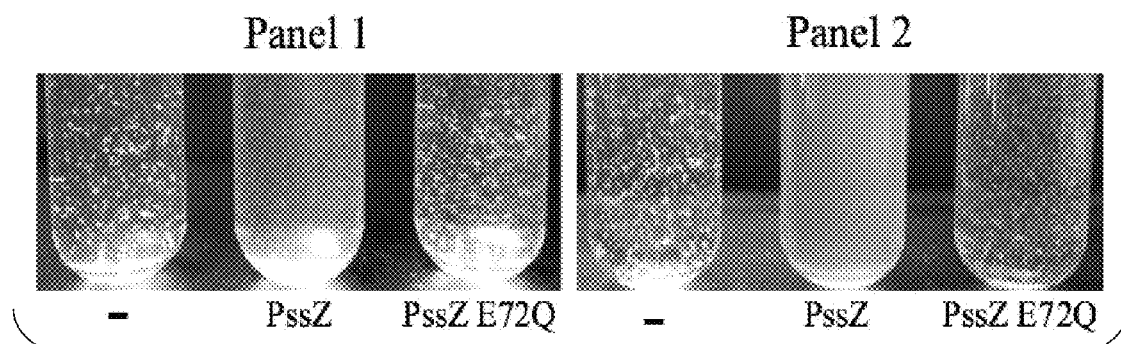

FIG. 17C

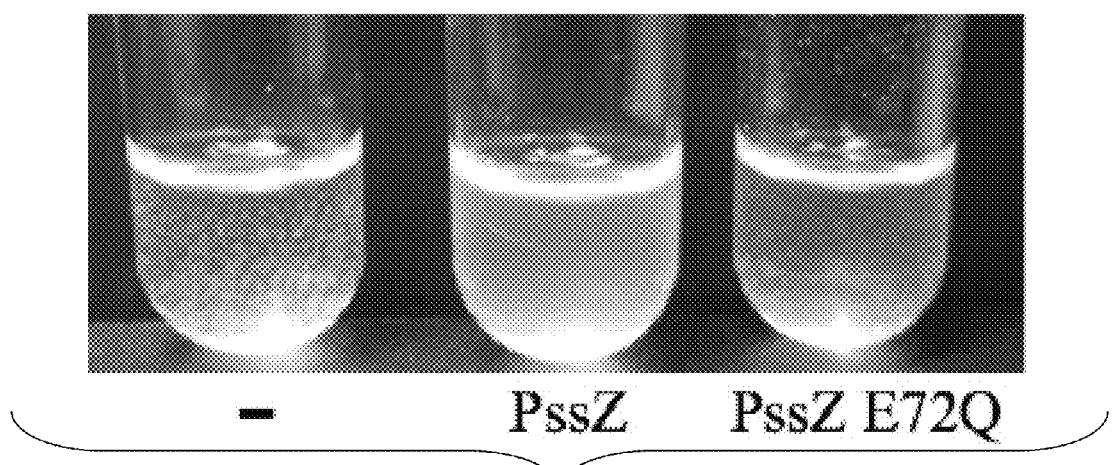

FIG. 17D

SEQUENCE LISTING

```
<160> NUMBER OF SEQ ID NOS: 64

<210> SEQ ID NO 1
<211> LENGTH: 334
<212> TYPE: PRT
<213> ORGANISM: Listeria monocytogenes
```

<400> SEQUENCE: 1

```
Met Lys Arg Phe Ile Leu Ile Leu Ile Leu Ile Phe Ile Gly Ala
1               5                   10                  15

Gly Phe Phe Ile Phe Leu Arg Pro Glu Ser Lys Lys Thr Val Ser Ala
                20                  25                  30

Pro Lys Glu Thr Thr Pro Thr Ser Thr Ser Val Gln Thr Tyr Val Lys
            35                  40                  45

Glu Asn Tyr Thr Ala Lys Asn Gly Leu Ile Met Asp Tyr Lys Asn Thr
50                  55                  60

Glu Glu Pro His Tyr Leu Ala Glu Ser Ile Gly Leu Tyr Met Glu Tyr
65                  70                  75                  80

Leu Val Glu Val Asn Asp Ser Lys Thr Phe Gln Lys Gln Val Asn His
                85                  90                  95

Leu Glu Lys Tyr Phe Ile Ala Glu Asp Asn Phe Ile Lys Trp Glu Ala
            100                 105                 110

Thr Asp Ser Thr Thr Thr Asn Ala Ile Val Asp Asp Phe Arg Ile Thr
        115                 120                 125

Glu Ala Leu Tyr Gln Ala Ser Glu Lys Phe Ser Phe Pro Ser Tyr Lys
130                 135                 140

Lys Met Ala Asp Lys Phe Leu Thr Asn Thr Lys Lys Tyr Ser Ala Glu
145                 150                 155                 160

Gln Gly Val Pro Val Asp Phe Tyr Asp Phe Val His Lys Lys Lys Ala
                165                 170                 175

Asp Thr Leu His Leu Ser Tyr Leu Asn Ile Gln Ala Met Gln Gln Ile
            180                 185                 190

Asn Tyr Arg Asp Lys Ala Tyr Leu Pro Ile Gln Thr Ile Asn Ala Asp
        195                 200                 205

Pro Phe Phe Thr Glu Val Phe Gln Asn Gly Gln Phe Lys Phe Ala Asp
210                 215                 220

Gln Lys Glu Val Asn Met Ile Asp Gln Met Leu Ile Ala Ile Ala Tyr
225                 230                 235                 240

Tyr Asp Glu Asn Gly Asp Ile Glu Pro Asn Phe Asp Asn Phe Leu Gln
                245                 250                 255

Thr Glu Leu Ala Ser Lys Gly Lys Ile Tyr Ala Arg Tyr Gln Arg Glu
            260                 265                 270

Thr Lys Lys Pro Ser Ser Glu Asn Glu Ser Thr Ala Val Tyr Ala Phe
        275                 280                 285

Leu Thr Gln Tyr Phe Asn Lys Thr Asn Gln Ala Lys Asn Gly Lys Ile
290                 295                 300

Thr Lys Glu Leu Leu Glu Lys Met Asp Thr Ser Asn Pro Glu Thr Thr
305                 310                 315                 320

His Phe Phe Asp Tyr Ile Asn Lys Glu Ile Thr Leu Lys Lys
                325                 330
```

<210> SEQ ID NO 2
<211> LENGTH: 312
<212> TYPE: PRT
<213> ORGANISM: Listeria monocytogenes

<400> SEQUENCE: 2

```
Arg Pro Glu Ser Lys Lys Thr Val Ser Ala Pro Lys Glu Thr Thr Pro
1               5                   10                  15

Thr Ser Thr Ser Val Gln Thr Tyr Val Lys Glu Asn Tyr Thr Ala Lys
                20                  25                  30
```

-continued

Asn Gly Leu Ile Met Asp Tyr Lys Asn Thr Glu Glu Pro His Tyr Leu
            35                  40                  45

Ala Glu Ser Ile Gly Leu Tyr Met Glu Tyr Leu Val Glu Val Asn Asp
 50                  55                  60

Ser Lys Thr Phe Gln Lys Gln Val Asn His Leu Glu Lys Tyr Phe Ile
65                  70                  75                  80

Ala Glu Asp Asn Phe Ile Lys Trp Glu Ala Thr Asp Ser Thr Thr Thr
                85                  90                  95

Asn Ala Ile Val Asp Asp Phe Arg Ile Thr Glu Ala Leu Tyr Gln Ala
            100                 105                 110

Ser Glu Lys Phe Ser Phe Pro Ser Tyr Lys Met Ala Asp Lys Phe
        115                 120                 125

Leu Thr Asn Thr Lys Lys Tyr Ser Ala Glu Gln Gly Val Pro Val Asp
        130                 135                 140

Phe Tyr Asp Phe Val His Lys Lys Ala Asp Thr Leu His Leu Ser
145                 150                 155                 160

Tyr Leu Asn Ile Gln Ala Met Gln Gln Ile Asn Tyr Arg Asp Lys Ala
                165                 170                 175

Tyr Leu Pro Ile Gln Thr Ile Asn Ala Asp Pro Phe Phe Thr Glu Val
            180                 185                 190

Phe Gln Asn Gly Gln Phe Lys Phe Ala Asp Gln Lys Glu Val Asn Met
        195                 200                 205

Ile Asp Gln Met Leu Ile Ala Ile Ala Tyr Tyr Asp Glu Asn Gly Asp
        210                 215                 220

Ile Glu Pro Asn Phe Asp Asn Phe Leu Gln Thr Glu Leu Ala Ser Lys
225                 230                 235                 240

Gly Lys Ile Tyr Ala Arg Tyr Gln Arg Glu Thr Lys Lys Pro Ser Ser
                245                 250                 255

Glu Asn Glu Ser Thr Ala Val Tyr Ala Phe Leu Thr Gln Tyr Phe Asn
            260                 265                 270

Lys Thr Asn Gln Ala Lys Asn Gly Lys Ile Thr Lys Glu Leu Leu Glu
        275                 280                 285

Lys Met Asp Thr Ser Asn Pro Glu Thr Thr His Phe Phe Asp Tyr Ile
290                 295                 300

Asn Lys Glu Ile Thr Leu Lys Lys
305                 310

<210> SEQ ID NO 3
<211> LENGTH: 5
<212> TYPE: PRT
<213> ORGANISM: Listeria monocytogenes

<400> SEQUENCE: 3

Gly Gly Asp Glu Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 5
<212> TYPE: PRT
<213> ORGANISM: Listeria monocytogenes
<220> FEATURE:
<221> NAME/KEY: MOD_RES
<222> LOCATION: (3)..(3)
<223> OTHER INFORMATION: Asp or Glu

<400> SEQUENCE: 5

Gly Gly Xaa Glu Phe
1               5

<210> SEQ ID NO 6
<211> LENGTH: 5
<212> TYPE: PRT
<213> ORGANISM: Listeria monocytogenes

<400> SEQUENCE: 6

Asp Lys Asp Asp Ala
1               5

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggctgcaga atttgttgta atttgtcgac a                                  31

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttacgcattc cgctcaccgg atttaacttt ccttatcat                          39

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtgagcgga atgcgtaa                                                 18

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggggatcca gaagcatctg taattgcttt                                    30

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggctgcaga aactttgaaa aggcgacag                              29

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atatttcttc atgtaaagcc gaatacttat aatcattttt ttacg            45

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggctttaca tgaagaaata t                                      21

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggggatccg cctgtaatat tatcggtatt                             30

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggctgcagt aggcgcgttc gctttga                                27

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctccggcga tatttacgca gccacattac agtaaattt                   39

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgtaaatatc gccggagc                                                 18

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggggatcct ttcgtgtttt cttcttgaag                                    30

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggctgcaga aagaaataaa tgattttcat gg                                 32

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttatttctta agagttattt ctttaattag gatgaatcgt ttcat                   45

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaagaaataa ctcttaagaa ataa                                          24

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggggtcgaca aagaaataaa tgattttcat gg                                 32

<210> SEQ ID NO 23

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatcacctgc agccgtcctg tatctccttc gagtg                                35

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcgaatatgt acttgcgcca tgctgttcca taatgaatca ag                        42

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tggaacagca tggcgcaagt acatattcgc gaaacagaac cag                       43

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcgatagaat tcgcagttac aaagaacagc aagaaatact cg                        42

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gatcacctgc agcctttgat gctgcattca accatg                               36

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctgatgaaca gcaatatttt ggaaccaatt agggcgatat tgtc                      44

<210> SEQ ID NO 29
<211> LENGTH: 37
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aattggttcc aaaatattgc tgttcatcag ggggaac                             37

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcgatagaat tctctgttgc attgcttgga tatttagata gc                       42

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atagatctgc agcggcatct ggaatggggc aacaaattgc                          40

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
taacgttcta gacaactgtt cgaccaaaaa gcatc                               35

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
attgcatcta gagtatgtat tgcagacgga aattagtctg                          40

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtcataggta cccttacctc gccagtttca agcactcg                            38

<210> SEQ ID NO 35
<211> LENGTH: 38
<212> TYPE: DNA
```

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
atcgatctgc aggaaattcg ctaaaattaa gttctagc         38

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gctctaggat ccccataatg aatcaagaat atttggc          37

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
cgagatggat ccgaactcga atgaaacgat tcatc            35

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
atctcggaat tctacggagg gcttttcat ttgtc             35

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gggccatggg gatgaaacga ttcatcctaa tt               32

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gggctgcagt tatttcttaa gagttatttc tttatt           36

<210> SEQ ID NO 41
<211> LENGTH: 32
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 41
gggccatggg gatgaaacga ttcatcctaa tt                                   32

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catataaagt ccaatgctct gggctagata gtggggttc                            39

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cagagcattg gactttatat g                                               21

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gggctgcagt tatttcttaa gagttatttc ttt                                  33

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggggctagcc gaccagagtc taaaaag                                         27

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gggaagcttt ttcttaagag ttatttcttt att                                  33

<210> SEQ ID NO 47
<211> LENGTH: 306
<212> TYPE: PRT
<213> ORGANISM: Exiguobacterium undae
```

<400> SEQUENCE: 47

Met Phe Met Thr Arg Gln Gln Asp Pro Val Ile Gln Gln Val Glu Thr
1               5                   10                  15

Val Tyr Met Lys Glu Gly Leu Ile Arg Ala Tyr Asp Arg Glu Glu Ala
            20                  25                  30

Gln Arg Leu Ser Glu Ser Leu Gly Gln Tyr Met Val Tyr Leu Leu Glu
        35                  40                  45

Ile Gly Asp Ala Asp Arg Phe Ala Glu Gln Val Asp Ile Leu Arg Lys
    50                  55                  60

Gln Phe Leu Val Thr Thr Glu Glu Gly Asp Phe Ile Lys Trp Glu Leu
65                  70                  75                  80

Thr Pro Lys Thr Ala Thr Asn Ala Ile Val Asp Asp Phe Arg Ile Ser
                85                  90                  95

Asn Ala Leu Phe Ala Ala Ala Lys Arg Phe Asp Glu Pro Asp Tyr Gln
            100                 105                 110

Gln Leu Ser Arg Arg Ile Asp Asp Gly Ile Val Glu His Met Lys Val
        115                 120                 125

Ser Gly Val Pro Ile Asp Phe Tyr Asp Trp Asn Leu Lys Met Gln Thr
    130                 135                 140

Asn Glu Leu Arg Leu Asn Tyr Leu Asp Ala Thr Ala Leu Lys Arg Leu
145                 150                 155                 160

Asn Leu Val Glu Pro Val Gln Glu Val Leu Gln Ala Ala Pro Arg Ser
                165                 170                 175

Gly Pro Phe Phe His Glu Ile Tyr Leu Pro Glu Asp Lys Arg Tyr Lys
            180                 185                 190

Thr Ala Asp Asp Lys Glu Val Asn Met Ile Asp Gln Ala Leu Ile Ala
        195                 200                 205

Ile Val Ser Glu Glu Leu Thr Gly Gln Gln Asp Glu Ala Phe Tyr Ala
    210                 215                 220

Phe Ile Asp Gln Glu Met Lys Lys Gly Lys Leu Tyr Ala Arg Tyr Asp
225                 230                 235                 240

Arg Ser Thr Ala Ser Pro Arg Ser Asp Asp Glu Ser Ser Val Tyr
                245                 250                 255

Ala Leu Leu Leu Pro Tyr Val Ser Glu Val Gln Arg Lys Met Thr
            260                 265                 270

Glu Arg Leu Asp Gln Ile Asp Leu Thr Asp Ala Ala Thr Thr His Val
        275                 280                 285

Phe Asp Tyr Leu Asn Glu Ala Ile Ala Arg Val Gln Thr Ser Met Pro
    290                 295                 300

Asn Lys
305

<210> SEQ ID NO 48
<211> LENGTH: 298
<212> TYPE: PRT
<213> ORGANISM: Listeria monocytogenes

<400> SEQUENCE: 48

Lys Glu Thr Thr Pro Thr Ser Thr Ser Val Gln Thr Tyr Val Lys Glu
1               5                   10                  15

Asn Tyr Thr Ala Lys Asn Gly Leu Ile Met Asp Tyr Lys Asn Thr Glu
            20                  25                  30

Glu Pro His Tyr Leu Ala Glu Ser Ile Gly Leu Tyr Met Glu Tyr Leu
        35                  40                  45

Val Glu Val Asn Asp Ser Lys Thr Phe Gln Lys Gln Val Asn His Leu
 50                  55                  60

Glu Lys Tyr Phe Ile Ala Glu Asp Asn Phe Ile Lys Trp Glu Ala Thr
 65                  70                  75                  80

Asp Ser Thr Thr Thr Asn Ala Ile Val Asp Asp Phe Arg Ile Thr Glu
                 85                  90                  95

Ala Leu Tyr Gln Ala Ser Glu Lys Phe Ser Phe Pro Ser Tyr Lys Lys
                100                 105                 110

Met Ala Asp Lys Phe Leu Thr Asn Thr Lys Lys Tyr Ser Ala Glu Gln
                115                 120                 125

Gly Val Pro Val Asp Phe Tyr Asp Phe Val His Lys Lys Lys Ala Asp
130                 135                 140

Thr Leu His Leu Ser Tyr Leu Asn Ile Gln Ala Met Gln Gln Ile Asn
145                 150                 155                 160

Tyr Arg Asp Lys Ala Tyr Leu Pro Ile Gln Thr Ile Asn Ala Asp Pro
                165                 170                 175

Phe Phe Thr Glu Val Phe Gln Asn Gly Gln Phe Lys Phe Ala Asp Gln
                180                 185                 190

Lys Glu Val Asn Met Ile Asp Gln Met Leu Ile Ala Ile Ala Tyr Tyr
                195                 200                 205

Asp Glu Asn Gly Asp Ile Glu Pro Asn Phe Asp Asn Phe Leu Gln Thr
210                 215                 220

Glu Leu Ala Ser Lys Gly Lys Ile Tyr Ala Arg Tyr Gln Arg Glu Thr
225                 230                 235                 240

Lys Lys Pro Ser Ser Glu Asn Glu Ser Thr Ala Val Tyr Ala Phe Leu
                245                 250                 255

Thr Gln Tyr Phe Asn Lys Thr Asn Gln Ala Lys Asn Gly Lys Ile Thr
                260                 265                 270

Lys Glu Leu Leu Glu Lys Met Asp Thr Ser Asn Pro Glu Thr Thr His
                275                 280                 285

Phe Phe Asp Tyr Ile Asn Lys Glu Ile Thr
                290                 295

<210> SEQ ID NO 49
<211> LENGTH: 293
<212> TYPE: PRT
<213> ORGANISM: Exiguobacterium undae

<400> SEQUENCE: 49

Arg Gln Gln Asp Pro Val Ile Gln Gln Val Glu Thr Val Tyr Met Lys
 1               5                  10                  15

Glu Gly Leu Ile Arg Ala Tyr Asp Arg Glu Glu Ala Gln Arg Leu Ser
                 20                  25                  30

Glu Ser Leu Gly Gln Tyr Met Val Tyr Leu Leu Glu Ile Gly Asp Ala
                 35                  40                  45

Asp Arg Phe Ala Glu Gln Val Asp Ile Leu Arg Lys Gln Phe Leu Val
 50                  55                  60

Thr Thr Glu Glu Gly Asp Phe Ile Lys Trp Glu Leu Thr Pro Lys Thr
 65                  70                  75                  80

Ala Thr Asn Ala Ile Val Asp Asp Phe Arg Ile Ser Asn Ala Leu Phe
                 85                  90                  95

Ala Ala Ala Lys Arg Phe Asp Glu Pro Asp Tyr Gln Gln Leu Ser Arg
                100                 105                 110

Arg Ile Asp Asp Gly Ile Val Glu His Met Lys Val Ser Gly Val Pro
                115                 120                 125

Ile Asp Phe Tyr Asp Trp Asn Leu Lys Met Gln Thr Asn Glu Leu Arg
            130                 135                 140

Leu Asn Tyr Leu Asp Ala Thr Ala Leu Lys Arg Leu Asn Leu Val Glu
145                 150                 155                 160

Pro Val Gln Glu Val Leu Gln Ala Ala Pro Arg Ser Gly Pro Phe Phe
                165                 170                 175

His Glu Ile Tyr Leu Pro Glu Asp Lys Arg Tyr Lys Thr Ala Asp Asp
            180                 185                 190

Lys Glu Val Asn Met Ile Asp Gln Ala Leu Ile Ala Ile Val Ser Glu
                195                 200                 205

Glu Leu Thr Gly Gln Gln Asp Glu Ala Phe Tyr Ala Phe Ile Asp Gln
            210                 215                 220

Glu Met Lys Lys Gly Lys Leu Tyr Ala Arg Tyr Asp Arg Ser Thr Ala
225                 230                 235                 240

Ser Pro Arg Ser Asp Asp Glu Ser Ser Val Tyr Ala Leu Leu Leu
                245                 250                 255

Pro Tyr Val Ser Glu Val Gln Arg Lys Met Thr Glu Arg Leu Asp
            260                 265                 270

Gln Ile Asp Leu Thr Asp Ala Ala Thr Thr His Val Phe Asp Tyr Leu
            275                 280                 285

Asn Glu Ala Ile Ala
            290

<210> SEQ ID NO 50
<211> LENGTH: 342
<212> TYPE: PRT
<213> ORGANISM: Carnobacterium mobile

<400> SEQUENCE: 50

Met Asn Lys Lys Arg Phe Tyr Leu Ile Leu Val Ile Leu Leu Ile
1               5                   10                  15

Ser Ser Leu Leu Ala Leu Ser Phe His Gln Lys Ile Gly Val Gln Glu
                20                  25                  30

Val Val Asn Asn Lys Tyr Glu Asn Asn Lys Gly Leu Ile Lys Asn Tyr
            35                  40                  45

Ala Lys Asn Gly Lys Val Gln Tyr Leu Ser Glu Ser Ile Gly Gln Tyr
    50                  55                  60

Leu Ser Tyr Leu Leu Leu Val Glu Asp Glu Lys Glu Phe Lys Gln Gln
65                  70                  75                  80

Val Ala Val Leu Lys Lys Asn Phe Leu Val Lys Gln Ala Asp Gly Thr
                85                  90                  95

Phe Ile Gln Trp Val Ala Thr Asn Gln Thr Thr Thr Asn Ala Ser Val
            100                 105                 110

Asp Asp Phe Arg Ile Ile Ala Val Leu Lys Lys Ala Ser Glu Gln Phe
        115                 120                 125

Gln Glu Pro Ala Tyr Gln Ile Leu Ala Asp Glu Leu Glu Glu Thr Leu
    130                 135                 140

Ile Ser Lys Gln Leu Thr Asp Gly Leu Ile Val Asp Phe Tyr Asp Trp
145                 150                 155                 160

Glu Leu Gln Lys Lys Ala Ala Val Leu His Leu Ser Tyr Ile Asp Asp
                165                 170                 175

Gln Ile Ile Lys Thr Asp Ser Lys Val Asn Lys Ala Lys Tyr Gln Lys
            180                 185                 190

Ile Leu Met Glu Ser Val Asp Ser Asp Thr Pro Phe Phe Lys Glu Val

```
                195                 200                 205
Tyr Thr Leu Glu Glu Gln Thr Tyr Gln Leu Ala Asp Lys Lys Ser Val
    210                 215                 220

Asn Leu Ile Asp Gln Leu Met Ile Ala Ile Gln Tyr Val Lys Leu Thr
225                 230                 235                 240

Asn Gln Thr Pro Ala Gln Phe Asp Gln Trp Leu Lys Ala Glu Trp Asp
                245                 250                 255

Ala Asn Gly Lys Phe Phe Gly Gly Tyr Leu Arg Thr Asp Leu Thr Pro
            260                 265                 270

Ala Val Pro Tyr Glu Ser Ser Ala Val Tyr Ala Leu Ala Thr Leu Tyr
        275                 280                 285

Phe Lys Leu Val His Glu Glu Ala Tyr Ala Glu Gln Leu His Gln Val
    290                 295                 300

Leu Leu Lys Gln Ser Pro Phe Asp Lys Asn Ala Asp Tyr Ala Thr Ile
305                 310                 315                 320

His Phe Phe Asp Tyr Met Trp Val Lys Thr Val Asp Val Leu Tyr Lys
                325                 330                 335

Lys Asp Leu Ile Asp Lys
            340

<210> SEQ ID NO 51
<211> LENGTH: 285
<212> TYPE: PRT
<213> ORGANISM: Listeria monocytogenes

<400> SEQUENCE: 51

Ser Val Gln Thr Tyr Val Lys Glu Asn Tyr Thr Ala Lys Asn Gly Leu
1               5                   10                  15

Ile Met Asp Tyr Lys Asn Thr Glu Glu Pro His Tyr Leu Ala Glu Ser
            20                  25                  30

Ile Gly Leu Tyr Met Glu Tyr Leu Val Glu Val Asn Asp Ser Lys Thr
        35                  40                  45

Phe Gln Lys Gln Val Asn His Leu Glu Lys Tyr Phe Ile Ala Glu Asp
    50                  55                  60

Asn Phe Ile Lys Trp Glu Ala Thr Asp Ser Thr Thr Asn Ala Ile
65                  70                  75                  80

Val Asp Asp Phe Arg Ile Thr Glu Ala Leu Tyr Gln Ala Ser Glu Lys
                85                  90                  95

Phe Ser Phe Pro Ser Tyr Lys Lys Met Ala Asp Lys Phe Leu Thr Asn
            100                 105                 110

Thr Lys Lys Tyr Ser Ala Glu Gln Gly Val Pro Val Asp Phe Tyr Asp
        115                 120                 125

Phe Val His Lys Lys Ala Asp Thr Leu His Leu Ser Tyr Leu Asn
    130                 135                 140

Ile Gln Ala Met Gln Gln Ile Asn Tyr Arg Asp Lys Ala Tyr Leu Pro
145                 150                 155                 160

Ile Gln Thr Ile Asn Ala Asp Pro Phe Phe Thr Glu Val Phe Gln Asn
                165                 170                 175

Gly Gln Phe Lys Phe Ala Asp Gln Lys Glu Val Asn Met Ile Asp Gln
            180                 185                 190

Met Leu Ile Ala Ile Ala Tyr Tyr Asp Glu Asn Gly Asp Ile Glu Pro
        195                 200                 205

Asn Phe Asp Asn Phe Leu Gln Thr Glu Leu Ala Ser Lys Gly Lys Ile
    210                 215                 220
```

Tyr Ala Arg Tyr Gln Arg Glu Thr Lys Lys Pro Ser Ser Glu Asn Glu
225                 230                 235                 240

Ser Thr Ala Val Tyr Ala Phe Leu Thr Gln Tyr Phe Asn Lys Thr Asn
            245                 250                 255

Gln Ala Lys Asn Gly Lys Ile Thr Lys Glu Leu Leu Glu Lys Met Asp
        260                 265                 270

Thr Ser Asn Pro Glu Thr Thr His Phe Phe Asp Tyr Ile
    275                 280                 285

<210> SEQ ID NO 52
<211> LENGTH: 298
<212> TYPE: PRT
<213> ORGANISM: Carnobacterium mobile

<400> SEQUENCE: 52

Gly Val Gln Glu Val Val Asn Asn Lys Tyr Glu Asn Asn Lys Gly Leu
1               5                   10                  15

Ile Lys Asn Tyr Ala Lys Asn Gly Lys Val Gln Tyr Leu Ser Glu Ser
            20                  25                  30

Ile Gly Gln Tyr Leu Ser Tyr Leu Leu Leu Val Glu Asp Glu Lys Glu
        35                  40                  45

Phe Lys Gln Gln Val Ala Val Leu Lys Lys Asn Phe Leu Val Lys Gln
    50                  55                  60

Ala Asp Gly Thr Phe Ile Gln Trp Val Ala Thr Asn Gln Thr Thr Thr
65                  70                  75                  80

Asn Ala Ser Val Asp Asp Phe Arg Ile Ile Ala Val Leu Lys Lys Ala
            85                  90                  95

Ser Glu Gln Phe Gln Glu Pro Ala Tyr Gln Ile Leu Ala Asp Glu Leu
        100                 105                 110

Glu Glu Thr Leu Ile Ser Lys Gln Leu Thr Asp Gly Leu Ile Val Asp
    115                 120                 125

Phe Tyr Asp Trp Glu Leu Gln Lys Lys Ala Ala Val Leu His Leu Ser
130                 135                 140

Tyr Ile Asp Asp Gln Ile Ile Lys Thr Asp Ser Lys Val Asn Lys Ala
145                 150                 155                 160

Lys Tyr Gln Lys Ile Leu Met Glu Ser Val Asp Ser Asp Thr Pro Phe
            165                 170                 175

Phe Lys Glu Val Tyr Thr Leu Glu Glu Gln Thr Tyr Gln Leu Ala Asp
        180                 185                 190

Lys Lys Ser Val Asn Leu Ile Asp Gln Leu Met Ile Ala Ile Gln Tyr
    195                 200                 205

Val Lys Leu Thr Asn Gln Thr Pro Ala Gln Phe Asp Gln Trp Leu Lys
210                 215                 220

Ala Glu Trp Asp Ala Asn Gly Lys Phe Phe Gly Gly Tyr Leu Arg Thr
225                 230                 235                 240

Asp Leu Thr Pro Ala Val Pro Tyr Glu Ser Ser Ala Val Tyr Ala Leu
            245                 250                 255

Ala Thr Leu Tyr Phe Lys Leu Val His Glu Glu Ala Tyr Ala Glu Gln
        260                 265                 270

Leu His Gln Val Leu Leu Lys Gln Ser Pro Phe Asp Lys Asn Ala Asp
    275                 280                 285

Tyr Ala Thr Ile His Phe Phe Asp Tyr Met
    290                 295

<210> SEQ ID NO 53

<211> LENGTH: 342
<212> TYPE: PRT
<213> ORGANISM: Carnobacterium jeotgali

<400> SEQUENCE: 53

| Met | Ser | Lys | Lys | Arg | Phe | Phe | Met | Ile | Leu | Leu | Val | Ile | Leu | Leu | Ile |
|---|---|---|---|---|---|---|---|---|---|---|---|---|---|---|---|
| 1 | | | | 5 | | | | | 10 | | | | | 15 | |

| Thr | Ile | Leu | Thr | Leu | Leu | Phe | Ser | Tyr | Asn | Lys | Arg | Glu | Val | Gln | Glu |
|---|---|---|---|---|---|---|---|---|---|---|---|---|---|---|---|
| | | | 20 | | | | | 25 | | | | | 30 | | |

| Val | Ile | Glu | Asn | Asn | Tyr | Lys | Asn | Asp | Asp | Asn | Leu | Ile | Lys | Asn | Tyr |
|---|---|---|---|---|---|---|---|---|---|---|---|---|---|---|---|
| | | | 35 | | | | | 40 | | | | | 45 | | |

| Ala | Lys | Asn | Asn | Gln | Ile | Glu | Tyr | Leu | Ser | Glu | Ser | Thr | Gly | Gln | Tyr |
|---|---|---|---|---|---|---|---|---|---|---|---|---|---|---|---|
| | 50 | | | | | 55 | | | | | 60 | | | | |

| Leu | Tyr | Tyr | Leu | Leu | Leu | Val | Lys | Asp | Glu | Lys | Glu | Phe | Lys | Gln | Gln |
|---|---|---|---|---|---|---|---|---|---|---|---|---|---|---|---|
| 65 | | | | | 70 | | | | | 75 | | | | | 80 |

| Val | Asp | Ser | Leu | Lys | Asn | Asn | Phe | Ile | Val | Lys | Arg | Ser | Asp | Gly | Thr |
|---|---|---|---|---|---|---|---|---|---|---|---|---|---|---|---|
| | | | | 85 | | | | | 90 | | | | | 95 | |

| Tyr | Ile | Lys | Trp | Thr | Thr | Ser | Asp | Gln | Thr | Thr | Thr | Asn | Ala | Ser | Val |
|---|---|---|---|---|---|---|---|---|---|---|---|---|---|---|---|
| | | | | 100 | | | | | 105 | | | | | 110 | |

| Asp | Asp | Phe | Arg | Ile | Ile | Glu | Val | Leu | Arg | Lys | Gly | Gly | Lys | Tyr | Phe |
|---|---|---|---|---|---|---|---|---|---|---|---|---|---|---|---|
| | | | 115 | | | | | 120 | | | | | 125 | | |

| Gln | Glu | Pro | Asp | Tyr | Val | Ile | Leu | Ala | Asn | Glu | Leu | Glu | Glu | Thr | Leu |
|---|---|---|---|---|---|---|---|---|---|---|---|---|---|---|---|
| | 130 | | | | | 135 | | | | | 140 | | | | |

| Asn | Ser | Lys | Gln | Leu | Thr | Asp | Gly | Leu | Ile | Val | Asp | Phe | Tyr | Asp | Trp |
|---|---|---|---|---|---|---|---|---|---|---|---|---|---|---|---|
| 145 | | | | | 150 | | | | | 155 | | | | | 160 |

| Glu | Leu | Gln | Lys | Lys | Ala | Thr | Thr | Val | His | Leu | Ser | Tyr | Ile | Asn | Asp |
|---|---|---|---|---|---|---|---|---|---|---|---|---|---|---|---|
| | | | | 165 | | | | | 170 | | | | | 175 | |

| Gln | Ile | Ile | Lys | Gly | Asn | Ala | Arg | Val | Asp | Pro | Ala | Asp | Tyr | Gln | Lys |
|---|---|---|---|---|---|---|---|---|---|---|---|---|---|---|---|
| | | | 180 | | | | | 185 | | | | | 190 | | |

| Leu | Leu | Ala | Gly | Ser | Thr | Asn | Ser | Gln | Asn | Pro | Phe | Phe | Lys | Glu | Ile |
|---|---|---|---|---|---|---|---|---|---|---|---|---|---|---|---|
| | | | 195 | | | | | 200 | | | | | 205 | | |

| Tyr | Thr | Val | Asp | Lys | His | Ser | Tyr | Leu | Ser | Ala | Asp | Lys | Asn | Thr | Val |
|---|---|---|---|---|---|---|---|---|---|---|---|---|---|---|---|
| | 210 | | | | | 215 | | | | | 220 | | | | |

| Asn | Met | Ile | Asp | Gln | Phe | Met | Ile | Ala | Ile | Gln | Tyr | Leu | Lys | Phe | Met |
|---|---|---|---|---|---|---|---|---|---|---|---|---|---|---|---|
| 225 | | | | | 230 | | | | | 235 | | | | | 240 |

| Asn | Gln | Val | Pro | Pro | Glu | Phe | Asp | Gln | Trp | Val | Lys | Gln | Glu | Trp | Asp |
|---|---|---|---|---|---|---|---|---|---|---|---|---|---|---|---|
| | | | | 245 | | | | | 250 | | | | | 255 | |

| Thr | Asn | Gly | Lys | Leu | Phe | Gly | Gly | Tyr | Val | Lys | Ser | Thr | Arg | Thr | Pro |
|---|---|---|---|---|---|---|---|---|---|---|---|---|---|---|---|
| | | | 260 | | | | | 265 | | | | | 270 | | |

| Ala | Val | Pro | Tyr | Glu | Ser | Ser | Val | Tyr | Ala | Leu | Ala | Tyr | Leu | Tyr |
|---|---|---|---|---|---|---|---|---|---|---|---|---|---|---|
| | | 275 | | | | | 280 | | | | | 285 | | |

| Phe | Lys | Gln | Ala | Asn | Glu | Glu | Lys | Tyr | Ala | Asp | Glu | Leu | Tyr | Ala | Met |
|---|---|---|---|---|---|---|---|---|---|---|---|---|---|---|---|
| | 290 | | | | | 295 | | | | | 300 | | | | |

| Ile | Leu | Thr | Gln | Pro | Ser | Phe | Asp | Lys | Asn | Pro | Asp | Tyr | Ser | Lys | Ile |
|---|---|---|---|---|---|---|---|---|---|---|---|---|---|---|---|
| 305 | | | | | 310 | | | | | 315 | | | | | 320 |

| His | Phe | Phe | Asp | Tyr | Ile | Trp | Ile | Glu | Thr | Ala | Asn | Ala | Ile | Tyr | Lys |
|---|---|---|---|---|---|---|---|---|---|---|---|---|---|---|---|
| | | | | 325 | | | | | 330 | | | | | 335 | |

| Thr | Arg | Asp | Lys | Thr | Gln |
|---|---|---|---|---|---|
| | | | 340 | | |

<210> SEQ ID NO 54
<211> LENGTH: 284
<212> TYPE: PRT
<213> ORGANISM: Listeria monocytogenes

<400> SEQUENCE: 54

Val Gln Thr Tyr Val Lys Glu Asn Tyr Thr Ala Lys Asn Gly Leu Ile
1               5                   10                  15

Met Asp Tyr Lys Asn Thr Glu Glu Pro His Tyr Leu Ala Glu Ser Ile
            20                  25                  30

Gly Leu Tyr Met Glu Tyr Leu Val Glu Val Asn Asp Ser Lys Thr Phe
        35                  40                  45

Gln Lys Gln Val Asn His Leu Glu Lys Tyr Phe Ile Ala Glu Asp Asn
    50                  55                  60

Phe Ile Lys Trp Glu Ala Thr Asp Ser Thr Thr Asn Ala Ile Val
65              70                  75                  80

Asp Asp Phe Arg Ile Thr Glu Ala Leu Tyr Gln Ala Ser Glu Lys Phe
                85                  90                  95

Ser Phe Pro Ser Tyr Lys Lys Met Ala Asp Lys Phe Leu Thr Asn Thr
            100                 105                 110

Lys Lys Tyr Ser Ala Glu Gln Gly Val Pro Val Asp Phe Tyr Asp Phe
        115                 120                 125

Val His Lys Lys Lys Ala Asp Thr Leu His Leu Ser Tyr Leu Asn Ile
    130                 135                 140

Gln Ala Met Gln Gln Ile Asn Tyr Arg Asp Lys Ala Tyr Leu Pro Ile
145                 150                 155                 160

Gln Thr Ile Asn Ala Asp Pro Phe Phe Thr Glu Val Phe Gln Asn Gly
                165                 170                 175

Gln Phe Lys Phe Ala Asp Gln Lys Glu Val Asn Met Ile Asp Gln Met
            180                 185                 190

Leu Ile Ala Ile Ala Tyr Tyr Asp Glu Asn Gly Asp Ile Glu Pro Asn
        195                 200                 205

Phe Asp Asn Phe Leu Gln Thr Glu Leu Ala Ser Lys Gly Lys Ile Tyr
    210                 215                 220

Ala Arg Tyr Gln Arg Glu Thr Lys Lys Pro Ser Ser Glu Asn Glu Ser
225                 230                 235                 240

Thr Ala Val Tyr Ala Phe Leu Thr Gln Tyr Phe Asn Lys Thr Asn Gln
                245                 250                 255

Ala Lys Asn Gly Lys Ile Thr Lys Glu Leu Leu Glu Lys Met Asp Thr
            260                 265                 270

Ser Asn Pro Glu Thr Thr His Phe Phe Asp Tyr Ile
        275                 280

<210> SEQ ID NO 55
<211> LENGTH: 297
<212> TYPE: PRT
<213> ORGANISM: Carnobacterium jeotgali

<400> SEQUENCE: 55

Val Gln Glu Val Ile Glu Asn Asn Tyr Lys Asn Asp Asp Asn Leu Ile
1               5                   10                  15

Lys Asn Tyr Ala Lys Asn Asn Gln Ile Glu Tyr Leu Ser Glu Ser Thr
            20                  25                  30

Gly Gln Tyr Leu Tyr Tyr Leu Leu Val Lys Asp Glu Lys Glu Phe
        35                  40                  45

Lys Gln Gln Val Asp Ser Leu Lys Asn Asn Phe Ile Val Lys Arg Ser
    50                  55                  60

Asp Gly Thr Tyr Ile Lys Trp Thr Thr Ser Asp Gln Thr Thr Thr Asn
65              70                  75                  80

Ala Ser Val Asp Asp Phe Arg Ile Ile Glu Val Leu Arg Lys Gly Gly

```
                    85                  90                  95
Lys Tyr Phe Gln Glu Pro Asp Tyr Val Ile Leu Ala Asn Glu Leu Glu
                100                 105                 110

Glu Thr Leu Asn Ser Lys Gln Leu Thr Asp Gly Leu Ile Val Asp Phe
            115                 120                 125

Tyr Asp Trp Glu Leu Gln Lys Lys Ala Thr Thr Val His Leu Ser Tyr
        130                 135                 140

Ile Asn Asp Gln Ile Ile Lys Gly Asn Ala Arg Val Asp Pro Ala Asp
145                 150                 155                 160

Tyr Gln Lys Leu Leu Ala Gly Ser Thr Asn Ser Gln Asn Pro Phe Phe
                165                 170                 175

Lys Glu Ile Tyr Thr Val Asp Lys His Ser Tyr Leu Ser Ala Asp Lys
            180                 185                 190

Asn Thr Val Asn Met Ile Asp Gln Phe Met Ile Ala Ile Gln Tyr Leu
        195                 200                 205

Lys Phe Met Asn Gln Val Pro Pro Glu Phe Asp Gln Trp Val Lys Gln
    210                 215                 220

Glu Trp Asp Thr Asn Gly Lys Leu Phe Gly Gly Tyr Val Lys Ser Thr
225                 230                 235                 240

Arg Thr Pro Ala Val Pro Tyr Glu Ser Ser Ala Val Tyr Ala Leu Ala
                245                 250                 255

Tyr Leu Tyr Phe Lys Gln Ala Asn Glu Glu Lys Tyr Ala Asp Glu Leu
            260                 265                 270

Tyr Ala Met Ile Leu Thr Gln Pro Ser Phe Asp Lys Asn Pro Asp Tyr
        275                 280                 285

Ser Lys Ile His Phe Phe Asp Tyr Ile
    290                 295

<210> SEQ ID NO 56
<211> LENGTH: 304
<212> TYPE: PRT
<213> ORGANISM: Jeotgalibacillus campisalis

<400> SEQUENCE: 56

Met Phe Ser Thr Asp Pro Thr Leu Gln Val Val Lys Glu Gln Tyr Thr
1               5                   10                  15

Asn Gln Glu Gly Leu Ile His Ala Tyr Pro Leu Gln Gln Asp Ser Glu
                20                  25                  30

Tyr Leu Ser Glu Ser Ile Gly Leu Tyr Met Glu Tyr Leu Val Leu Val
            35                  40                  45

Lys Asp Glu Glu Arg Phe Ser Glu Gln Tyr Glu Ile Leu Met Asn Asn
        50                  55                  60

Tyr Gln Ile Gln Gln Gly Asp Leu Ile Phe Ile Gln Trp Val Leu Lys
65                  70                  75                  80

Met Asn Thr Lys Ala Asn Ala Leu Ile Asp Asp Val Arg Ile Ile Ser
                85                  90                  95

Ala Leu His Asp Ala Ser Thr Leu Phe Glu Glu Pro Lys Tyr Ala Glu
            100                 105                 110

Ser Ala Asn Gln Leu Thr Leu Ala Ile Thr Ser Asn Gln Lys Ser Asn
        115                 120                 125

Gly Tyr Thr Val Asp Phe Tyr Asp Trp Ser Leu Asn Met Pro Ala Lys
    130                 135                 140

Arg Ile Thr Leu Ser Tyr Leu Thr Asn Glu Phe Phe Gln Ser Thr Thr
145                 150                 155                 160
```

```
Asp Thr Asp Asn Met Lys Asp Leu Leu Lys Asn Leu Asp Thr Thr
                165                 170                 175

Val Phe Phe Pro Glu Tyr Phe Asp Val Thr Lys Arg Lys Tyr Arg Glu
            180                 185                 190

Ser Glu Glu Val His Met Ile Asp Gln Leu Leu Ile Ala Ile Asn Arg
        195                 200                 205

Glu Asn Ile Gly Tyr Pro Ser Glu Ile Phe Lys Thr Trp Cys Leu Asn
    210                 215                 220

Glu Trp Lys His Glu Gly Lys Ile Tyr Gly Arg Tyr Asp Arg Gln Thr
225                 230                 235                 240

Lys Thr Ala Ser Val Thr Tyr Glu Ser Leu Ala Val Tyr Tyr Tyr Leu
                245                 250                 255

Asn Thr Tyr Phe Gln Lys Ile Asn Glu Pro Asp Leu Ala Lys Glu Val
            260                 265                 270

Leu Glu His Ala Glu Leu Leu Ala Ser Glu Ser Thr Ile Gly Glu Ala
        275                 280                 285

His Phe Phe Asp Tyr Ile His Phe Gln Leu Met Lys Lys Asn Met Glu
    290                 295                 300

<210> SEQ ID NO 57
<211> LENGTH: 281
<212> TYPE: PRT
<213> ORGANISM: Listeria monocytogenes

<400> SEQUENCE: 57

Val Lys Glu Asn Tyr Thr Ala Lys Asn Gly Leu Ile Met Asp Tyr Lys
1               5                   10                  15

Asn Thr Glu Glu Pro His Tyr Leu Ala Glu Ser Ile Gly Leu Tyr Met
            20                  25                  30

Glu Tyr Leu Val Glu Val Asn Asp Ser Lys Thr Phe Gln Lys Gln Val
        35                  40                  45

Asn His Leu Glu Lys Tyr Phe Ile Ala Glu Asp Asn Phe Ile Lys Trp
    50                  55                  60

Glu Ala Thr Asp Ser Thr Thr Thr Asn Ala Ile Val Asp Asp Phe Arg
65                  70                  75                  80

Ile Thr Glu Ala Leu Tyr Gln Ala Ser Glu Lys Phe Ser Phe Pro Ser
                85                  90                  95

Tyr Lys Lys Met Ala Asp Lys Phe Leu Thr Asn Thr Lys Lys Tyr Ser
            100                 105                 110

Ala Glu Gln Gly Val Pro Val Asp Phe Tyr Asp Phe Val His Lys Lys
        115                 120                 125

Lys Ala Asp Thr Leu His Leu Ser Tyr Leu Asn Ile Gln Ala Met Gln
    130                 135                 140

Gln Ile Asn Tyr Arg Asp Lys Ala Tyr Leu Pro Ile Gln Thr Ile Asn
145                 150                 155                 160

Ala Asp Pro Phe Phe Thr Glu Val Phe Gln Asn Gly Gln Phe Lys Phe
                165                 170                 175

Ala Asp Gln Lys Glu Val Asn Met Ile Asp Gln Met Leu Ile Ala Ile
            180                 185                 190

Ala Tyr Tyr Asp Glu Asn Gly Asp Ile Glu Pro Asn Phe Asp Asn Phe
        195                 200                 205

Leu Gln Thr Glu Leu Ala Ser Lys Gly Lys Ile Tyr Ala Arg Tyr Gln
    210                 215                 220

Arg Glu Thr Lys Lys Pro Ser Ser Glu Asn Glu Ser Thr Ala Val Tyr
225                 230                 235                 240
```

```
Ala Phe Leu Thr Gln Tyr Phe Asn Lys Thr Asn Gln Ala Lys Asn Gly
            245                 250                 255

Lys Ile Thr Lys Glu Leu Leu Glu Lys Met Asp Thr Ser Asn Pro Glu
            260                 265                 270

Thr Thr His Phe Phe Asp Tyr Ile Asn
            275                 280

<210> SEQ ID NO 58
<211> LENGTH: 285
<212> TYPE: PRT
<213> ORGANISM: Jeotgalibacillus campisalis

<400> SEQUENCE: 58

Val Lys Glu Gln Tyr Thr Asn Gln Glu Gly Leu Ile His Ala Tyr Pro
1               5                   10                  15

Leu Gln Gln Asp Ser Glu Tyr Leu Ser Glu Ile Gly Leu Tyr Met
            20                  25                  30

Glu Tyr Leu Val Leu Val Lys Asp Glu Glu Arg Phe Ser Glu Gln Tyr
            35                  40                  45

Glu Ile Leu Met Asn Asn Tyr Gln Ile Gln Gln Gly Asp Leu Ile Phe
50                  55                  60

Ile Gln Trp Val Leu Lys Met Asn Thr Lys Ala Asn Ala Leu Ile Asp
65                  70                  75                  80

Asp Val Arg Ile Ile Ser Ala Leu His Asp Ala Ser Thr Leu Phe Glu
            85                  90                  95

Glu Pro Lys Tyr Ala Glu Ser Ala Asn Gln Leu Thr Leu Ala Ile Thr
            100                 105                 110

Ser Asn Gln Lys Ser Asn Gly Tyr Thr Val Asp Phe Tyr Asp Trp Ser
            115                 120                 125

Leu Asn Met Pro Ala Lys Arg Ile Thr Leu Ser Tyr Leu Thr Asn Glu
            130                 135                 140

Phe Phe Gln Ser Thr Thr Asp Thr Asp Asn Met Lys Asp Leu Leu Lys
145                 150                 155                 160

Asn Leu Asp Asp Thr Thr Val Phe Phe Pro Glu Tyr Phe Asp Val Thr
            165                 170                 175

Lys Arg Lys Tyr Arg Glu Ser Glu Glu Val His Met Ile Asp Gln Leu
            180                 185                 190

Leu Ile Ala Ile Asn Arg Glu Asn Ile Gly Tyr Pro Ser Glu Ile Phe
            195                 200                 205

Lys Thr Trp Cys Leu Asn Glu Trp Lys His Gly Lys Ile Tyr Gly
            210                 215                 220

Arg Tyr Asp Arg Gln Thr Lys Thr Ala Ser Val Thr Tyr Glu Ser Leu
225                 230                 235                 240

Ala Val Tyr Tyr Tyr Leu Asn Thr Tyr Phe Gln Lys Ile Asn Glu Pro
            245                 250                 255

Asp Leu Ala Lys Glu Val Leu Glu His Ala Glu Leu Leu Ala Ser Glu
            260                 265                 270

Ser Thr Ile Gly Glu Ala His Phe Phe Asp Tyr Ile His
            275                 280                 285

<210> SEQ ID NO 59
<211> LENGTH: 298
<212> TYPE: PRT
<213> ORGANISM: Bacillus thermotolerans

<400> SEQUENCE: 59
```

```
Met Gln Lys Asp Thr Glu Ala Ala Trp Ser Glu Glu Phe Ile Arg
1               5                   10                  15

Ile Val His Gln Tyr Tyr Met Asp Asp Ser Gly Lys Ile Arg Ser Tyr
                20                  25                  30

Gly Thr Glu Glu Asn Glu Glu Tyr Leu Leu Glu Ser Met Gly Leu Tyr
            35                  40                  45

Met Lys Trp Leu Ser Gly His Asn Arg Glu Glu Val Gln Glu Leu
50                  55                  60

Arg Lys Thr Val Gln Ser Glu Phe Ala Tyr Glu His Ala Ser Asp Val
65                  70                  75                  80

Phe Leu Ser Trp Arg Val Glu Gly Asp Gln Gln Ala Ser Val Asn Ala
                85                  90                  95

Trp Ile Asp Asp Ala Arg Ile Leu Ser Val Leu Gly Pro Ala Asp Pro
                100                 105                 110

Leu Phe Asn Lys Ile Ala Asp Thr Leu Lys Lys Tyr Gln Val Gln Asn
            115                 120                 125

Gly Leu Ile Val Asp Phe Tyr Asp Trp Glu Gln Glu Ala Ala Ser Glu
130                 135                 140

Arg Val Val Leu Ser Tyr Gly Thr Arg Glu Glu Asp Ala Leu Arg Leu
145                 150                 155                 160

Thr Ser Met Asp Arg Leu Tyr Leu Glu Ala Ser Thr Arg Ser Asp Pro
                165                 170                 175

Phe Tyr Pro Glu Phe Tyr Asp Val Lys Glu Lys Lys Phe Ile Glu Ser
            180                 185                 190

Asp Glu Val His Met Val Asp Gln Leu Leu Ile Ala Ile Gln Leu Glu
            195                 200                 205

Lys Glu Lys Gly Asp Asn His Glu Phe Trp Gln Trp Leu Val Ser Glu
210                 215                 220

Trp Glu Lys His Gln Ala Ile Ser Gly Arg Tyr Asp Arg Asn Ser His
225                 230                 235                 240

Lys Gly Asn Gly Ile Glu Ser Gly Ala Val Tyr Gly Ile Ala Ala Glu
                245                 250                 255

Trp Ala Leu Leu Lys Gly Glu Glu Leu Ala Glu Lys Trp Lys His
                260                 265                 270

Lys Gly Phe Gln Leu Val Asn Pro Lys Asp His Gln Phe Asp His Ile
            275                 280                 285

His Phe Phe Asp Leu Ile Trp Asn Ala Pro
290                 295

<210> SEQ ID NO 60
<211> LENGTH: 246
<212> TYPE: PRT
<213> ORGANISM: Listeria monocytogenes

<400> SEQUENCE: 60

Val Lys Glu Asn Tyr Thr Ala Lys Asn Gly Leu Ile Met Asp Tyr Lys
1               5                   10                  15

Asn Thr Glu Glu Pro His Tyr Leu Ala Glu Ser Ile Gly Leu Tyr Met
                20                  25                  30

Glu Tyr Leu Val Glu Val Asn Asp Ser Lys Thr Phe Gln Lys Gln Val
            35                  40                  45

Asn His Leu Glu Lys Tyr Phe Ile Ala Glu Asp Asn Phe Ile Lys Trp
50                  55                  60

Glu Ala Thr Asp Ser Thr Thr Thr Asn Ala Ile Val Asp Asp Phe Arg
```

```
            65                  70                  75                  80
Ile Thr Glu Ala Leu Tyr Gln Ala Ser Glu Lys Phe Ser Phe Pro Ser
                85                  90                  95

Tyr Lys Lys Met Ala Asp Lys Phe Leu Thr Asn Thr Lys Lys Tyr Ser
               100                 105                 110

Ala Glu Gln Gly Val Pro Val Asp Phe Tyr Asp Phe Val His Lys Lys
               115                 120                 125

Lys Ala Asp Thr Leu His Leu Ser Tyr Leu Asn Ile Gln Ala Met Gln
           130                 135                 140

Gln Ile Asn Tyr Arg Asp Lys Ala Tyr Leu Pro Ile Gln Thr Ile Asn
145                 150                 155                 160

Ala Asp Pro Phe Phe Thr Glu Val Phe Gln Asn Gly Gln Phe Lys Phe
                165                 170                 175

Ala Asp Gln Lys Glu Val Asn Met Ile Asp Gln Met Leu Ile Ala Ile
            180                 185                 190

Ala Tyr Tyr Asp Glu Asn Gly Asp Ile Glu Pro Asn Phe Asp Asn Phe
                195                 200                 205

Leu Gln Thr Glu Leu Ala Ser Lys Gly Lys Ile Tyr Ala Arg Tyr Gln
            210                 215                 220

Arg Glu Thr Lys Lys Pro Ser Ser Glu Asn Glu Ser Thr Ala Val Tyr
225                 230                 235                 240

Ala Phe Leu Thr Gln Tyr
                245

<210> SEQ ID NO 61
<211> LENGTH: 240
<212> TYPE: PRT
<213> ORGANISM: Bacillus thermotolerans

<400> SEQUENCE: 61

Val His Gln Tyr Tyr Met Asp Asp Ser Gly Lys Ile Arg Ser Tyr Gly
1               5                  10                  15

Thr Glu Glu Asn Glu Glu Tyr Leu Leu Glu Ser Met Gly Leu Tyr Met
                20                  25                  30

Lys Trp Leu Ser Gly His Asn Arg Glu Glu Val Gln Glu Leu Arg
            35                  40                  45

Lys Thr Val Gln Ser Glu Phe Ala Tyr Glu His Ala Ser Asp Val Phe
50                  55                  60

Leu Ser Trp Arg Val Glu Gly Asp Gln Gln Ala Ser Val Asn Ala Trp
65                  70                  75                  80

Ile Asp Asp Ala Arg Ile Leu Ser Val Leu Gly Pro Ala Asp Pro Leu
                85                  90                  95

Phe Asn Lys Ile Ala Asp Thr Leu Lys Lys Tyr Gln Val Gln Asn Gly
            100                 105                 110

Leu Ile Val Asp Phe Tyr Asp Trp Glu Gln Glu Ala Ala Ser Glu Arg
        115                 120                 125

Val Val Leu Ser Tyr Gly Thr Arg Glu Glu Asp Ala Leu Arg Leu Thr
    130                 135                 140

Ser Met Asp Arg Leu Tyr Leu Glu Ala Ser Thr Arg Ser Asp Pro Phe
145                 150                 155                 160

Tyr Pro Glu Phe Tyr Asp Val Lys Glu Lys Phe Ile Glu Ser Asp
                165                 170                 175

Glu Val His Met Val Asp Gln Leu Leu Ile Ala Ile Gln Leu Glu Lys
            180                 185                 190
```

Glu Lys Gly Asp Asn His Glu Phe Trp Gln Trp Leu Val Ser Glu Trp
            195                 200                 205

Glu Lys His Gln Ala Ile Ser Gly Arg Tyr Asp Arg Asn Ser His Lys
    210                 215                 220

Gly Asn Gly Ile Glu Ser Gly Ala Val Tyr Gly Ile Ala Ala Glu Trp
225                 230                 235                 240

<210> SEQ ID NO 62
<211> LENGTH: 118
<212> TYPE: PRT
<213> ORGANISM: Unknown
<220> FEATURE:
<223> OTHER INFORMATION: Description of Unknown: PssZ polypeptide,
      consensus of the Hidden Markov Model (HMM)

<400> SEQUENCE: 62

Lys Ser Lys Tyr Leu Lys Thr Asp Gly Arg Val Ile Asp Thr Ala Asn
1               5                   10                  15

Gly Asn Lys Asp Thr Val Ser Glu Gly Gln Gly Tyr Gly Met Leu Leu
            20                  25                  30

Ala Val Ala Ala Ala Asp Arg Ala Ala Phe Asp Asn Leu Tyr Lys Trp
        35                  40                  45

Thr Lys Ala Asn Leu Ser Ser Thr Asn Glu Lys Leu Met Ala Trp Arg
    50                  55                  60

Val Asn Lys Ser Lys Lys Asn Lys Val Glu Asp Lys Asn Ser Ala Thr
65                  70                  75                  80

Asp Gly Asp Leu Leu Ile Ala Tyr Ser Leu Leu Leu Ala Gly Lys Gln
                85                  90                  95

Trp Gly Ser Gly Arg Tyr Asn Tyr Leu Lys Glu Ala Lys Asn Ile Ile
            100                 105                 110

Ile Ala Ile Lys Asn Val
            115

<210> SEQ ID NO 63
<211> LENGTH: 112
<212> TYPE: PRT
<213> ORGANISM: Listeria innocua

<400> SEQUENCE: 63

Lys Glu Asn Tyr Met Thr Lys Asn Gly Leu Ile Ile Asp Tyr Lys Asn
1               5                   10                  15

Ala Gln Glu Pro His Tyr Leu Ala Glu Ser Ile Gly Leu Tyr Met Glu
            20                  25                  30

Tyr Leu Val Glu Val Asn Asp Ser Lys Thr Phe Gln Glu Gln Val Ala
        35                  40                  45

Thr Leu Gln Lys His Phe Ile Thr Thr Asp Asn Phe Ile Lys Trp Glu
    50                  55                  60

Ala Thr Asp Ser Thr Thr Thr Asn Ala Ile Val Asp Asp Phe Arg Ile
65                  70                  75                  80

Thr Glu Ala Leu Tyr Gln Ala Ser Lys Lys Trp Asp His Gln Ala Tyr
                85                  90                  95

Gln Thr Leu Ala Asp Thr Leu Ile Ser Asn Thr Lys Lys Tyr Ser Ala
            100                 105                 110

<210> SEQ ID NO 64
<211> LENGTH: 112
<212> TYPE: PRT
<213> ORGANISM: Listeria monocytogenes

```
<400> SEQUENCE: 64

Lys Glu Asn Tyr Thr Ala Lys Asn Gly Leu Ile Met Asp Tyr Lys Asn
1               5                   10                  15

Thr Glu Glu Pro His Tyr Leu Ala Glu Ser Ile Gly Leu Tyr Met Glu
            20                  25                  30

Tyr Leu Val Glu Val Asn Asp Ser Lys Thr Phe Gln Lys Gln Val Asn
        35                  40                  45

His Leu Glu Lys Tyr Phe Ile Ala Glu Asp Asn Phe Ile Lys Trp Glu
    50                  55                  60

Ala Thr Asp Ser Thr Thr Thr Asn Ala Ile Val Asp Asp Phe Arg Ile
65              70                  75                  80

Thr Glu Ala Leu Tyr Gln Ala Ser Glu Lys Phe Ser Phe Pro Ser Tyr
            85                  90                  95

Lys Lys Met Ala Asp Lys Phe Leu Thr Asn Thr Lys Lys Tyr Ser Ala
            100                 105                 110
```

COMPOSITIONS AND METHODS FOR MAKING AND USING HYDROLYTIC ENZYMES FOR DEGRADING POLYSACCHARIDES MADE BY FOODBORNE PATHOGENIC BACTERIA

RELATED APPLICATIONS

This application claims priority to U.S. Provisional Application No. 62/072,358, filed under 35 U.S.C. § 111(b) on Oct. 29, 2014, the disclosure of which is incorporated herein by reference in its entirety.

STATEMENT REGARDING FEDERALLY SPONSORED RESEARCH

This invention was made with government support under Hatch Grant project number WYO-491-13 awarded by the United States Department of Agriculture, National Institute of Food and Agriculture; and grant number MCB1052575 awarded by the National Science Foundation. The government has certain rights in this invention.

SEQUENCE LISTING

The instant application contains a Sequence Listing which has been submitted electronically in ASCII format and is hereby incorporated by reference in its entirety. Said ASCII copy, created on Oct. 29, 2015, is named 53-56551_15-027_SL.txt and is 57,439 bytes in size.

BACKGROUND OF THE INVENTION

Bacteria can form exopolysaccharide-rich aggregates, or biofilms, that pose formidable challenges in medicine and industry because of their resistance to antibiotics, disinfectants, desiccation, and other treatments. One of the common foodborne pathogens, *Listeria monocytogenes*, can form biofilms on food products, food-processing equipment, and in food storage facilities. When consumed with food, *L. monocytogenes* may cause listeriosis, a severe disease that has the highest fatality rate of the foodborne diseases in the developed countries. Listeriosis is particularly dangerous for immunocompromised individuals, pregnant women, the elderly, and infants. Despite a relatively low number of cases, it is the third most costly foodborne disease in the USA, with the total annual financial loss estimated at $8.8 billion. Thus, there is a need for new and improved means for degrading biofilms and combating *L. monocytogenes*.

SUMMARY OF THE INVENTION

Described are uses of a *Listeria monocytogenes* PssZ protein, homolog, variant, or fragment, in preventing bacterial exopolysaccharide-dependent aggregation, in degrading a biofilm, and in inhibiting biofilm formation on a surface.

Provided is a *L. monocytogenes* PssZ protein having the sequence: MKRFILILILLIFIGAGFFIFLRPESKKTVSAP-KETTPTSTSV QTYVKENYTAKNGLIMDYKN-TEEPHYLAESIGLYMEYLVEVNDSKTFQKQVNHLE-KYFIAEDNFIKWEATDSTTTNAIVDDFRITEALYQAS-EKFSFPSYKKMADKFLTNTKKYSAEQGVPVDFYD-FVHKKKADTLHLSYLNIQAMQQINYRDKAYLPIQTI-NADPFFTEVFQNGQFKFADQKEVNMIDQMLIA-IAYYDENGDIEPNFDNFLQTELASKGKIYARYQRE TKKPSSENESTAVYAFLTQYFNKTNQAKNGKIT-KELLEKMDTSNPETTHFFDYINKEITLKK [SEQ ID NO: 1].

Also provided are PssZ variants comprising 90%, 80%, 70%, or 60% sequence identity to the purified *L. monocytogenes* PssZ protein. Also provided is a PssZ E72Q mutant comprising an *L. monocytogenes* PssZ protein having a Glu72 site substituted with glutamine.

Also provided is a purified PssZ fragment having the sequence: RPESKKTVSAPKETTPTSTSVQTYVKENY-TAKNGLIMDYKNTEEPHYLAES IGLYMEYLVEVND-SKTFQKQVNHLEKYFIAEDNFIKWEATDSTTTNA-IVDDFRITEALYQASEKFSFPSYKKMADKFLTNTKKY-SAEQGVPVDFYDFVHKKKADTLHLSYLNIQAMQQ-INYRDKAYLPIQTINADPFFTEVFQNGQFKFADQKEV-NMIDQMLIAIAYYDENGDIEPNFDNFLQTELASKGKI-YARYQRETKKPSSENESTAVYAFLTQYFNKTNQAKNG KITKELLEKMDTSNPETTHFFDYINKEITLKK [SEQ ID NO: 2].

Also provided are homologs of the *L. monocytogenes* PssZ protein. In certain embodiments, the PssZ homolog is selected from the group consisting of: *Exiguobacterium undae* PssZ [SEQ ID NO: 47], *Carnobacterium mobile* PssZ [SEQ ID NO: 50], *Carnobacterium jeotgali* PssZ [SEQ ID NO: 53], *Jeotgalibacillus campisalis* PssZ [SEQ ID NO: 56], and *Bacillus thermotolerans* PssZ [SEQ ID NO: 59].

Also provided is the use of a purified *L. monocytogenes* PssZ protein, a PssZ protein homolog, or a variant or fragment thereof, in hydrolyzing a listerial exopolysaccharide, or in preventing bacterial exopolysaccharide-dependent aggregation.

Further provided is a method of hydrolyzing a listerial exopolysaccharide, where the method involves exposing *listeria* bacteria to a sufficient amount of a purified *L. monocytogenes* PssZ protein, a PssZ protein homolog, or a variant or fragment thereof, and hydrolyzing a listerial exopolysaccharide. In certain embodiments, the listerial exopolysaccharide comprises ManNAc-Gal Pss exopolysaccharide. In certain embodiments, the *listeria* bacteria is present in a food article.

Further provided is a method of preventing bacterial exopolysaccharide-dependent aggregation on a surface, where the method involves applying a sufficient amount of a purified *L. monocytogenes* PssZ protein, a PssZ protein homolog, or variant or fragment thereof, to a surface, and preventing bacterial exopolysaccharide-dependent aggregation on the surface. In certain embodiments, aggregation of *L. monocytogenes* is prevented. In certain embodiments, the surface comprises a food container surface. In certain embodiments, the surface comprises surface of fruit, vegetables, or other plant materials.

Further provided is a method of disintegrating bacterial exopolysaccharide-rich aggregates, where the method involves applying a sufficient amount of a purified *L. monocytogenes* PssZ protein, a PssZ protein homolog, or a variant or fragment thereof, to a bacterial aggregate, and disintegrating the bacterial aggregate.

Further provided is a method of inhibiting a listerial contamination in a food article, where the method involves applying a sufficient amount of a purified *L. monocytogenes* PssZ protein, a PssZ protein homolog, or a variant or fragment thereof, to a food article, and inhibiting a listerial growth in the food article.

Further provided is a method of ameliorating a listerial contamination in a food article, where the method involves applying a sufficient amount of a purified *L. monocytogenes* PssZ protein, a PssZ protein homolog, or a variant or fragment thereof, to a food article contaminated with *L. monocytogenes*, and applying a sufficient amount of an antibacterial agent to the food article, to ameliorate the listerial contamination in the food article. In certain embodiments, the antibacterial agent is bleach (sodium hypochlorite), hydrogen peroxide, or another disinfectant.

Further provided is a disinfecting solution that includes a PssZ protein, a PssZ protein homolog, or a variant or fragment thereof, and an antibacterial agent. In certain embodiments, the antibacterial agent is a detergent. In certain embodiments, the antibacterial agent is bleach. In certain embodiments, the antibacterial agent is selected from the group consisting of: hydrogen peroxide, alcohol, iodophor, quaternary ammonia compounds, chlorine solutions, peracetic acid, peroctanoic acid, nitric acid, benzoic acid, sodium hydroxide, dimethyl benzyl lauryl ammonium bromide, cationic surfactants, anionic surfactants, non-ionic surfactants, zwitterionic surfactants, nisin, lauricidin, lactoperoxidase, ampicillin, vancomycin, ciprofloxacin, azithromycin, or a proteolytic enzyme. In certain embodiments, the disinfecting solution has a pH ranging from about 4 to about 10.

Further provided is a polysaccharide composition that includes a ManNAc-Gal exopolysaccharide (EPS) having a trisaccharide repeating unit of {4)-β-ManpNAc-(1-4)-[α-Galp-(1-6)]-β-ManpNAc-(1-}, wherein ManpNAc is N-acetylmannosamine and Galp is galactose. In certain embodiments, the composition is a food additive or filler.

Further provided is a method of administering a probiotic, where the method involves protecting a therapeutically effective amount of a microorganism with an EPS coating to form a protected probiotic, and administering the protected probiotic to a patient in need thereof.

Further provided is a kit for treating a bacterial contamination, where the kit includes a first container housing a PssZ enzyme solution, and a second container housing a disinfectant solution. In certain embodiments, the PssZ enzyme solution comprises a PssZ protein, a PssZ protein homolog, or a variant or fragment thereof.

In certain embodiments, the PssZ protein homolog is selected from the group consisting of: *Exiguobacterium undae* PssZ [SEQ ID NO: 47], *Carnobacterium mobile* PssZ [SEQ ID NO: 50], *Carnobacterium jeotgali* PssZ [SEQ ID NO: 53], *Jeotgalibacillus campisalis* PssZ [SEQ ID NO: 56], and *Bacillus thermotolerans* PssZ [SEQ ID NO: 59].

In certain embodiments, the fragment is a PssZ fragment having the sequence:

```
                                            [SEQ ID NO: 2]
RPESKKTVSAPKETTPTSTSVQTYVKENYTAKNGLIMDYKNTEEPHYL

AESIGLYMEYLVEVNDSKTFQKQVNHLEKYFIAEDNFIKWEATDSTTT

NAIVDDFRITEALYQASEKFSFPSYKKMADKFLTNTKKYSAEQGVPVD

FYDFVHKKKADTLHLSYLNIQAMQQINYRDKAYLPIQTINADPFFTEV

FQNGQFKFADQKEVNMIDQMLIAIAYYDENGDIEPNFDNFLQTELASK

GKIYARYQRETKKPSSENESTAVYAFLTQYFNKTNQAKNGKITKELLE

KMDTSNPETTHFFDYINKEITLKK.
```

In certain embodiments, the PssZ variants comprise 90%, 80%, 70%, or 60% sequence identity to the purified *L. monocytogenes* PssZ protein.

BRIEF DESCRIPTION OF THE DRAWINGS

The patent or application file may contain one or more drawings executed in color and/or one or more photographs.

Copies of this patent or patent application publication with color drawing(s) and/or photograph(s) will be provided by the U.S. Patent and Trademark Office upon request and payment of the necessary fees.

FIG. 1: In silico analysis of genes and proteins involved in c-di-GMP signaling in *L. monocytogenes*. Depicted are genes believed to encode DGCs (DgcA-C), c-di-GMP PDEs (PdeB-D), a c-di-GMP receptor (PssE), and listerial EPS biosynthesis machinery. Protein domain architectures are taken from the Pfam database: 5TM, a conserved five-transmembrane module; unmarked red box, transmembrane domain; crossed GGDEF domain ("GGDEF" disclosed as SEQ ID NO: 3), enzymatically inactive GGDEF domain ("GGDEF" disclosed as SEQ ID NO: 3).

Figure 4A:
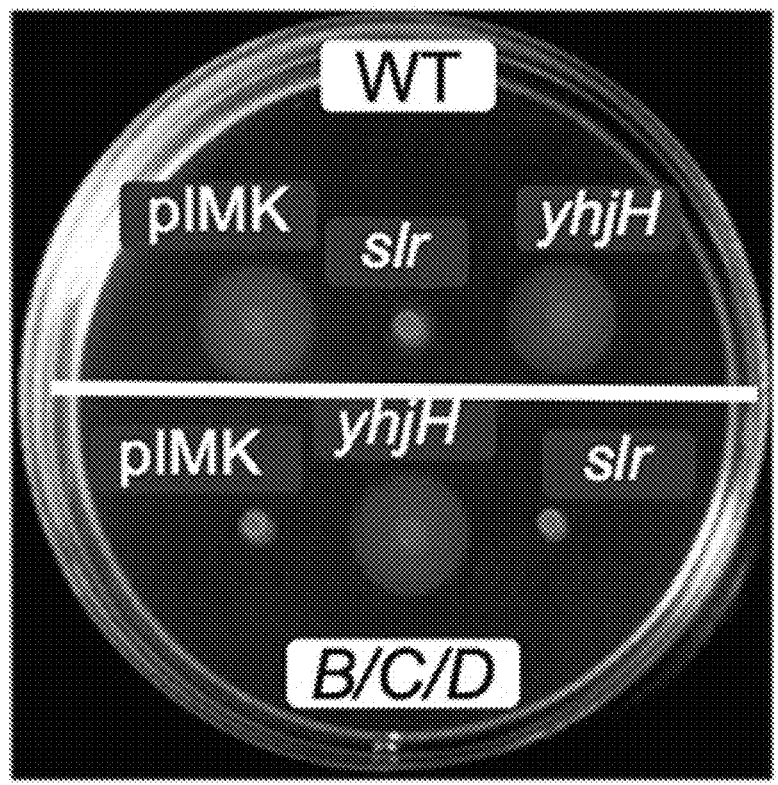
Figure 4B:
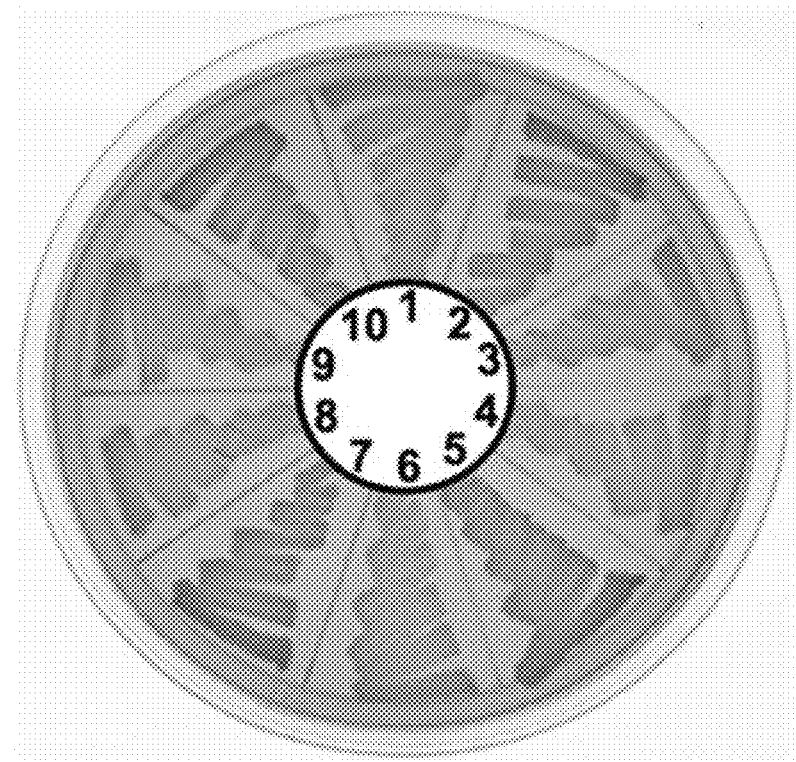
Figure 4C:
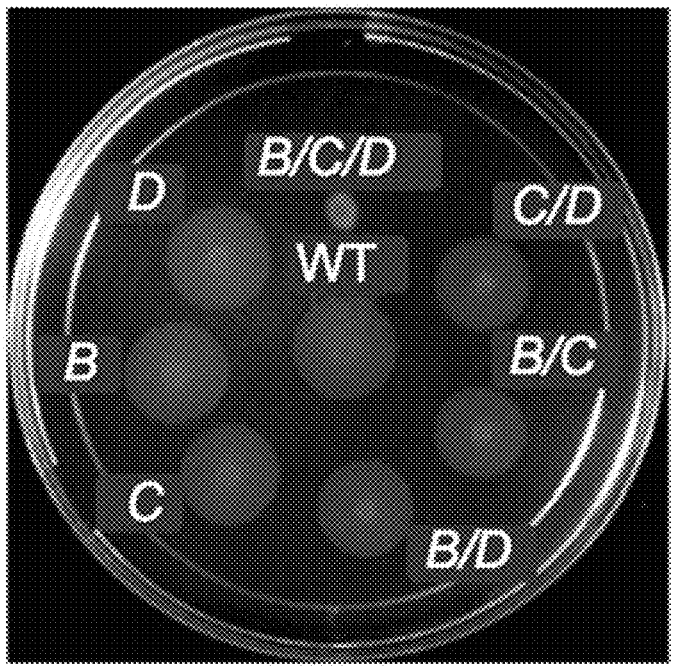
Figure 4D:
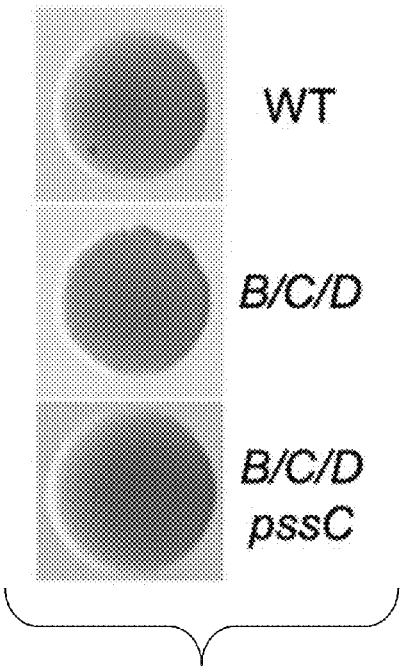
Figure 4E:
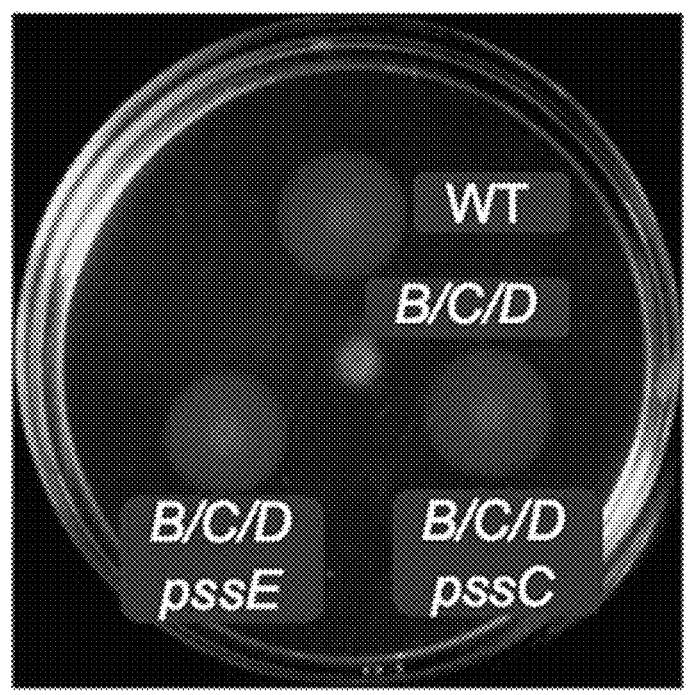

FIGS. 2A-2C: PDE activities of the *L. monocytogenes* proteins PdeBD. FIG. 2A shows restoration of motility in semi-solid (0.25%) agar of strain MG1655 DyhjH by *L. monocytogenes* PdeB, PdeC, and PdeD is indicative of their cdi-GMP PDE activities. PdeB-D were expressed as C-terminal His6-fusions ("His6" disclosed as SEQ ID NO: 4) downstream of the T7 promoter from vector pET23a. Although MG1655 does not encode a T7 RNA polymerase gene, the pde genes were expressed from a fortuitous promoter at sufficiently high levels to partially restore the swimming defect of MG1655 DyhjH in semi-solid agar. pET, empty vector (pET23a). FIG. 2B shows affinity purified *L. monocytogenes* PdeD (PdeD::His6) ("His6" disclosed as SEQ ID NO: 4), PdeB (PdeB::His6) ("His6" disclosed as SEQ ID NO: 4), and PdeC (MBP::PdeC) proteins used in the PDE assays. MW, molecular weight, kD. FIG. 2C shows PDE activities of PdeD::His6 ("His6" disclosed as SEQ ID NO: 4), PdeB::His6 ("His6" disclosed as SEQ ID NO: 4) and MBP::PdeC monitored by the rates of formation of pGpG, the product of c-di-GMP hydrolysis. Nucleotides were measured by HPLC as described in the examples.

FIGS. 3A-3B: DGC activities of the *L. monocytogenes* proteins DgcAC. FIG. 3A shows inhibition of motility in semi-solid (0.25%) agar of strain MG1655 by *L. monocytogenes* DgcA (plasmid pBAD-dgcA), DgcB (pBAD-dgcB), and DgcC (pBAD-dgcC) is indicative of their DGC activities. DgcA-C were expressed from the vector pBAD/Myc-His-C (pBAD). LB agar contained 0.1% arabinose. FIG. 3B shows Congo red staining of the fimbriae producing strain BL21(DE3) caused by *L. monocytogenes* DgcA, DgcB, and DgcC is indicative of their DGC activities. LB agar contained 0.001% arabinose.

FIGS. 4A-4E: Inhibition of motility and activation of EPS production in *L. monocytogenes* by elevated levels of c-di-GMP. FIG. 4A, top, shows inhibition of swimming of the wild-type *L. monocytogenes* in semi-solid agar by a heterologous DGC, Slr1143. FIG. 4A, bottom, shows restoration of swimming in semi-solid agar of the *L. monocytogenes* ΔpdeB/C/D mutant by a heterologous PDE, YhjH. WT, wild type, EGD-e; A/B/C, ΔpdeB/C/D mutant; pIMK, WT::pIMK2 (vector control); slr, WT::(pIMK2::slr1143); yhjH, WT::(pIMK2::yhjH). FIG. 4B shows Congo red staining of EPS in *L. monocytogenes*. 1, WT, wild type; 2, ΔpdeB/C/D; 3, ΔpdeB/C/D ΔpssE; 4, ΔpdeB/C/D ΔpssC; 5, ΔpdeB/C/D::pIMK2; 6, ΔpdeB/C/D::pIMK2::yhjH; 7, ΔpdeB/C/D::(pIMK2::slr1143); 8, WT::pIMK2; 9, WT::(pIMK2::yhjH); 10, WT::(pIMK2::slr1143). FIG. 4C shows deletion of all three c-di-GMP PDEs drastically inhibits motility of *L. monocytogenes* in semi-solid agar. WT, wild type strain, B, ΔpdeB; C, ApdeC; D, ApdeD; B/D, ΔpdeB ApdeD; C/D, ApdeC ApdeD; B/C, ΔpdeB ApdeC; B/C/D, ΔpdeB/C/D. FIG. 4D shows rough colony morphology and increased Congo red staining of the *L. monocytogenes* ΔpdeB/C/D mutant and rescue of the wild-type colony morphology by the ΔpssC mutation (ΔpdeB/C/D ΔpssC). FIG. 4E shows restoration of motility of the ΔpdeB/C/D mutant by the ΔpssC or ΔpssE mutations.

Figure 5A:
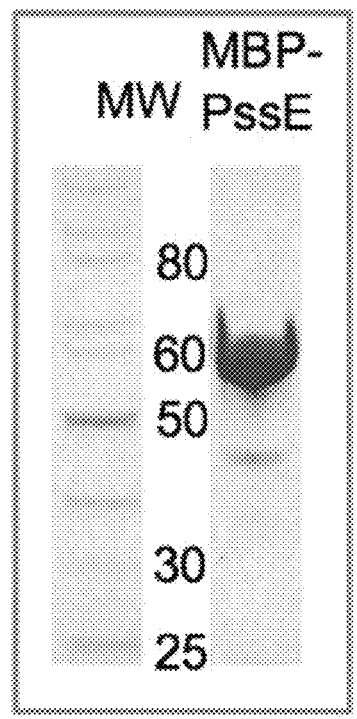
Figure 5B:
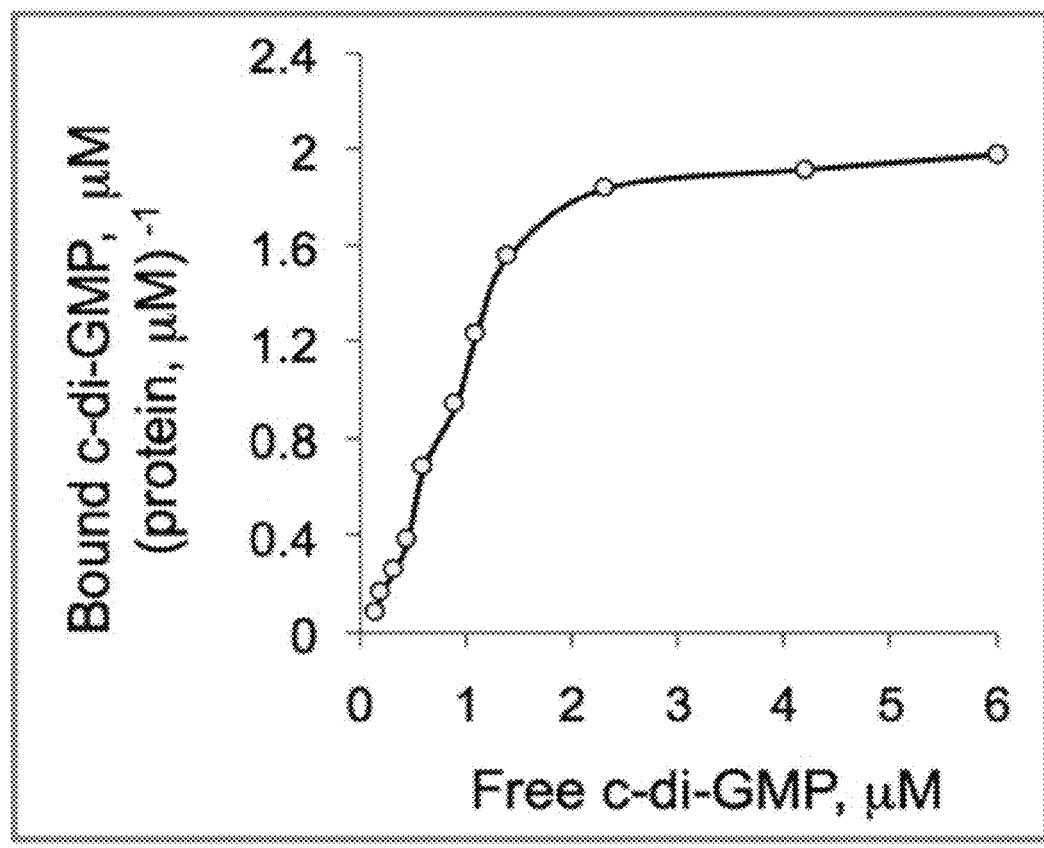

FIGS. 5A-5B: In vitro assay of c-di-GMP binding by the PssE receptor. FIG. 5A shows the MBP-PssE protein purified via affinity (amylose resin) chromatography. The GGDEF domain of PssE (residues 107-285) ("GGDEF" disclosed as SEQ ID NO: 3) containing the putative I-site was fused downstream of MBP, MBP::GGDEFpssE ("GGDEF" disclosed as SEQ ID NO: 3), and used in c-di-GMP binding assays. FIG. 5B shows a saturation plot of equilibrium binding of c-di-GMP to the PssE receptor (MBP::GGDEFpssE) ("GGDEF" disclosed as SEQ ID NO: 3). Shown is the dependence of the ratio of bound cdi-GMP per protein in the dialysis chamber, where protein alone was loaded, versus concentration of free c-di-GMP at equilibrium.

Figure 6A:
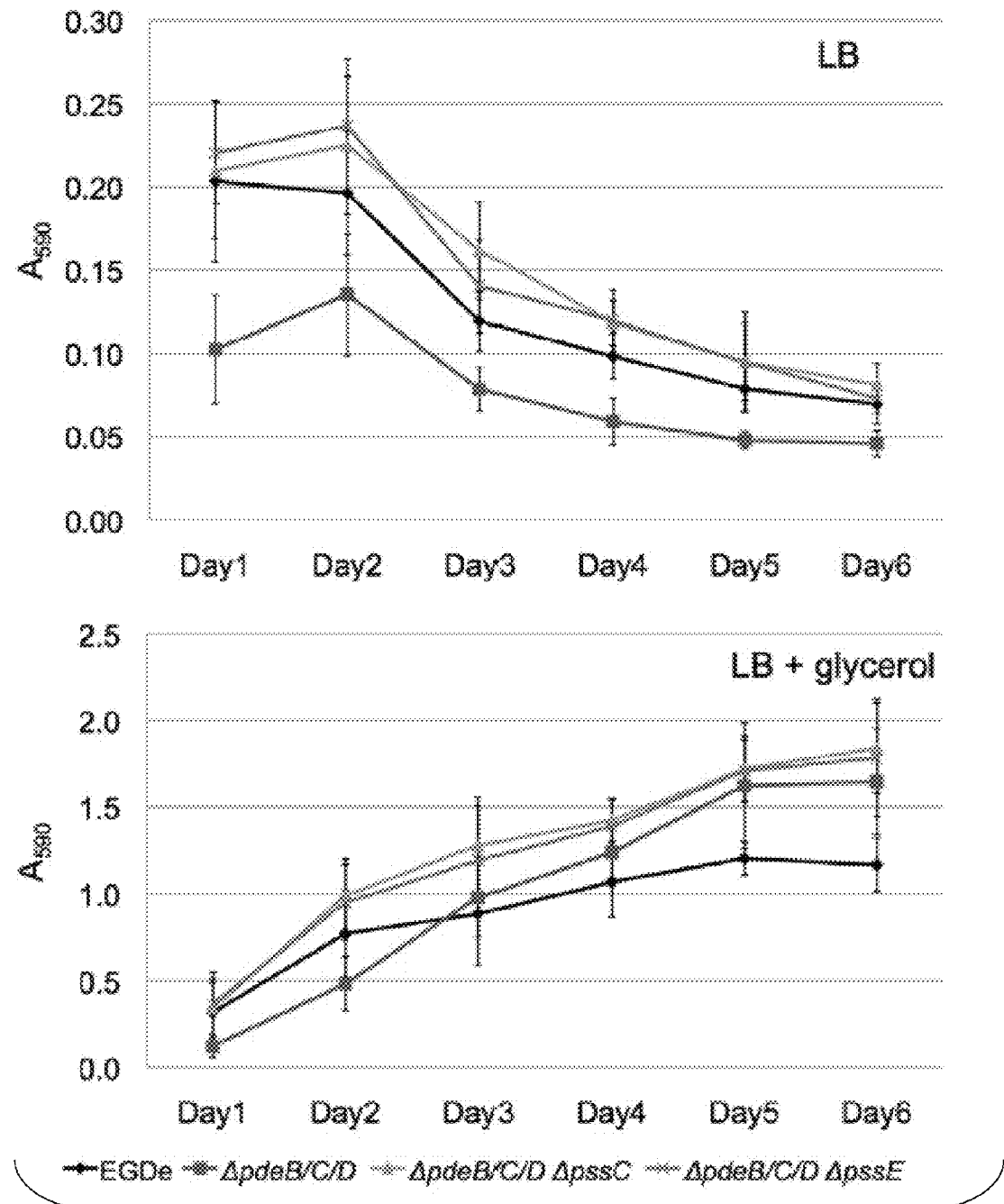
Figure 6B:
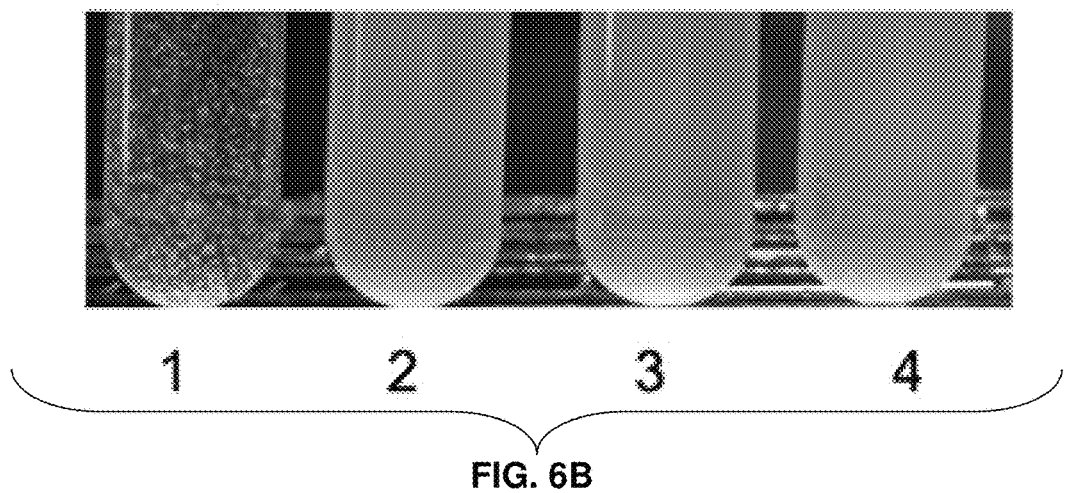
Figure 6C:
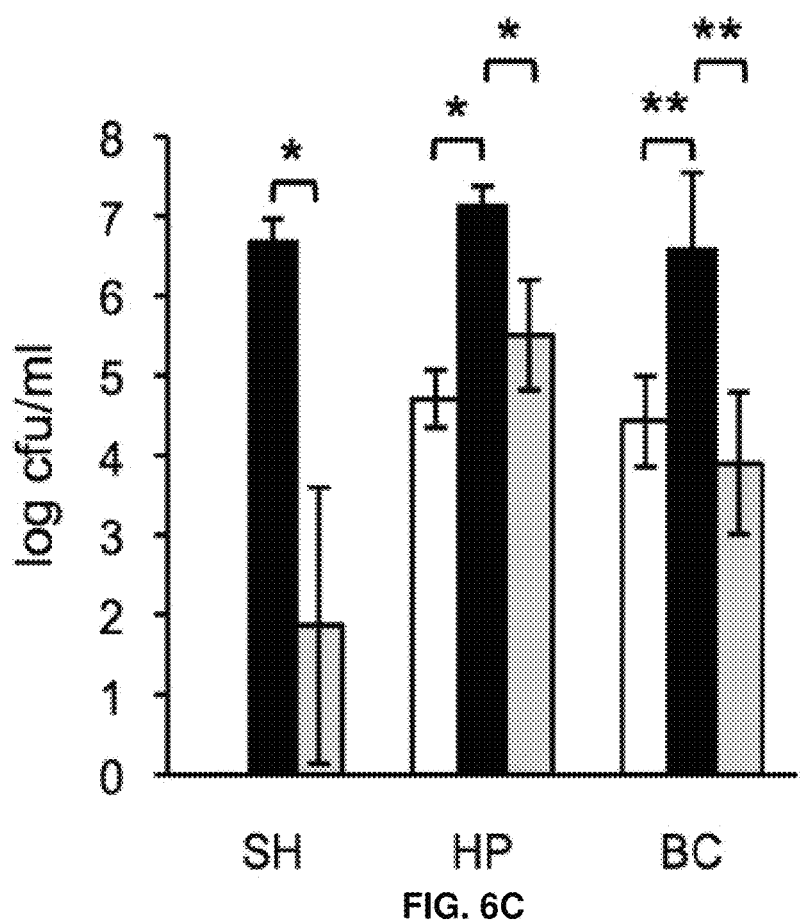
Figure 6D:
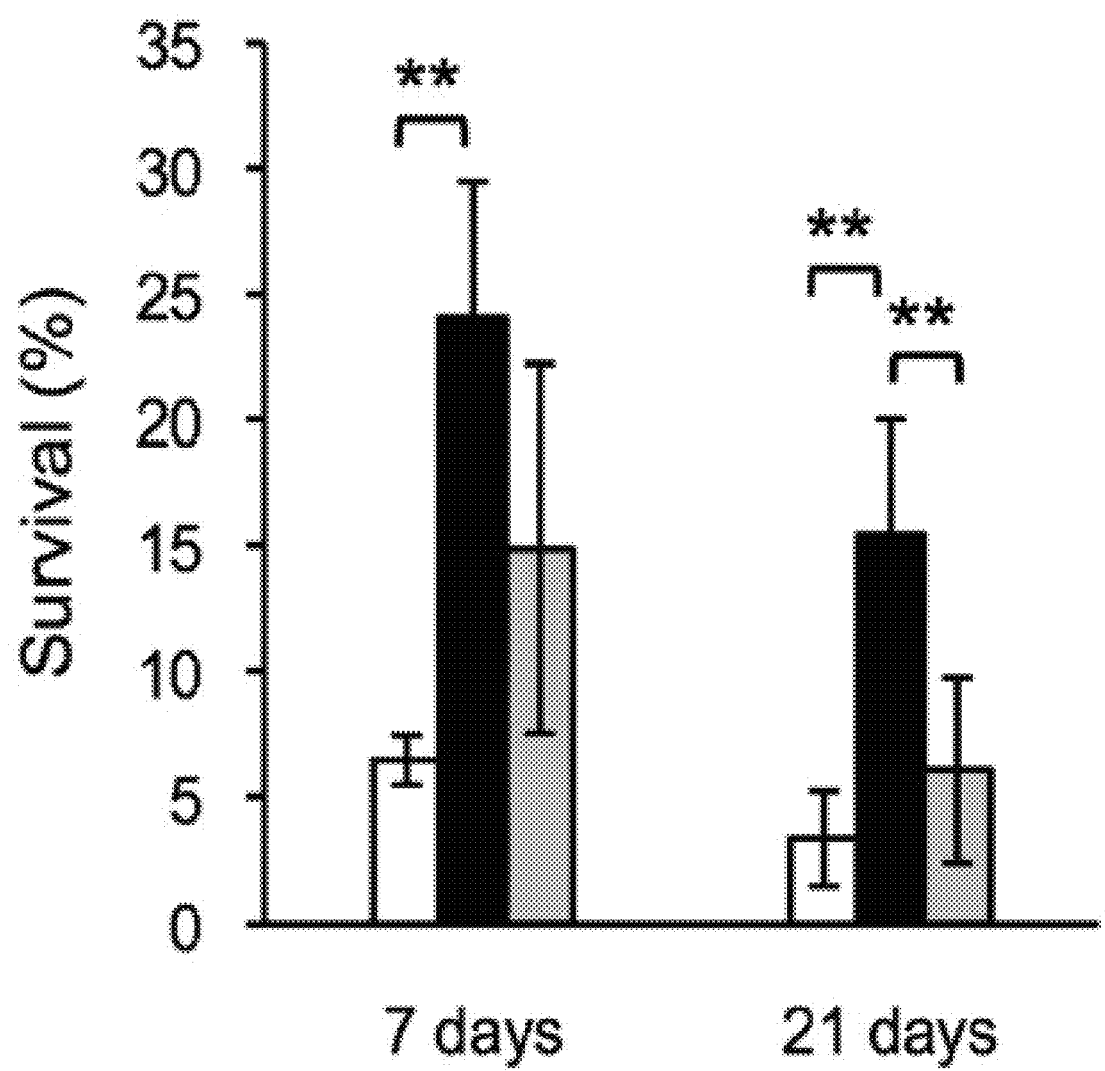

FIGS. 6A-6D: Role of the c-di-GMP-induced EPS in biofilm formation, cell aggregation, and tolerance of *L. monocytogenes* to disinfectants and desiccation. FIG. 6A shows biofilm formation of *L. monocytogenes* in 96-well polystyrene plates (measured using a Crystal violet dyebinding assay). Cultures were grown for 6 days at 30° C. in LB (top panel) or LB supplemented with 3% glycerol (bottom panel). Shown are average results from two biological replicates, where each strain was grown in six wells in a replicate (i.e., six technical replicates). Black circle, wild type; red square, ΔpdeB/C/D; green triangle, ΔpdeB/C/D ΔpssC; blue cross, ΔpdeB/C/D ΔpssE. FIG. 6B shows EPS-dependent *L. monocytogenes* cell aggregation (clumping) in HTM medium. Overnight cultures grown in BHI were inoculated into HTM liquid medium at A600 of 0.01 and incubated at 30° C. with gentle shaking (rotary shaker, 125 rpm) for 48 h. 1, ΔpdeB/C/D; 2, wild type; 3, ΔpdeB/C/D ΔpssC; 4, ΔpdeB/C/D ΔpssE. FIG. 6C shows the protective role of the c-di-GMP-inducible EPS in disinfection. Aliquots of the HTM-grown cultures were mixed with disinfectant solutions for 10 min at room temperature. Disinfection was stopped by adding a D/E neutralizing broth (Difco); the cultures were vortexed vigorously (5 min) with glass beads to break clumps and plated on BHI agar. Colonies were enumerated after a 48-h growth at 37° C. SH, sodium hydrochloride (1600 ppm); HP, hydrogen peroxide (200 mM); BC, benzalkonium chloride (100 ppm). White background, EGD-e; black, ΔpdeB/C/D; grey, ΔpdeB/C/D ΔpssC. SH, sodium hypochlorite; HP, hydrogen peroxide; BC, benzalkonium chloride. The absence of the bar for the EGD-e strain treated with SH indicates the lack of survivors. FIG. 6D shows the protective role of the c-di-GMP inducible EPS in desiccation. Aliquots of overnight cultures grown in HTM at 37° C. were spun down, the supernatants were removed, and cell pellets were stored in desiccators at room temperature for the indicated periods. The pellets were rehydrated, vortexed with glass beads for better suspension and plated on BHI agar. The numbers of surviving colonies after incubation at 37° C. for 24 h are plotted. In FIGS. 6C-6D, the bars denote mean values for data from three biological replicates. *, significantly different (p, 0.002), **, significantly different (p, 0.02), according to Tukey test (Minitab 16 statistical software).

Figure 7A:
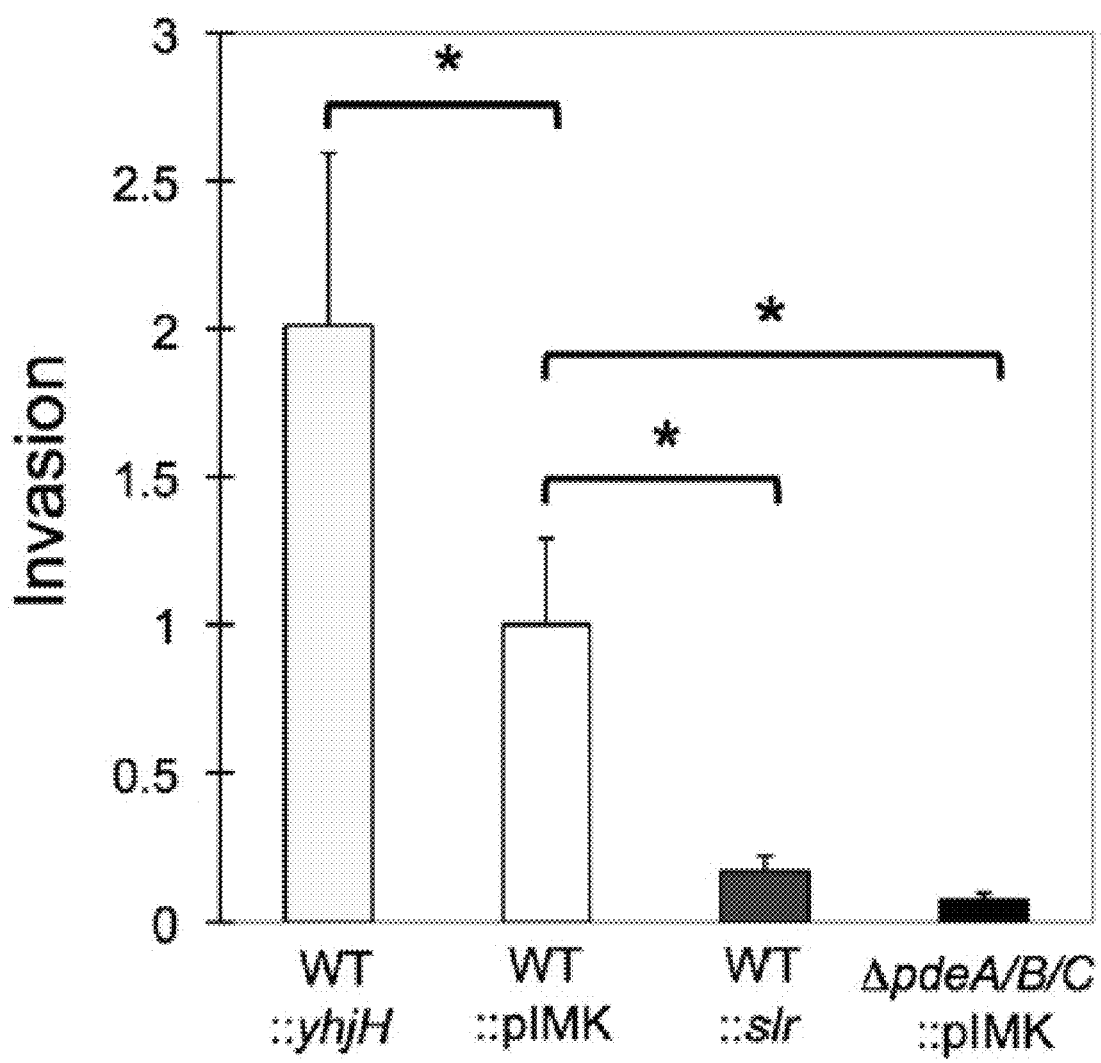
Figure 7B:
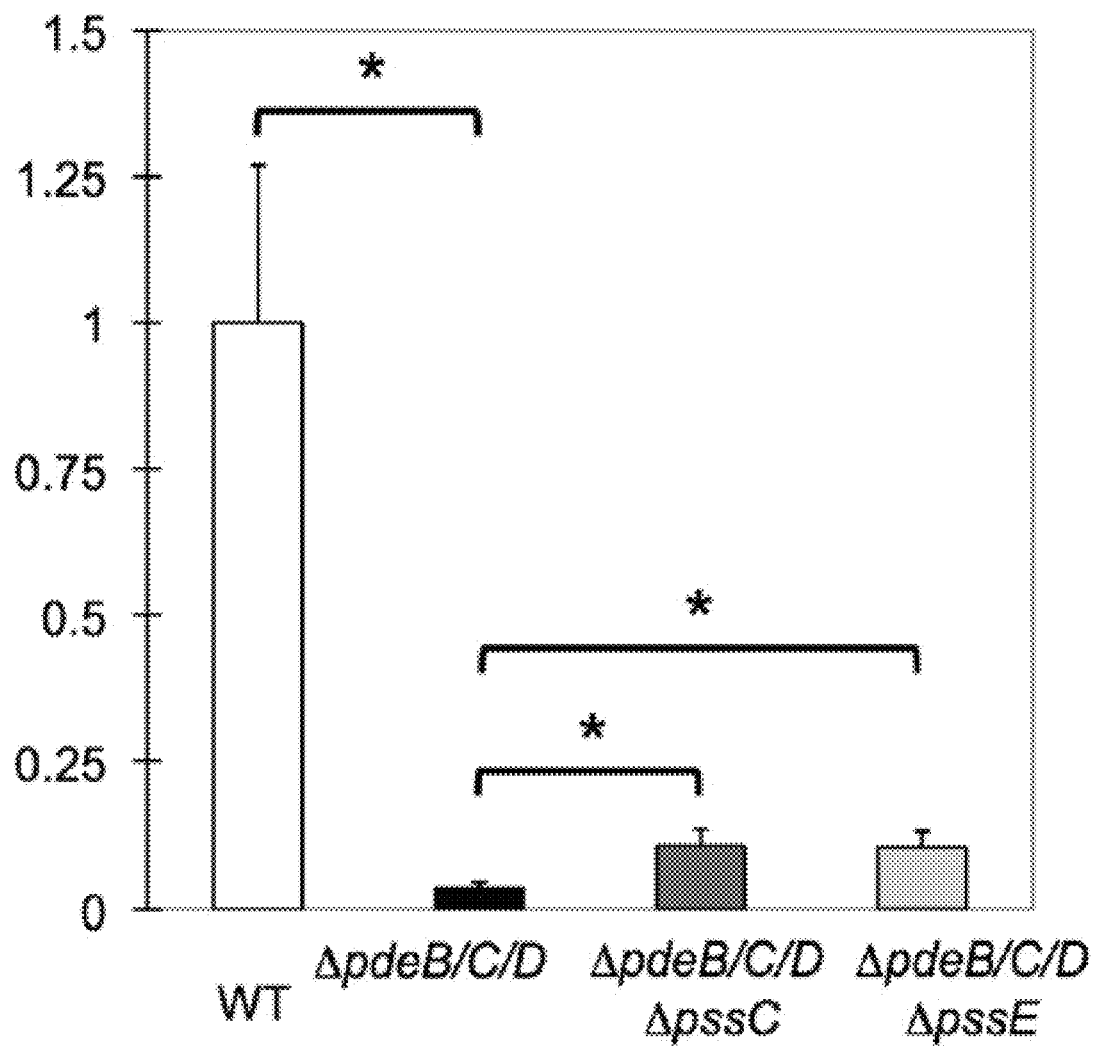

FIGS. 7A-7B: Impaired invasion of *L. monocytogenes* in HT-29 human colon adenocarcinoma cells by elevated c-di-GMP levels. FIG. 7A shows expression of the heterologous DGC, Slr1143 (WT::slr; blue bar), or deletion of the native PDEs (ΔpdeB/C/D; black), strongly inhibit listerial invasion, compared to EGD-e containing an empty vector (WT::pIMK; white), while overexpression of the heterologous PDE, YhjH (WT::yhjH; yellow), improves invasion. FIG. 7B shows high intracellular c-di-GMP levels inhibit invasion more significantly than the presence of EPS. Strains shown are WT (white bar); ΔpdeB/C/D mutant (black); ΔpdeB/C/D ΔpssC (dark-grey), and ΔpdeB/C/D ΔpssE (light-grey). Plotted are values of relative invasion, compared to those of WT::pIMK (FIG. 7A) or WT (FIG. 7B). Average results from three independent tests, each performed in three replicates are shown. *, significantly different (p, 0.001). Prism 5 for Mac (GraphPad) was used to perform unpaired Student's t-tests.

Figure 8:
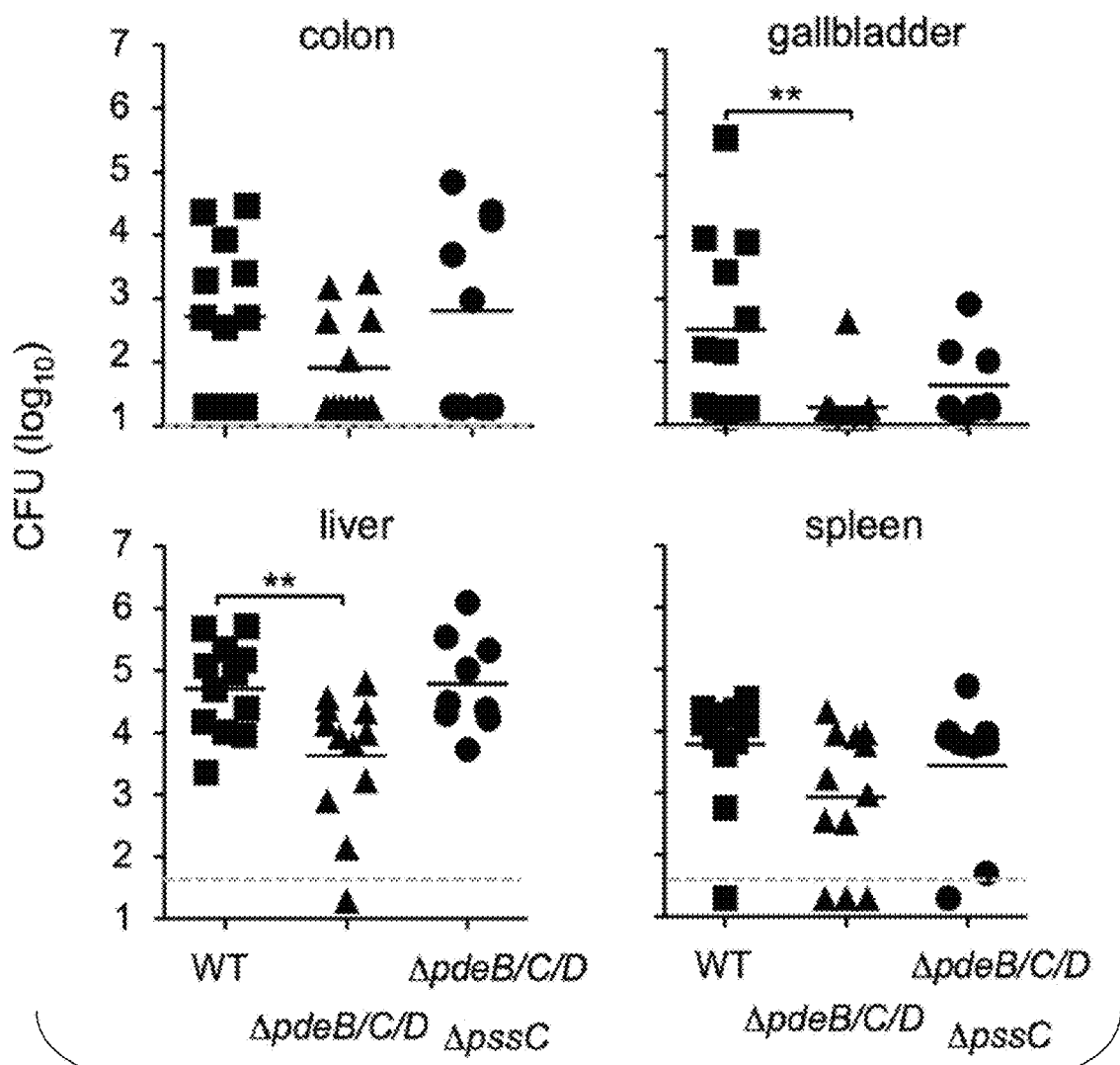

FIG. 8: Impaired spreading of the *L. monocytogenes* ΔpdeB/C/D mutant to the liver and gallbladder in a food-borne model of infection. Groups of BALB/c/By/J mice were fed $5.9-7.5 \times 10^8$ CFU of the indicated *L. monocytogenes* strains and bacterial loads were assessed 60 h post-infection. Dashed lines indicate the limit of detection for each tissue. Bars denote mean values for pooled data from three separate experiments. **, significantly different (p, 0.05). Prism 5 for Mac (GraphPad) was used to perform unpaired Student's t-tests.

Figure 9A:
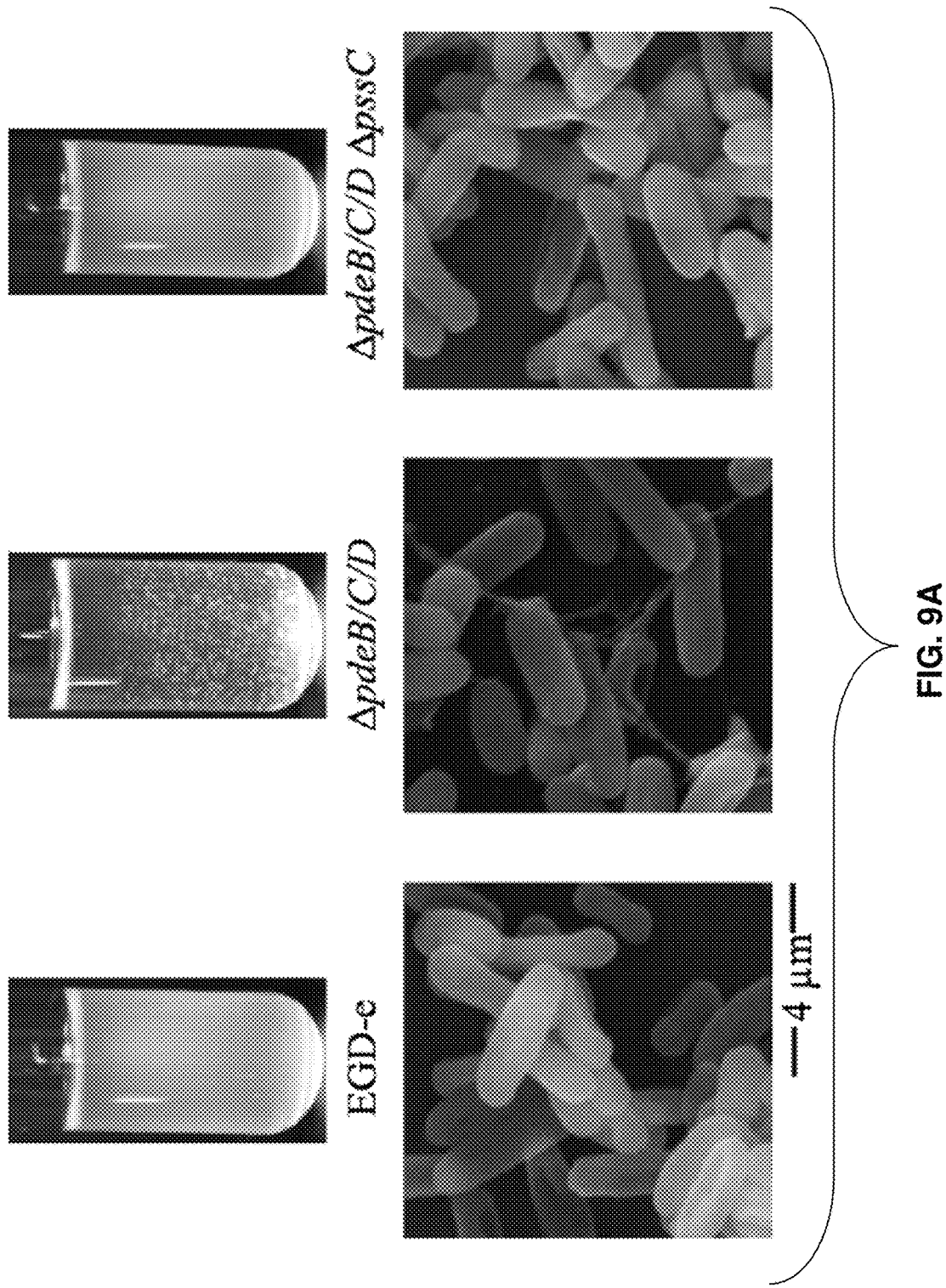
Figure 9B:
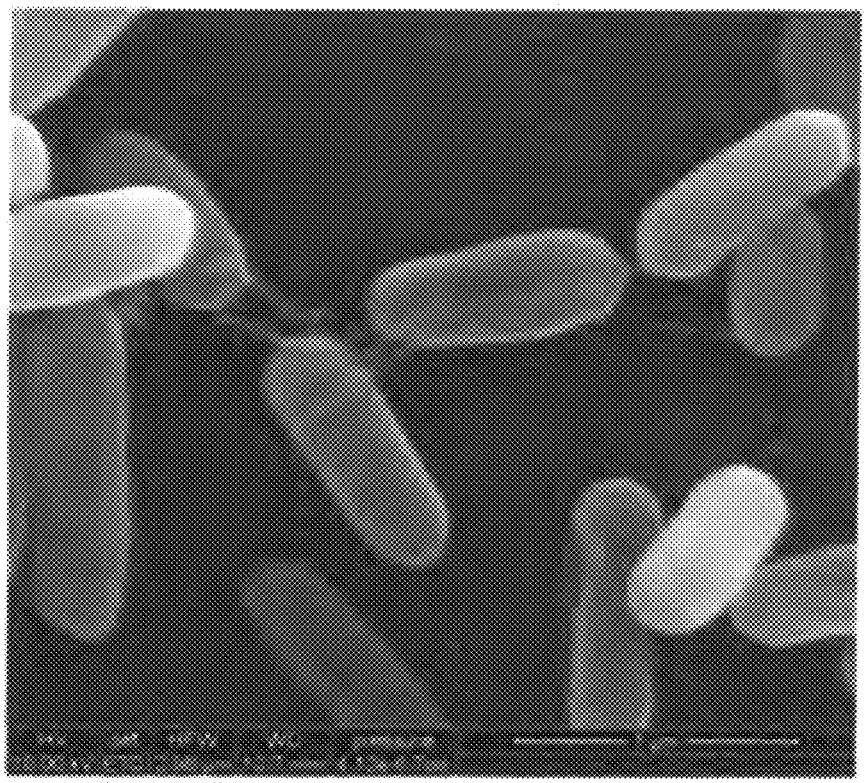
Figure 9C:
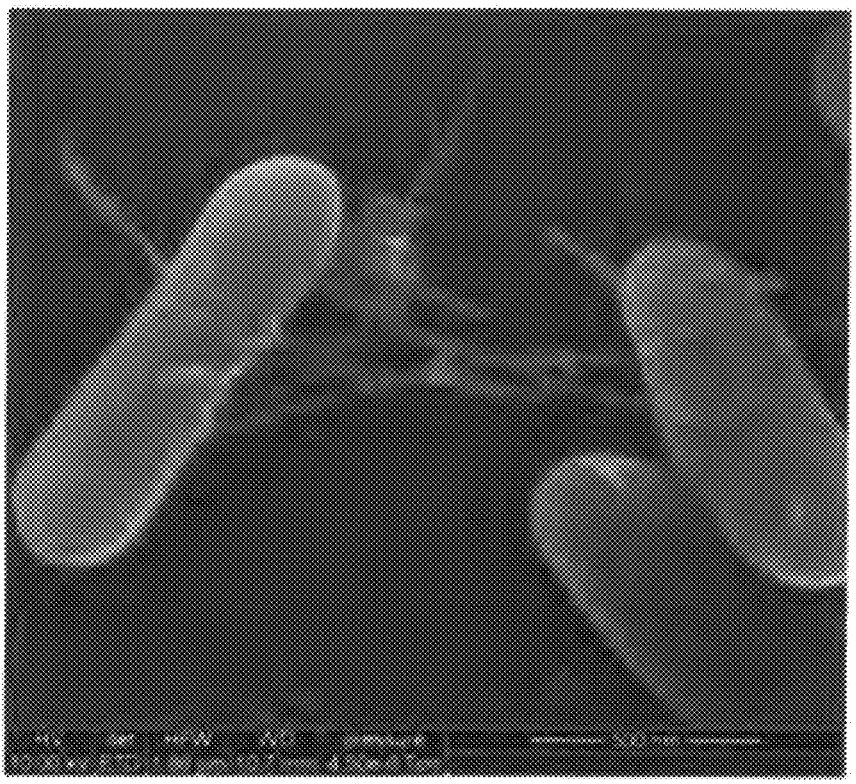

FIGS. 9A-9C: Cell aggregation in HTM/G medium and scanning electron microscopy (SEM) images of corresponding cultures. Top row in FIG. 9A: the EPS overproducing ΔpdeB/C/D strain grows in clumps in HTM/G medium at 30° C. after 48 h whereas the wilde-type (EGD-e) and ΔpdeB/C/D ΔpssC strains are not aggregated. Bottom row in FIG. 9A: SEM images of the cultures from the top row. FIGS. 9B-9C show SEM images of cell-bound intercellular adhesive listerial ManNAc-Gal EPS. These images were taken from the same culture of the ΔpdeB/C/D strain shown in FIG. 9A.

Figure 10A:
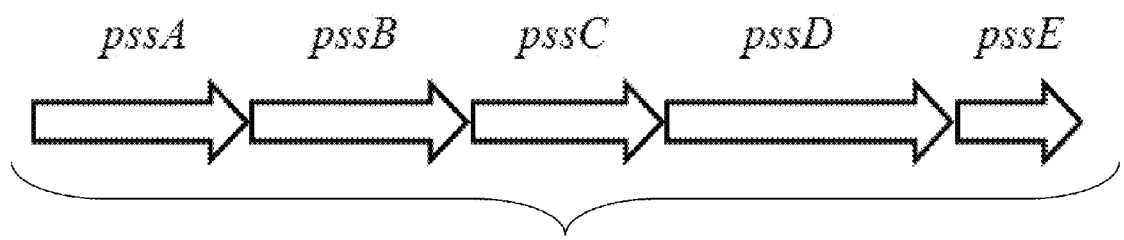
Figure 10B:
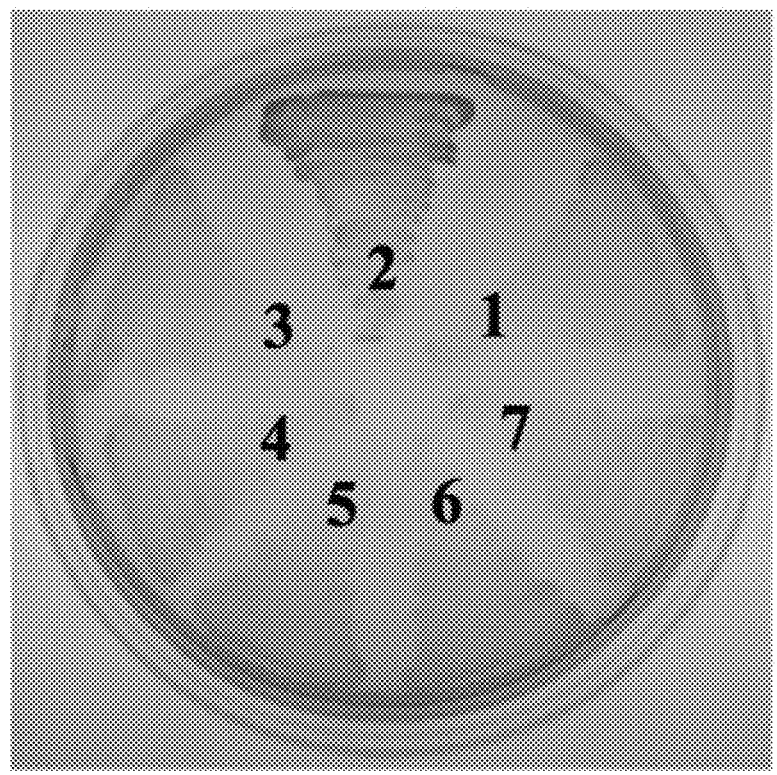
Figure 10C:
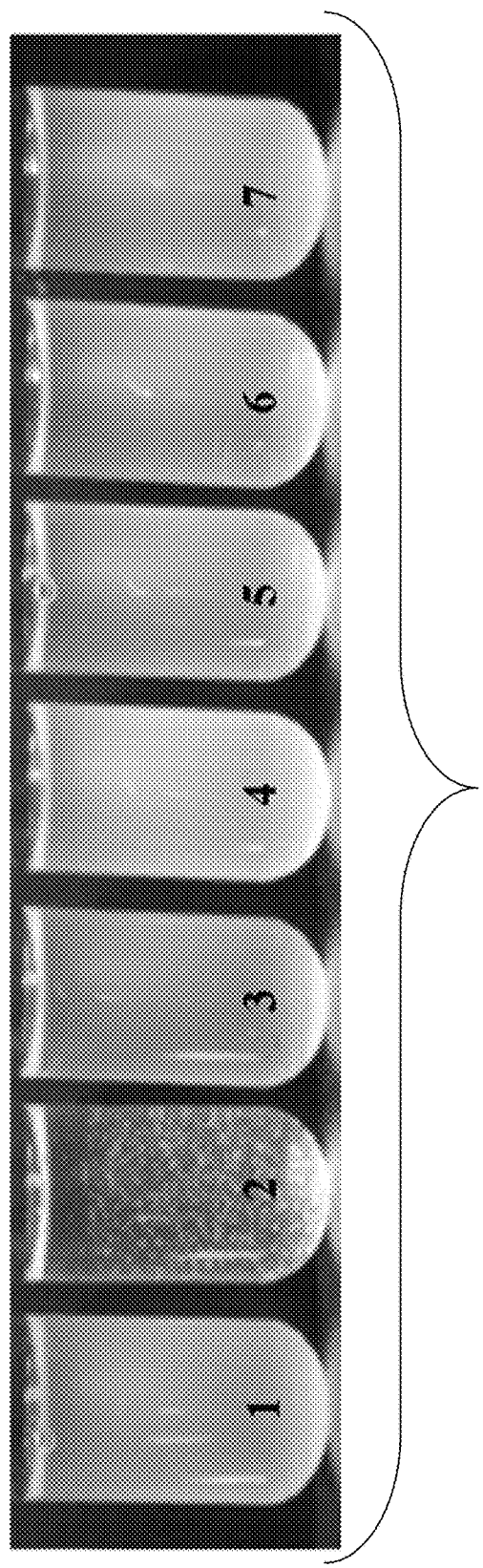

FIGS. 10A-10C: Phenotypic analysis of mutants in EPS biosynthesis. FIG. 10A shows a map of the pssA-E operon (lmo0527-lmo0531). FIG. 10B shows a Congo red binding assay of the ΔpdeB/C/D strain containing deletions in the pss operon. Cells were grown on HTM/G agar supplemented with 40 μg mL-1 Congo red dye at 30° C. for 48 h. FIG. 10C shows a cell aggregation assay of the ΔpdeB/C/D strain containing deletions in the pss operon. Cells were grown in HTM/G liquid medium at 30° C. for 48 h. Strain designation in FIGS. 10B and 10C: 1, EGD-e; 2, ΔpdeB/C/D; 3, ΔpdeB/C/D ΔpssE; 4, ΔpdeB/C/D ΔpssD; 5, ΔpdeB/C/D ΔpssC; 6, ΔpdeB/C/D ΔpssB; 7, ΔpdeB/C/D ΔpssA.

Figure 11A:
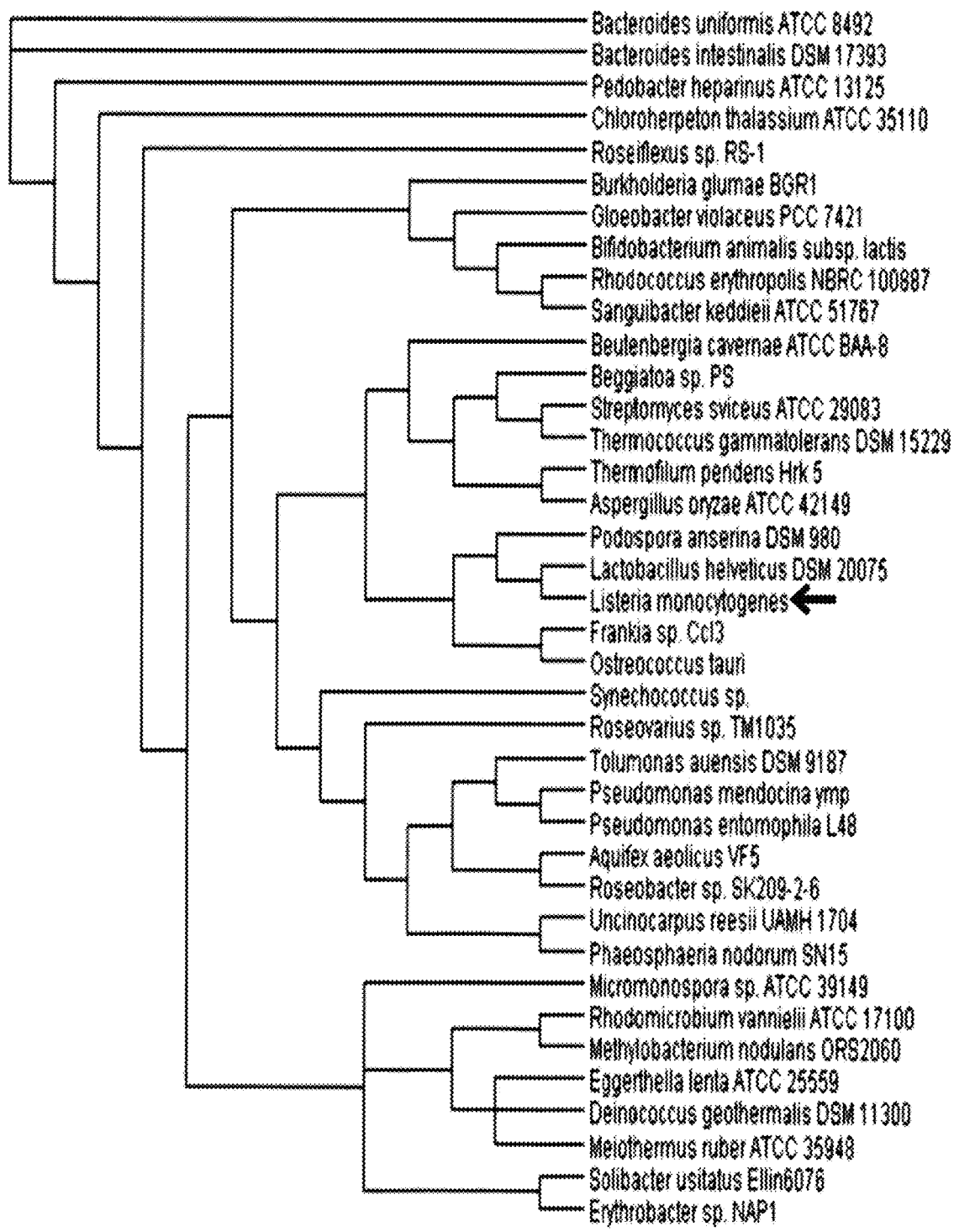
Figure 11B:
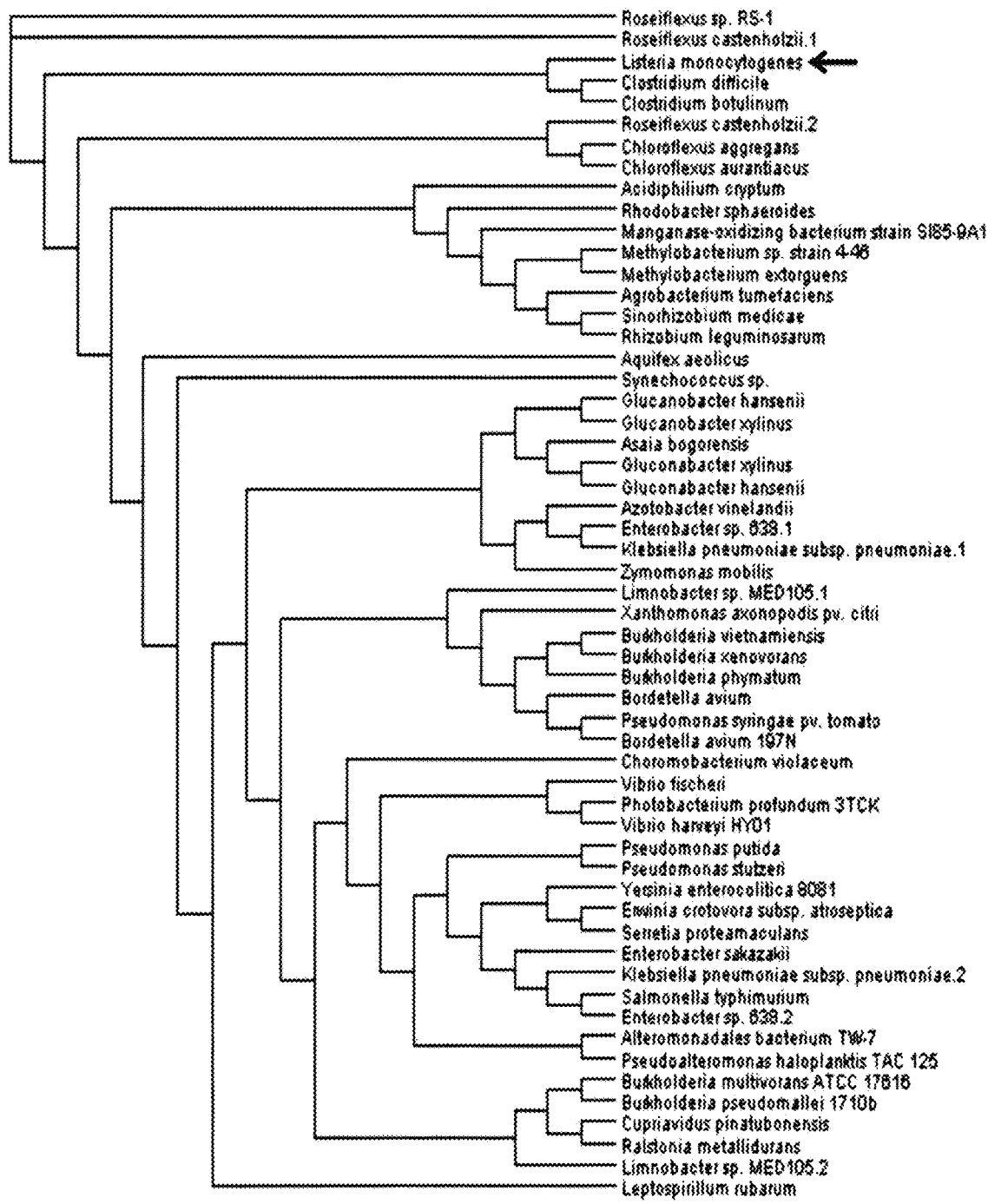
Figure 11C:
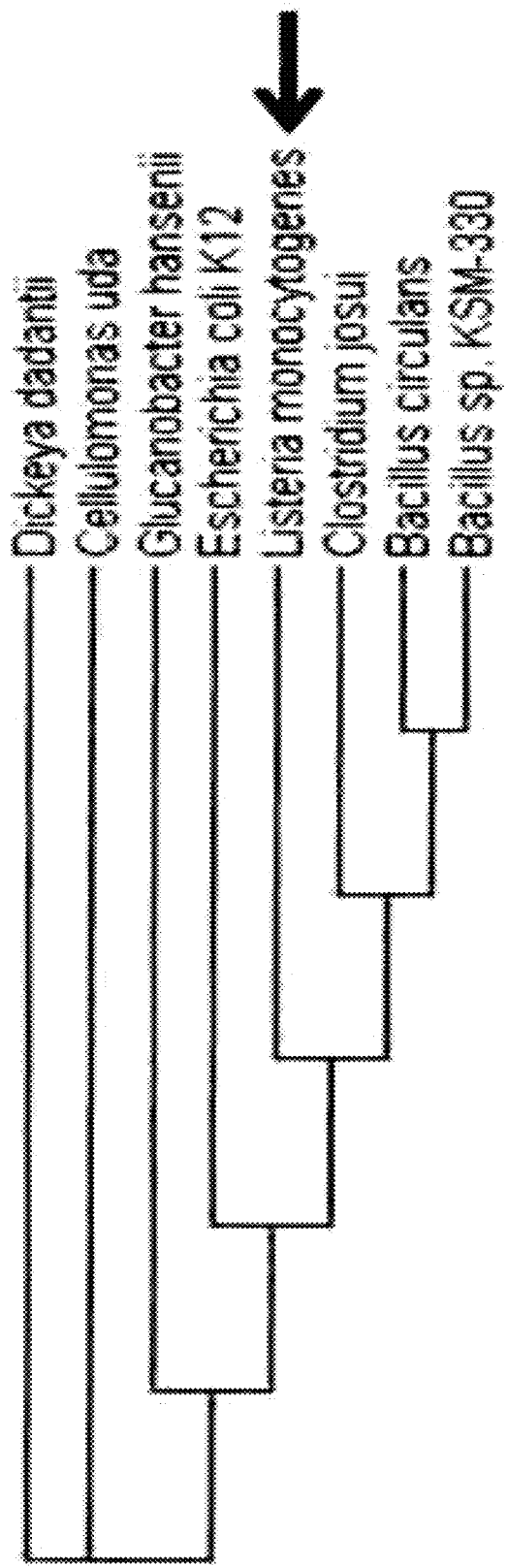

FIGS. 11A-11C: Phylogenetic tree analysis of proteins involved in listerial ManNAc-Gal EPS biosynthesis. FIG. 11A shows a phylogenetic tree constructed with *L. monocytogenes* PssC and glycosyl transferase family 2-3 proteins (seed alignment in Pfam). FIG. 11B shows a phylogenetic tree constructed with *L. monocytogenes* PssD and BcsB domain proteins. FIG. 11C shows a phylogenetic tree constructed with *L. monocytogenes* PssZ and glycosyl hydrolase family 8 (GH8) proteins.

Figure 12:
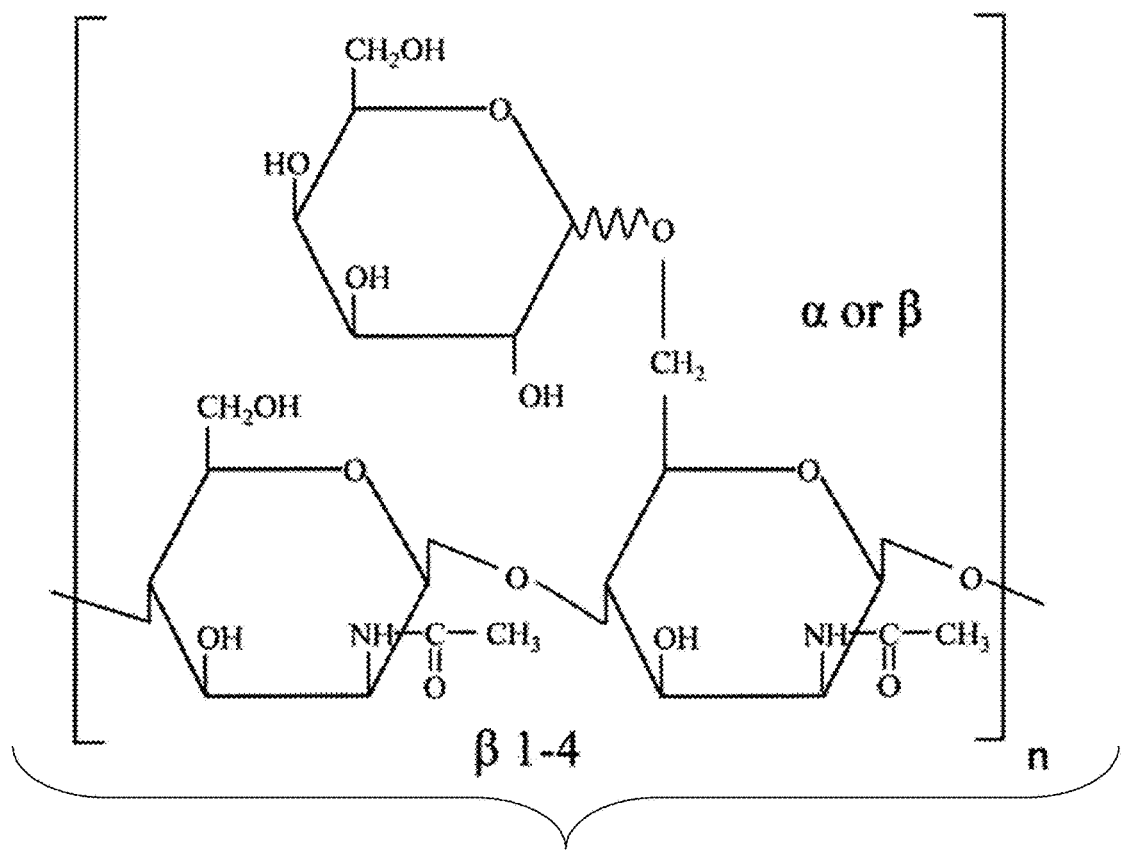

FIG. 12: Repeating unit structure of listerial ManNAc-Gal EPS. Shown is a polymer of β1-4 linked ManNAc residues containing Gal branches attached via an α or β configuration.

Figure 13A:
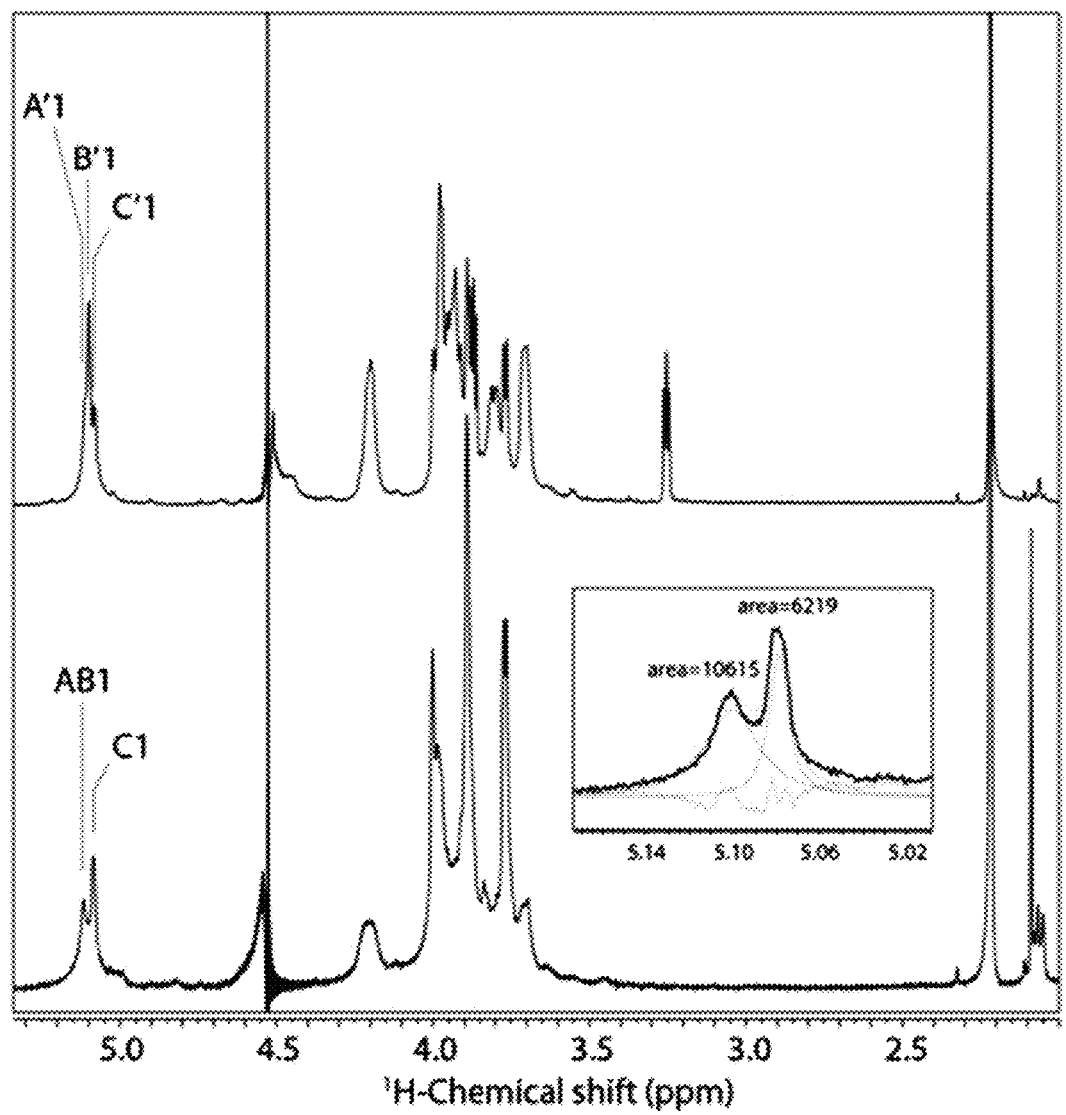
Figure 13B:
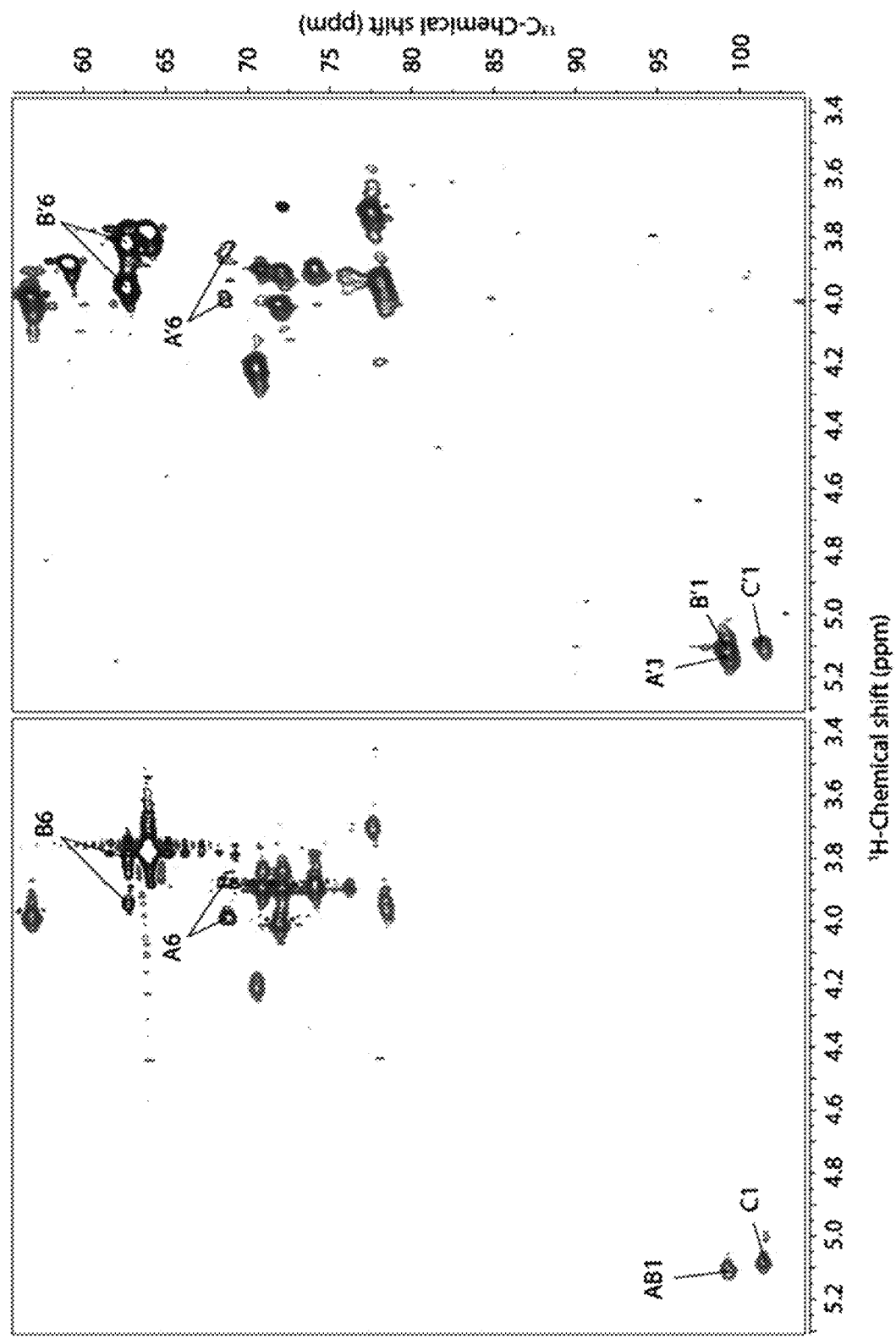
Figure 13C:
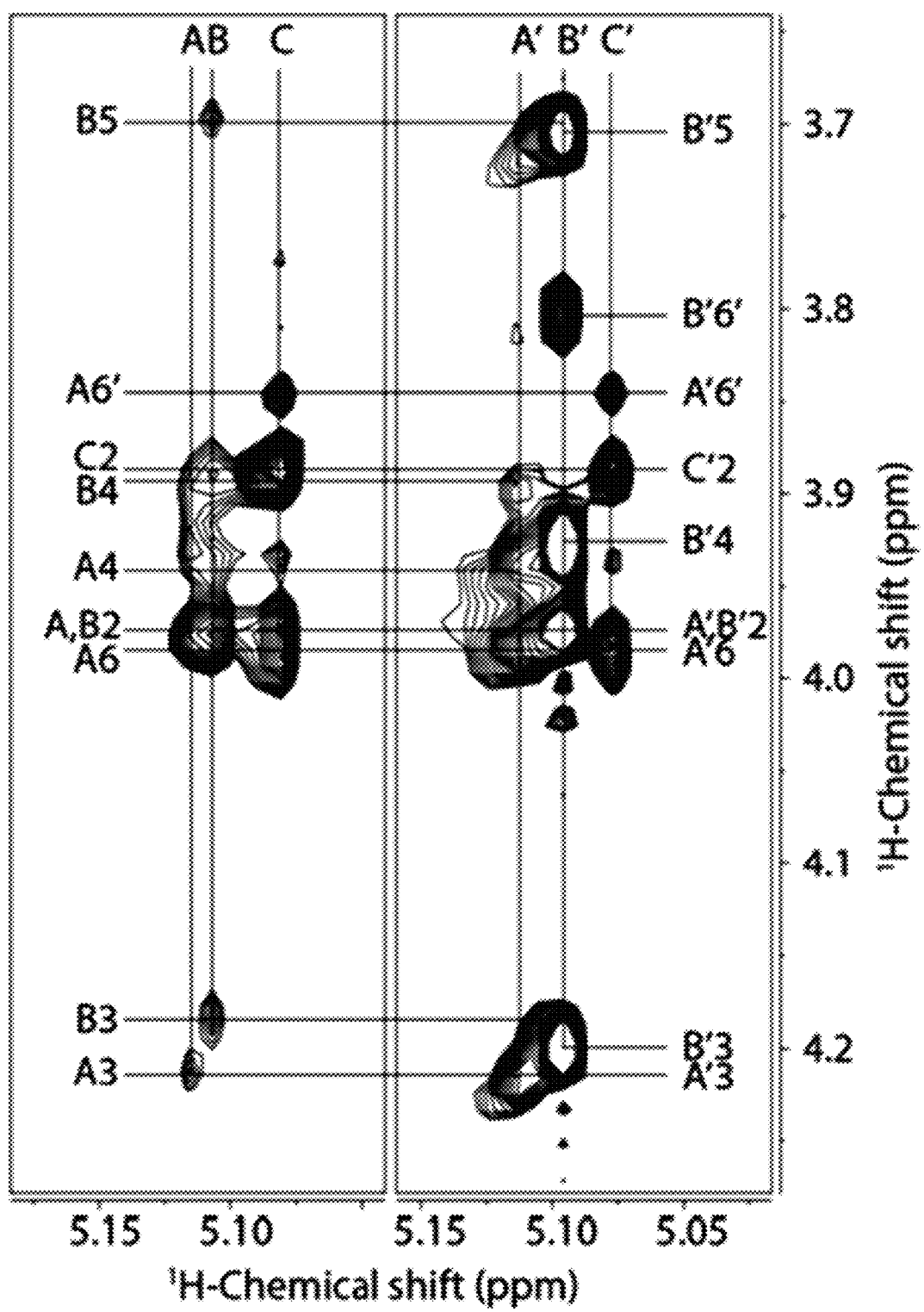

FIGS. 13A-13C: Structural analysis of listerial ManNAc-Gal EPS. FIG. 13A shows the 1-D proton NMR spectrum of EPS-N (bottom) and EPS-H (top). The ManN anomeric signal in EPS-N appears smaller than the Gal anomeric signal. This is because it has significantly greater linewidth, as shown in the inset. Deconvolution and integration of the two signals shows that the intensity of the ManN peak is about twice that of the Gal peak. Blue lines are the fitted peaks, the green line is the sum curve, and the red line is the residue curve. FIG. 13B shows a multiplicity-edited 2D $^1$H-$_{13}$C-HSQC NMR spectra of EPS-N (left) and EPS-H (right). Multiplicity-editing causes signals from methyl and methane groups to be positive (red) and signals from methylene groups to be negative (blue). FIG. 13C shows a portion of the NOESY spectra of EPS-N (left) and EPS-H (right). Labeling in all panels refers to Table 2.

Figure 14:
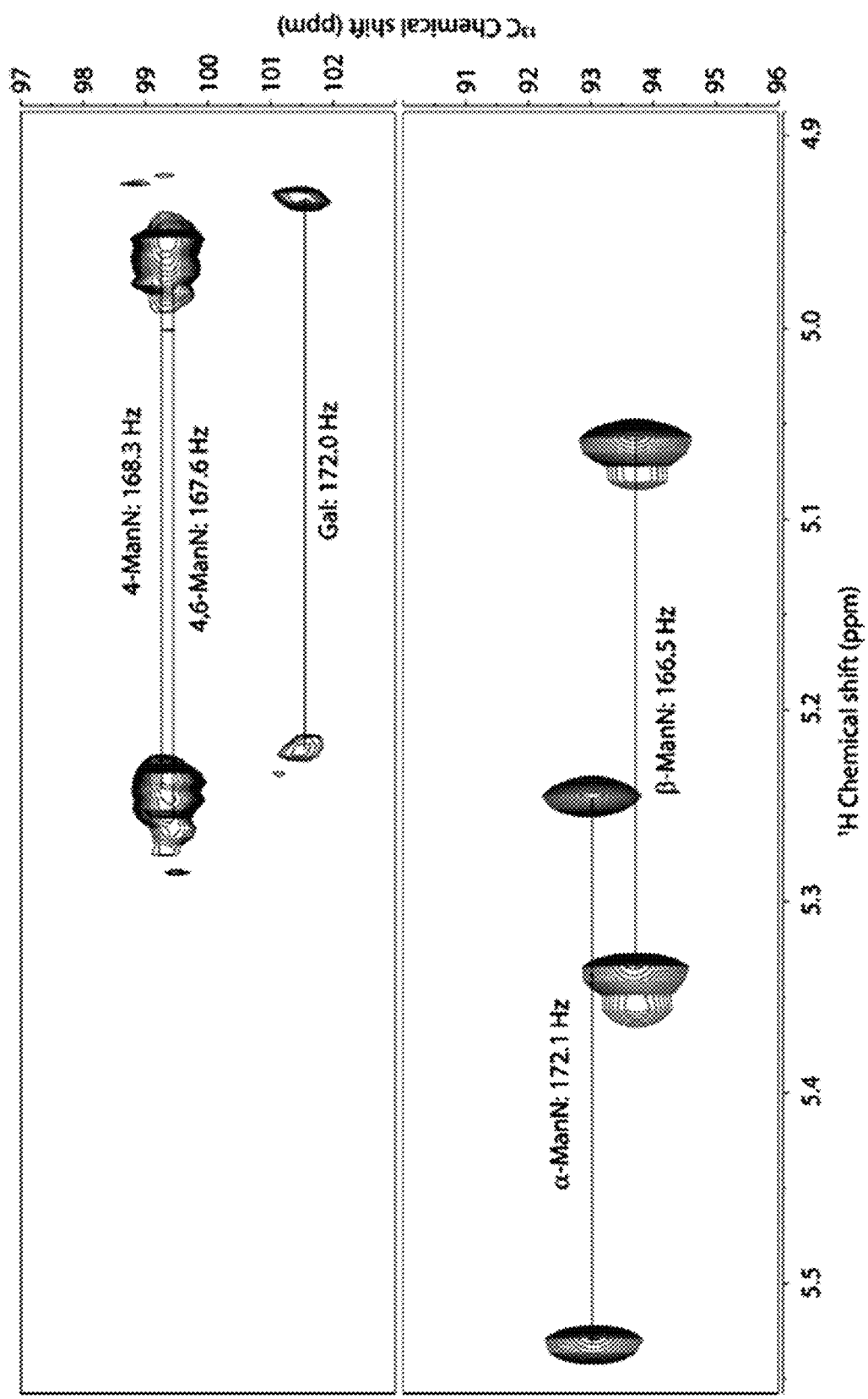

FIG. 14: Anomeric region of the HSQC spetra. Top: EPS-H. Bottom: mannosamine hydrochloride. HSQC spectra were obtained without decoupling during acquisition for the measurements of one-bond C—H coupling constants.

Figure 15A:
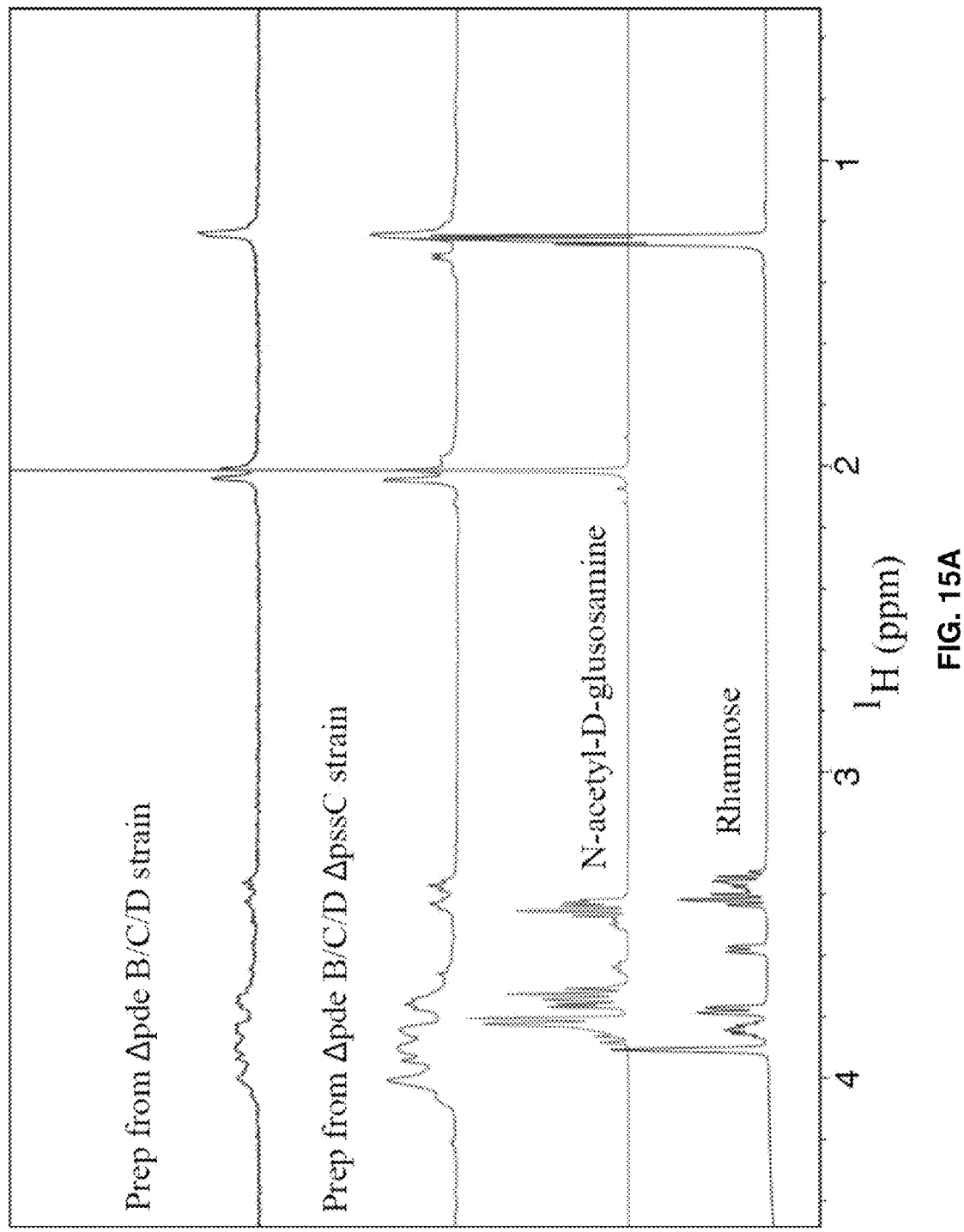
Figure 15B:
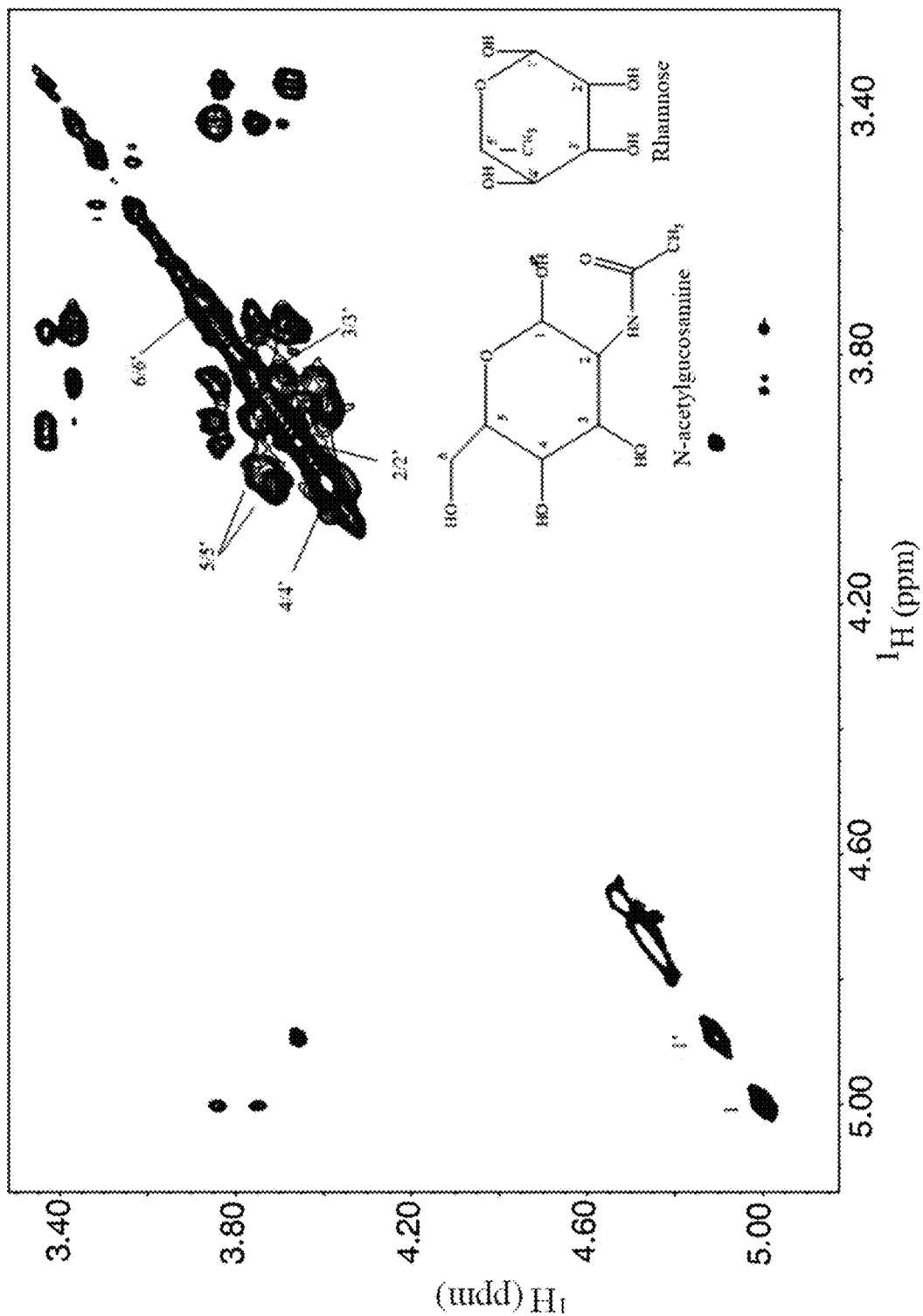
Figure 15C:
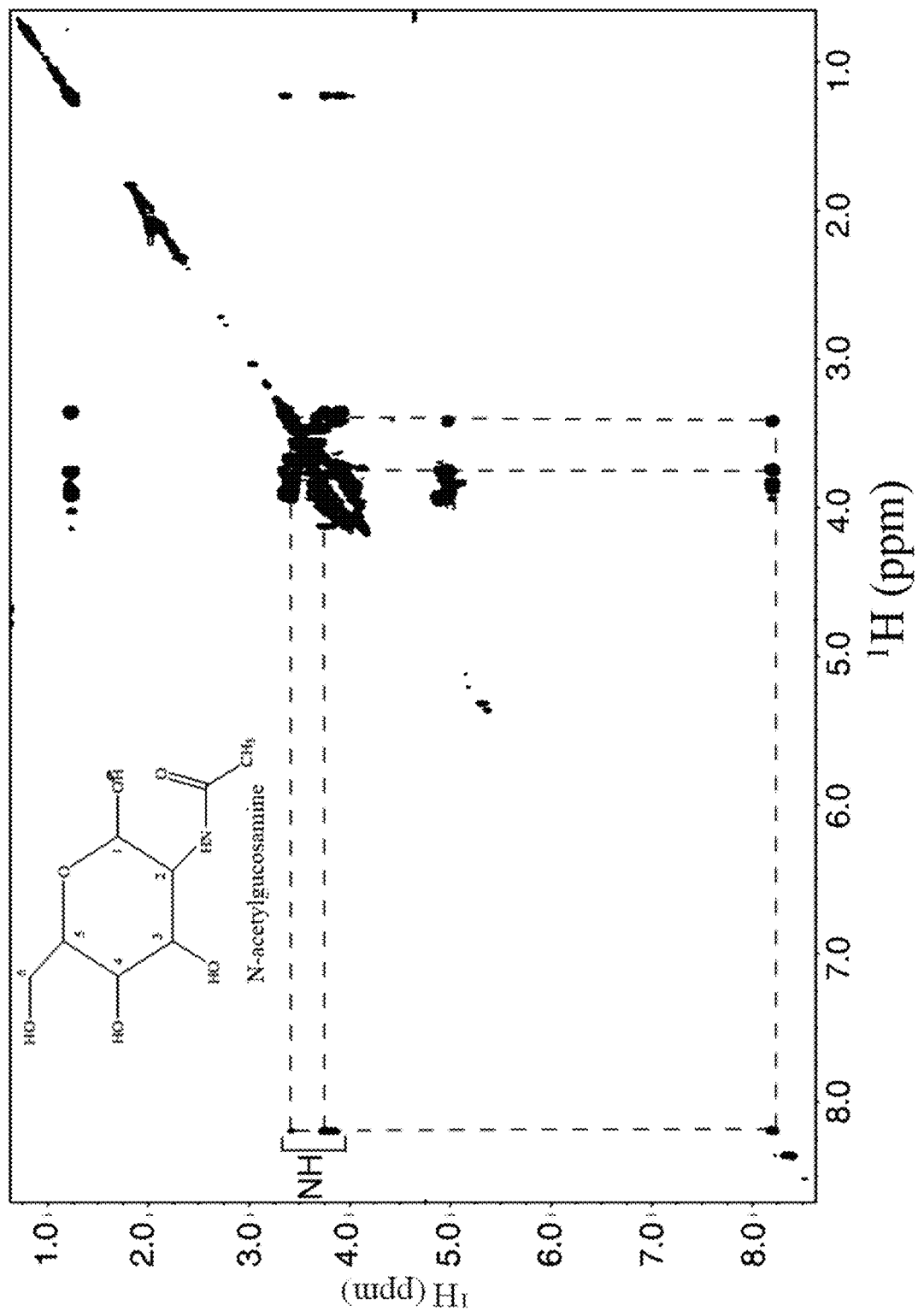
Figure 15D:
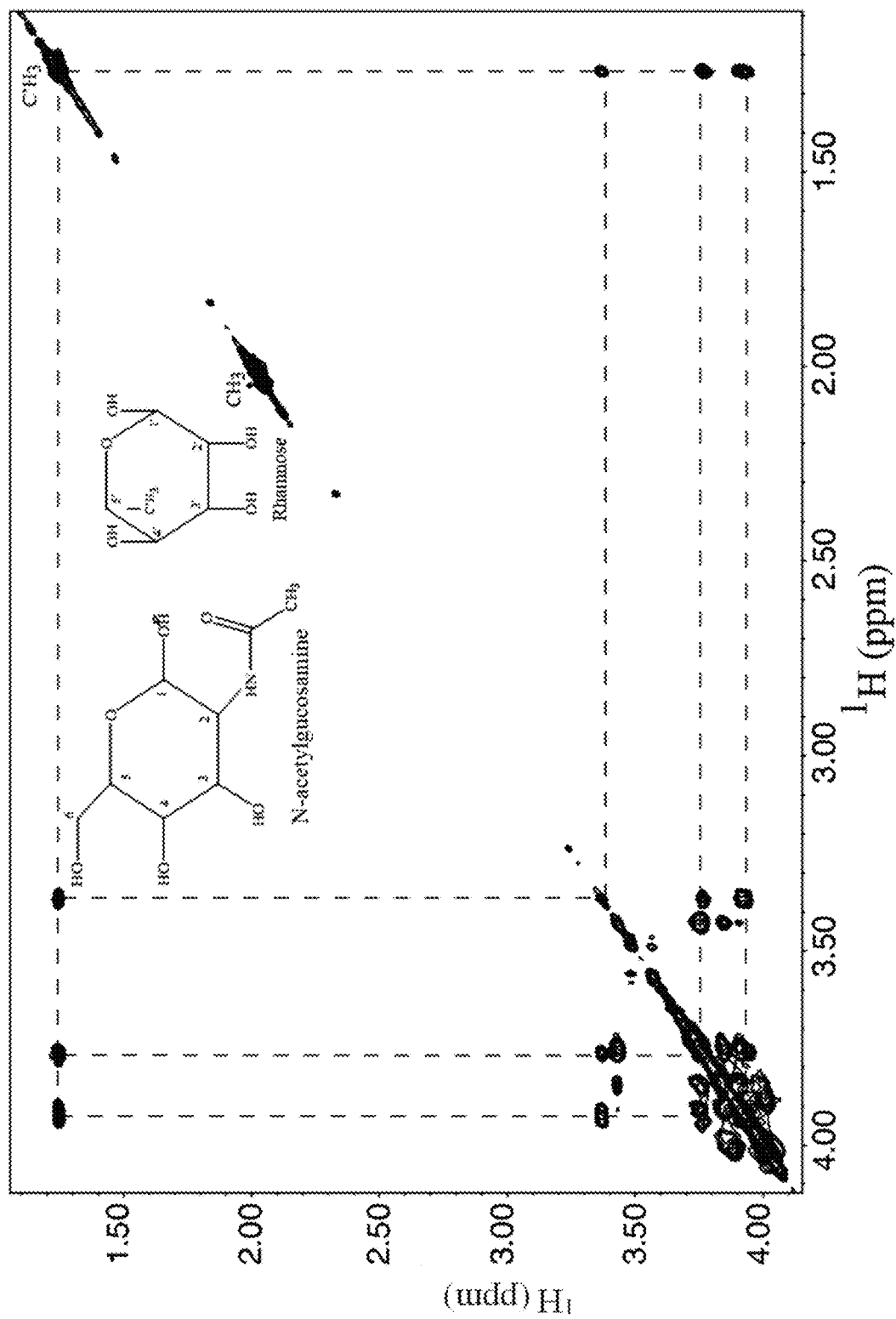

FIGS. 15A-15D: Structures of secreted *L. monocytogenes* carbohydrates. FIG. 15A shows 1D $^1$H-NMR spetra of the soluble carbohydrate preparations from the ΔpdeB/C/D and ΔpdeB/C/D ΔpssC strains compared to those of pure standard samples of N-acetyl-D-glucosamine and rhamnose. These spectra show how the peak patterns of the standard samples fit well with those of the strain samples. FIG. 15B shows a 2D $^1$H-TOCSY spectrum at 298 K (5.10-3.30 ppm region) of the soluble carbohydrate prep from the ΔpdeB/C/D strain showing the assignments for sugar protons. The signals at 5.00 and 4.90 ppm are assigned to the anomeric protons (H1 and H1') of N-acetylglucosamine and rhamnose, respectively. The signals of protons 2/2', 3/3', and 5'/5' overlap for both sugar molecules due to the similarities in their chemical structures. FIG. 15C shows a 2D $^1$H-TOCSY spectrum of the soluble carbohydrate prep from the ΔpdeB/C/D strain in H$_2$O at 298 K displaying the connectivities of the NH proton in N-acetylglucosamine. FIG. 15D shows a 2D $^1$H-TOCSY spectrum of the soluble carbohydrate prep from the ΔpdeB/C/D strain in D$_2$O at 298 K indicating the presence of the CH$_3$ groups in N-acetylglucosamine and rhamnose. The CH$_3$ protons in rhamnose (C'H$_3$) exhibit several cross-connectivities with the body of this sugar. On the other hand, the CH$_3$ group protons in N-acetylglucosamine show no connectivities due to its attachment to a quarternary carbon atom.

Figure 16A:
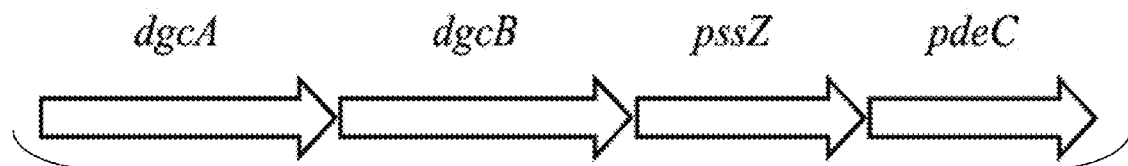
Figure 16B:
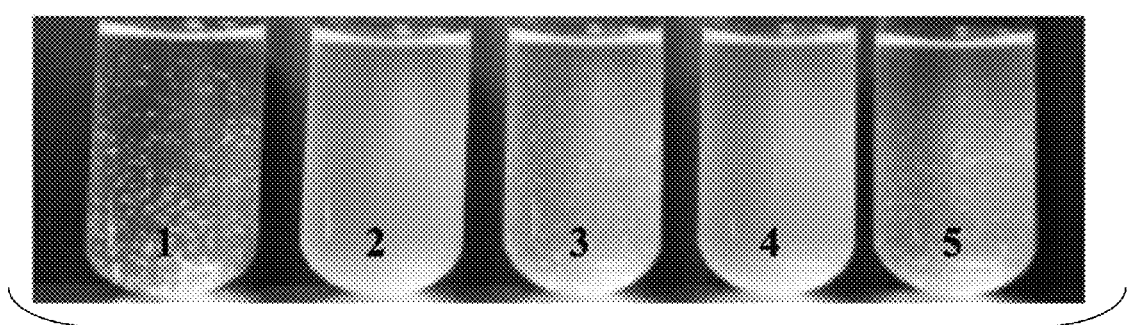
Figure 16C:
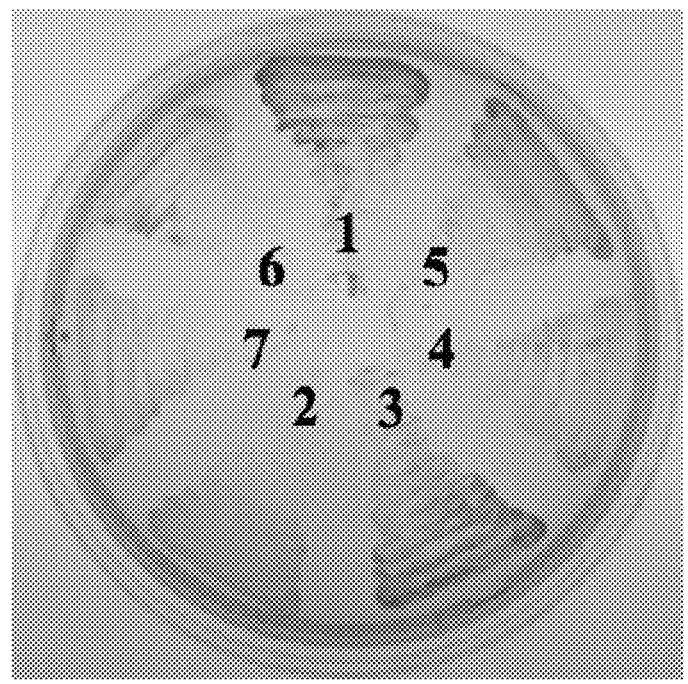
Figure 16D:
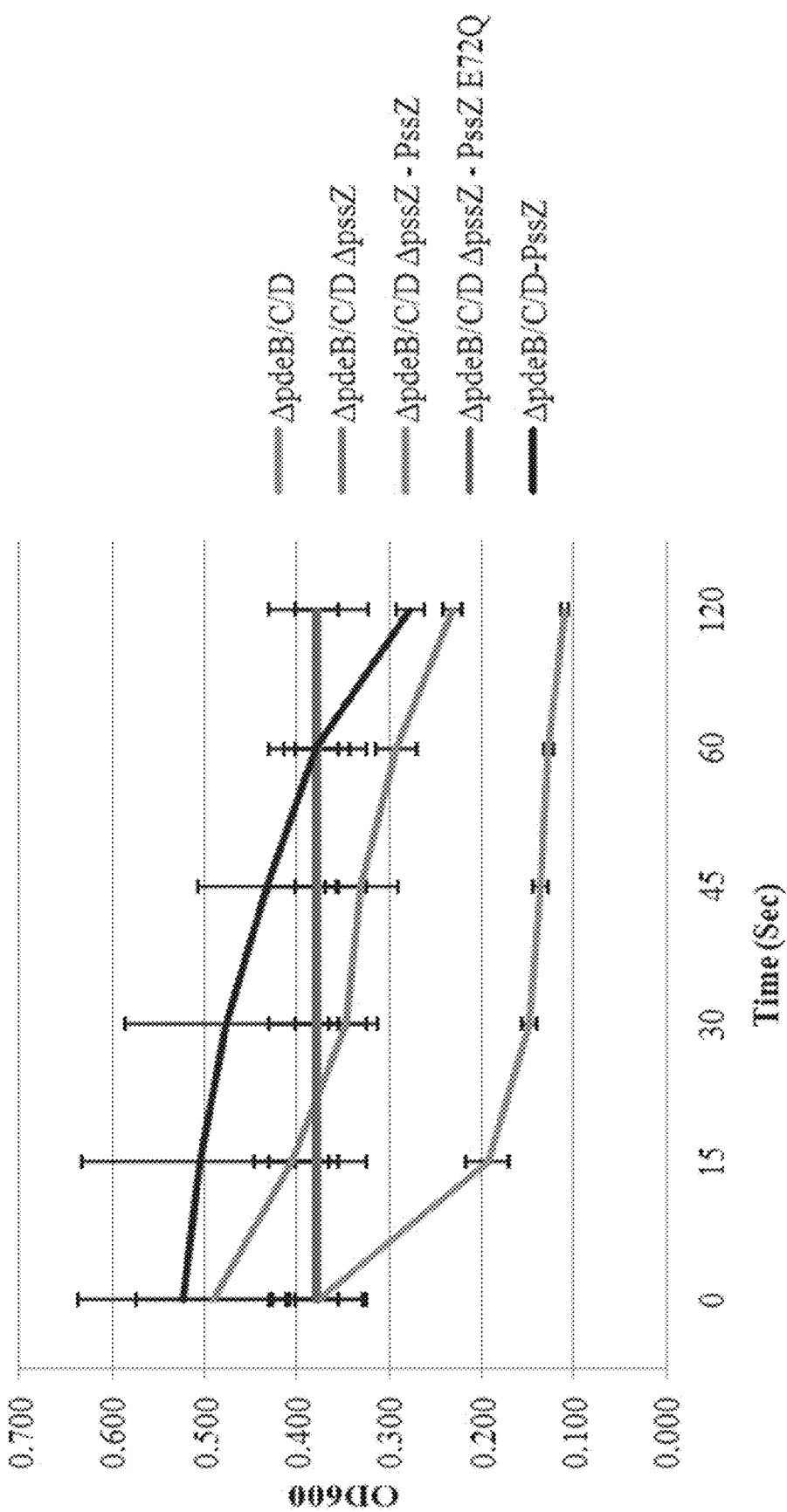

FIGS. 16A-16D: Phenotypic analysis of mutants in EPS degradation. FIG. 16A shows a map of the dgcA-dgcB-pssZ-pdeC (lmo1911-lmo1914) gene cluster. FIG. 16B shows a Congo red binding assay of strains with deleted or overexpressed pssZ genes. FIG. 16C shows a cell aggregation assay of strains with deleted or overexpressed pssZ genes. Strain designation in FIGS. 16B-16C: 1, ΔpdeB/C/D; 2, ΔpdeB/C/D ΔpssZ; 3, ΔpdeB/C/D ΔpssZ pIMK2-pssZ; 4, ΔpdeB/C/D ΔpssZ pIMK2-pssZ E72Q; 5, ΔpdeB/C/D pIMK2-pssZ; 6, EGD-e; 7, ΔpdeB/C/D ΔpssC. Note that only strains 1-5 were analyzed in FIG. 16C. FIG. 16D shows aggregation of strains with deleted or overexpressed pssZ genes assessed by drop in optical density. The drop in the optical density correlates with the degree of cell aggregation. Data are derived from two independent biological repeats each with three measurements. Note that the red and purple lines are superimposed.

Figure 17A:
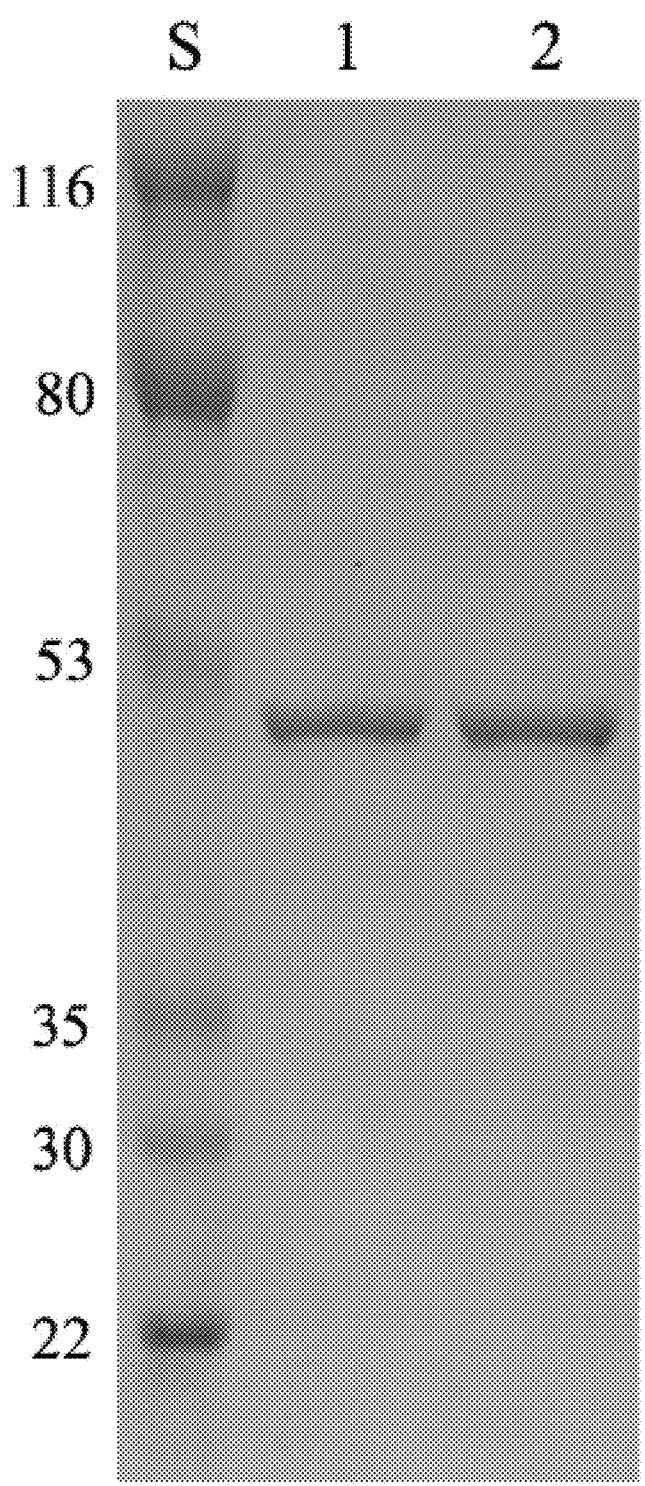

FIGS. 17A-17D: ManNAc-Gal EPS-specific glycosylhydrolase activity of purified PssZ. FIG. 17A shows SDS-PAGE of purified recombinant proteins. S, protein standards; lane 1, PssZ E72Q; lane 2, PssZ. Molecular weights of protein standards are given in kDa. FIG. 17B shows alignment of PssZ proteins (residues 48-159) with the HMM alignment for GH8 family proteins. The active site Glu72 conserved in GH8 proteins is shown in red. This residue was substituted with glutamine in the PssZ E72Q mutant. Other conserved residues are indicated in blue. #HMM, consensus of the Hidden Markov Model (HMM) (SEQ ID NO: 62); #MATCH, the match between the query sequence and the HMM; #PP, posterior probability (a degree of certainty for each aligned residue, i.e., asterisk indicates the highest certainty). #Lin, *L. innocua* Lin2027 (SEQ ID NO: 63); #Lmo, *L. monocytogenes* PssZ (Lmo 1913) (SEQ ID NO: 64). Note: the alignment is divided into two parts for the ease of illustration. FIG. 17C shows a cell aggregation assay with the ΔpdeB/C/D strain in the presence of PssZ and PssZ E72Q. Cells were grown in HTM/G at 30° C. for 24 h in the presence of added recombinant proteins. Protein concentrations: panel 1, 0.13 µg mL$^{-1}$; panel 2, 1.3 µg mL$^{-1}$. FIG. 17D shows dispersal of preformed aggregates with PssZ. Proteins were added at 32 µg mL$^{-1}$ (final concentration) to the washed aggregates of strain ΔpdeB/C/D and incubated with gentle shaking in HTM salts (no glucose) for 6 h at 30° C.

Figure 18A:
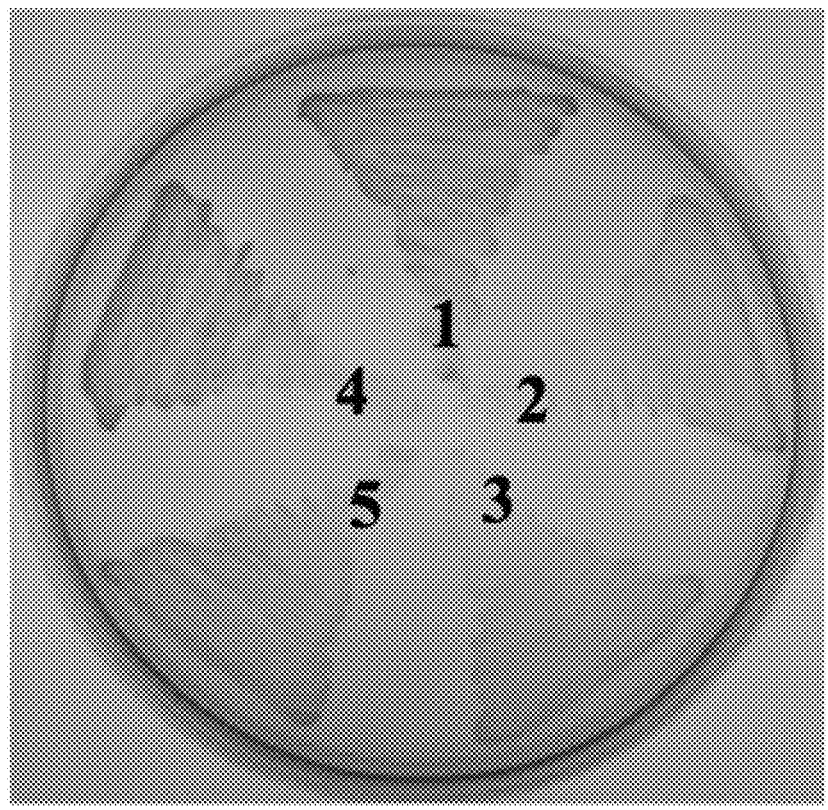
Figure 18B:
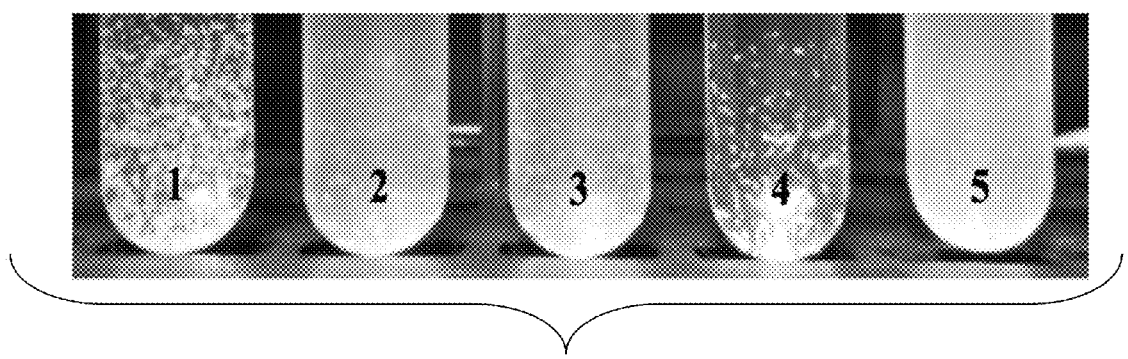
Figure 18C:
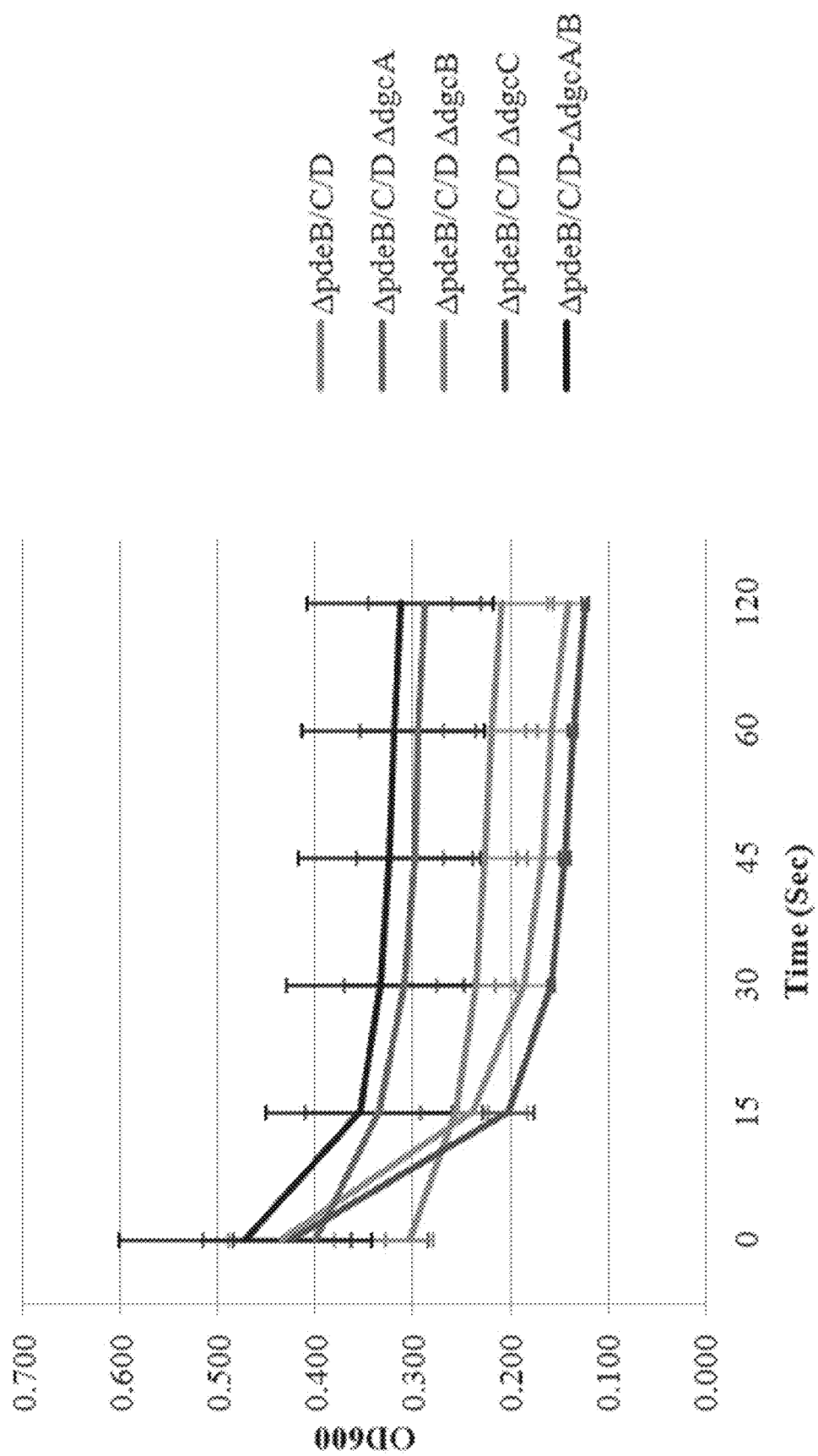

FIGS. 18A-18B: Diguanylate cyclases (DGCs), DgcA and DgcB, control ManNAc-Gal EPS synthesis in *L. monocytogenes*. FIG. 18A shows a Congo red binding assay with ΔpdeB/C/D strains with in-frame deletions in the DGC genes. FIG. 18B shows a cell aggregation assay with ΔpdeB/C/D strains with in-frame deletions in the DGC genes. 1, ΔpdeB/C/D; 2, ΔpdeB/C/D ΔdgcA; 3, ΔpdeB/C/D ΔdgcB; 4, ΔpdeB/C/D ΔdgcC; 5, ΔpdeB/C/D ΔdgcA/B. FIG. 18C shows aggregation of ΔpdeB/C/D strains with in-frame deletions in the DGC genes assessed by drop in optical density. The drop in the optical density correlates with the degree of cell aggregation. Data are derived from two independent biological repeats each with three measurements.

Figure 19:
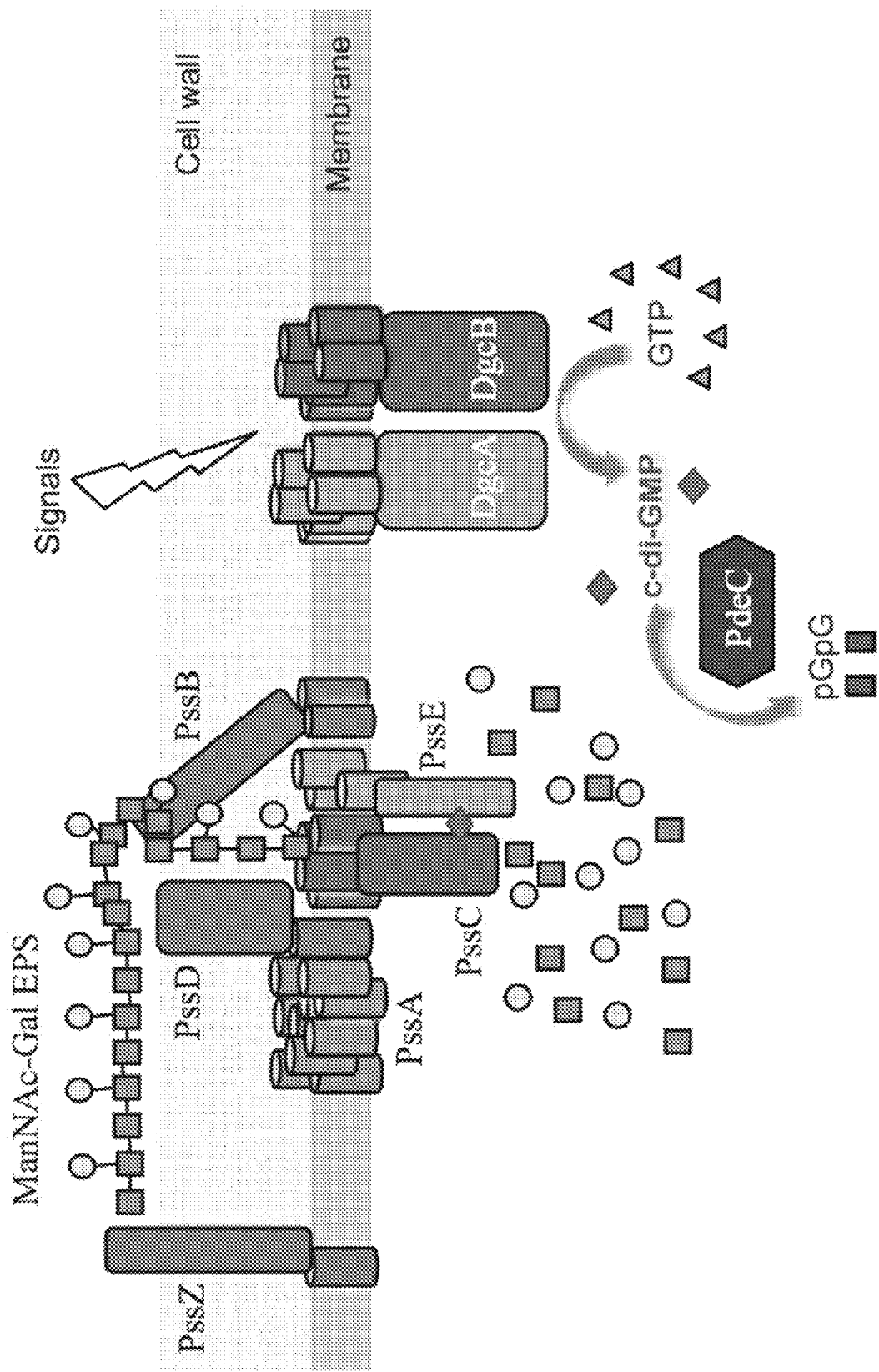

FIG. 19: Model for listerial c-di-GMP-regulated ManNAc-Gal EPS biosynthesis machinery. The signaling molecule c-di-GMP (red diamong) is synthesized from GTP by DGCs, DgcA, and DgcB. pGpG (p, phosphate; G, guanine) is the breakdown product of c-di-GMP hydrolysis by phosphodiesterase PdeC. Proteins involved in ManNAc-Gap EPS biosynthesis are depicted according to their predicted localizations. Barrels, protein transmembrane domains. Arrows indicate the reactions catalyzed by DgcA/B and PdeC proteins. Green squares, N-acetylmannosamine (ManNAc); yellow circles, galactose (Gal).

DETAILED DESCRIPTION OF THE INVENTION

Throughout this disclosure, various publications, patents, and published patent specifications may be referenced. The disclosures of these publications, patents, and published patent specifications are hereby incorporated by reference into the present disclosure to more fully describe materials and methods which may be used in conjunction with aspects of the described invention.

*Listeria monocytogenes* produces an N-acetylmannosamine (ManNAc)-based exopolysaccharide (EPS), also designated as the Pss EPS, that protects it against desiccation and commonly used disinfectants, including bleach and hydrogen peroxide. For example, exopolysaccharide-aggregated listerial cells show >10$^6$-fold higher survival rates when treated with bleach, compared to non-aggregated bacteria. In accordance with the present disclosure, the *L. monocytogenes* enzyme referred to herein as PssZ efficiently degrades listerial exopolysaccharide. The sequence of the gene and protein, as well as methods of recombinant PssZ purification from *E. coli*, and methods of using PssZ for the uses such as listerial aggregate disintegration and prevention of aggregation, are now described herein. The structure of the listerial ManNAc-based exopolysaccharide is unique. PssZ is the first enzyme that can degrade listerial exopolysaccharide.

The addition of recombinant PssZ to *L monocytogenes*-containing media prevents formation of exopolysaccharide-rich aggregates. Therefore, PssZ can be used, separately or in combination with disinfectants, to disintegrate bacterial exopolysaccharide-rich aggregates and increase the efficiency of disinfection. PssZ may also be used as a food additive to prevent formation of exopolysaccharide-rich aggregates in the foods prone to contamination by *L. monocytogenes* or other pathogenic bacteria producing ManNAc-based exopolysaccharide.

*L. monocytogenes* undergoes a transformation from a soil-borne bacterial saprophyte to a life-threatening intracellular pathogen. *L. monocytogenes* causes the food-borne disease listeriosis, which is a relatively rare and yet highly fatal disease with a mortality rate of 20-25%. It follows *Salmonella* as the second leading cause of death due to food-borne bacterial outbreaks in the USA, where the annual health costs associated with listeriosis are estimated to be ~$8.8 billion per year. In recent years, the listeriosis incidence rate has been increasing in the USA and Europe. The elderly, immunocompromised individuals, newborns, and pregnant women are at high risk for life-threatening listeriosis with variable clinical manifestations such as meningitis, sepsis, bacteremia, miscarriages and stillbirth. In healthy individuals, *L. monocytogenes* causes flu-like symptoms and gastroenteritis.

Listeriosis can occur after consumption of food products contaminated with relatively high numbers (approximately $10^6$) of *L. monocytogenes* cells. The food vehicles reported in listeriosis outbreaks have been deli meats, frankfurters, cheese made from unpasteurized milk, salads, sprouts, and cantaloupes. Postprocess food contamination is common because *L. monocytogenes* persists in food processing plants, contaminates final products, and eventually reaches high numbers in foods. Indeed, *L. monocytogenes* can survive and multiply in harsh conditions owing to its ability to grow at cold temperatures, tolerate acidic and osmotic stresses and disinfectants, and form long-persisting biofilms. Some of these features have been attributed to specific transcriptional regulators, alternative sigma factors, two-component systems, transport proteins, and stress tolerance systems.

*L. monocytogenes* can produce a ManNAc)-based EPS. Cells embedded in EPS aggregates are much more tolerant to various disinfectants and to long-term desiccation. Therefore, listerial EPS is an important factor for listerial persistence in the environment and for food safety. The EPS biosynthesis is linked to the pssA-E operon (lmo0527-lmo0531) in *L. monocytogenes* EGD-e. Two genes from this operon, pssC and pssE, have been found to be critical for EPS biosynthesis. pssC encodes a putative glycosyltransferase, and pssE encodes an I-site type receptor for the bacterial second messenger, c-di-GMP, which is required for activating EPS biosynthesis via the c-di-GMP-binding protein, PssE. C-di-GMP regulation of EPS biosynthetic complexes has been observed in proteobacteria. For instance, the glycosyltransferase BcsA, responsible for cellulose synthesis in many proteobacteria, binds c-di-GMP via a PilZ domain. Alginate biosynthesis in *Pseudomonas aeruginosa* is also regulated by the PilZ domain protein Alg44. However, the regulation of the *P. aeruginosa* Pel EPS synthase is also activated via an I-site type c-di-GMP receptor.

As described in the Examples herein, the evolutionary relationships among the EPS biosynthesis proteins were assessed by performing phylogenetic analysis, which revealed that the listerial EPS biosynthesis machinery has evolved within monoderms and that it is not closely related to PNAG or cellulose biosynthesis proteins. The Examples show that listerial EPS is cell bound and that its chemical composition is unique. Monosaccharide composition, linkage and NMR analyses indicate that the trisaccharide repeating unit of the EPS polymer is {4)-β-ManpNAc-(1-4)-[α-Galp-(1-6)]-β-ManpNAc-(1-}, where ManpNAc is N-acetylmannosamine and Galp is galactose. Using genetic analysis, it was determined that all genes in the pssA-E operon, as well as the pssZ (lmo1913) gene located elsewhere, are required for EPS production and that PssZ functions as an EPS specific glycosylhydrolase. Furthermore, two diguanylate cyclases (DGCs) primarily responsible for c-di-GMP-dependent activation of listerial EPS synthesis were uncovered.

The PssZ protein, also referred to as Lmo1913, has the sequence: MKRFILILILLIFIGAGFFIFLRPESKKTVSAPKETTPTSTSV QTYVKENYTAKNGLIMDYKNTEEPHYLAESIGLYMEYLVEVNDSKTFQKQVNHLEKYFIAEDNFIKWEATDSTTTNAIVDDFRITEALYQASEKFSFPSYKKMADKFLTNTKKYSAEQGVPVDFYDFVHKKKADTLHLSYLNIQAMQQINYRDKAYLPIQTINADPFFTEVFQNGQFKFADQKEVNMIDQMLIAIAYYDENGDIEPNFDNFLQTELASKGKIYARYQRETKKPSSENESTAVYAFLTQYFNKTNQAKNGKITKELLEKMDTSNPETTHFFDYINKEITLKK [SEQ ID NO: 1]. In accordance with the present disclosure, the PssZ protein, and also truncated fragments, mutants, and variants thereof, is useful for hydrolyzing a listerial exopolysaccharide, disintegrating bacterial aggregates, and disinfecting various articles contaminated with listerial bacteria. In particular embodiments, the PssZ protein is used without the transmembrane domain of the protein, thus having the sequence: RPESKKTVSAPKETTPTSTSVQTYVKENYTAKNGLIMDYKNTEEPHYLAESIGLYMEYLVEVNDSKTFQKQVNHLEKYFIAEDNFIKWEATDSTTTNAIVDDFRITE
ALYQASEKFSFPSYKKMADKFLTNTKKYSAEQGVPVDFYDFVHKKKADTLHLSYLNIQAMQQINYRDKAYLPIQTINADPFFTEVFQNGQFKFADQKEVNMIDQMLIAIAYYDENGDIEPNFDNFLQTELASKGKIYARYQRETKKPSSENESTAVYAFLTQYFNKTNQAKNGKITKELLEKMDTSNPETTHFFDYINKEITLKK [SEQ ID NO: 2].

Amino acid sequence variants of the PssZ protein are encompassed within the present disclosure. Modifications to the PssZ protein can be introduced by mutagenesis or protein synthesis. Such modifications include, for example, deletions from, insertions into, and/or substitutions within the amino acid sequence of PssZ. Any combination of deletion, insertion, and substitution can be made to arrive at the final amino acid construct of the variant protein, provided that the final construct possesses the desired solubility and biological activity, such as the enzymatic activity of PssZ. Accordingly, provided herein are variants of the PssZ protein. In some embodiments, the variants have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of PssZ. Reference to a "% sequence identity" with respect to a reference polypeptide is defined as the percentage of amino acid residues in a candidate sequence that are identical with the amino acid residues in the reference polypeptide, after aligning the sequences and introducing gaps, if necessary, to achieve the maximum percent sequence identity, and not considering any conservative substitutions as part of the sequence identity.

One non-limiting example of a suitable PssZ fragment has the sequence:

[SEQ ID NO: 2]
RPESKKTVSAPKETTPTSTSVQTYVKENYTAKNGLIMDYKNTEEPHYL

AESIGLYMEYLVEVNDSKTFQKQVNHLEKYFIAEDNFIKWEATDSTTT

NAIVDDFRITEALYQASEKFSFPSYKKMADKFLTNTKKYSAEQGVPVD

FYDFVHKKKADTLHLSYLNIQAMQQINYRDKAYLPIQTINADPFFTEV

FQNGQFKFADQKEVNMIDQMLIAIAYYDENGDIEPNFDNFLQTELASK

GKIYARYQRETKKPSSENESTAVYAFLTQYFNKTNQAKNGKITKELLE

KMDTSNPETTHFFDYINKEITLKK.

One non-limiting example of a suitable PssZ mutant, referred to herein as a E72Q mutant, has the sequence of PssZ with a Glu72 site substituted with glutamine.

EXAMPLES

Example I

This Example describes the characterization of key components and major targets of the c-di-GMP signaling pathways in the foodborne pathogen *Listeria monocytogenes*, the identification of a c-di-GMP-inducible exopolysaccharide responsible for motility inhibition, cell aggregation, and enhanced tolerance to disinfectants and desiccation, and the elucidation of the role of c-di-GMP signaling in listerial virulence.

Genome-wide genetic and biochemical analyses of c-di-GMP signaling pathways revealed that *L. monocytogenes* has three GGDEF domain proteins ("GGDEF" disclosed as SEQ ID NO: 3), DgcA (Lmo1911), DgcB (Lmo1912), and DgcC (Lmo2174), that possess diguanylate cyclase activity, and three EAL domain proteins, PdeB (Lmo0131), PdeC (Lmo1914), and PdeD (Lmo0111), that possess c-di-GMP phosphodiesterase activity. Deletion of all phosphodiesterase genes (ΔpdeB/C/D) or expression of a heterologous diguanylate cyclase stimulated production of a previously unknown exopolysaccharide. The synthesis of this exopolysaccharide was attributed to the pssA-E (lmo0527-0531) gene cluster. The last gene of the cluster encodes the fourth listerial GGDEF domain protein ("GGDEF" disclosed as SEQ ID NO: 3), PssE, that functions as an I-site c-di-GMP receptor essential for exopolysaccharide synthesis. The c-di-GMP-inducible exopolysaccharide causes cell aggregation in minimal medium and impairs bacterial migration in semi-solid agar, however, it does not promote biofilm formation on abiotic surfaces. The exopolysaccharide also greatly enhances bacterial tolerance to commonly used disinfectants as well as desiccation, which may contribute to survival of *L. monocytogenes* on contaminated food products and in food-processing facilities. The exopolysaccharide and another, as yet unknown c-di-GMP-dependent target, drastically decrease listerial invasiveness in enterocytes in vitro, and lower pathogen load in the liver and gallbladder of mice infected via an oral route, which indicates that elevated c-di-GMP levels play an overall negative role in listerial virulence.

Cyclic dimeric GMP (c-di-GMP) is one of the most common bacterial second messengers. The understanding of c-di-GMP-mediated signal transduction pathways has rapidly expanded. However, this expansion has been dominated by studies of Proteobacteria, and to a lesser extent Actinobacteria and Spirochetes, while studies of c-di-GMP signaling in Firmicutes have been lacking. In the Proteobacteria, elevated levels of intracellular c-di-GMP are associated with inhibition of motility and increased synthesis of biofilm components, e.g. exopolysaccharides (EPS), pili, and/or surface adhesins. In pathogens that propagate extracellularly, elevated c-di-GMP levels have been found generally detrimental for acute infections, although individual components of c-di-GMP signaling networks may play different roles during various stages of infection. In contrast, during chronic infections, c-di-GMP-induced biofilms greatly increase pathogen survival in vivo. In intracellular proteobacterial pathogens, c-di-GMP signaling pathways are required for full-scale virulence in those species that form biofilm-like intracellular structures, but appear to be detrimental, at least in some species, that do not form such structures.

In this Example, the foodborne pathogen *Listeria monocytogenes* was used to gain insight into c-di-GMP-based regulation in Firmicutes in general. *L. monocytogenes* is widespread in the environment. It has been isolated from soil, silage, groundwater, sewage, and vegetation, and actively grows at a broad range of temperatures (from 0 to 44° C.), oxygen levels, pH (from 4.4 to 9.6), and salt concentrations (up to 10% w/v NaCl), and is capable of utilizing a variety of carbohydrates as well as other organic molecules as carbon sources. Listeriosis is a relatively infrequent disease but it has the highest mortality rate, ~20%, among foodborne diseases in the developed world. The complications of listeriosis, common in immunocompromised patients, include encephalitis, meningitis, and stillbirths or infection of the central nervous system in newborns.

Common sources of listerial contamination include unpasteurized milk and milk products, raw meat, and packaged cooked meat products. In plants processing meat and milk products listerial biofilms can persist for years and even decades and cause repetitive contamination of processed foods. In recent years, listeriosis caused by contaminated fresh produce has become a significant concern. According to The Centers for Disease Control and Prevention, the 2011 outbreak caused by *Listeria*-contaminated cantaloupes resulted in 33 deaths and was the largest foodborne disease outbreak in US history in almost 90 years. The understanding of how *listeria* attach and grow on the surfaces of produce is surprisingly poor, and so is the knowledge of the mechanisms ensuring long-term listerial survival. EPS is one of the common components that facilitate bacterial attachment to plant surfaces and increases their tolerance to desiccation and disinfection, both of which are critical parameters for food safety. However, the ability of *L. monocytogenes* to synthesize EPS has remained controversial.

In Proteobacteria, EPS synthesis is commonly induced via c-di-GMP signaling pathways, yet studies of such pathways in Firmicutes are lacking. It is peculiar that distribution of c-di-GMP signaling pathways in Firmicutes is very uneven. Several major genera of pathogenic firmicutes, *Staphylococci, Streptococci* and *Enterococci*, lack these altogether. However, staphylococci retain remnants of c-di-GMP signaling enzymes, which are involved in biofilm regulation but are no longer associated with c-di-GMP. On the other extreme of the spectrum are certain clostridial species, e.g. *Clostridium difficile*, that have numerous enzymes involved in c-di-GMP synthesis and hydrolysis. It has been observed that elevated levels of c-di-GMP inhibited motility and induced cell aggregation in *C. difficile*. The c-di-GMPdependent riboswitches from *C. difficile* expressed in a heterologous have been shown to affect gene expression in a c-di-GMP-dependent manner. One riboswitch is located upstream of the *C. difficile* flagellar biosynthesis operon; the other one is part of the riboswitch-ribozyme system predicted to control adhesin gene expression. Enzymes involved in c-di-GMP synthesis and degradation in *Bacillus subtilis* have been identified, and the role of c-di-GMP in regulating motility and biofilm formation in this species has been characterized.

In this Example, a genome-wide view of c-di-GMP signaling in *L. monocytogenes* is presented. Bioinformatics analysis was used to identify genes involved in c-di-GMP synthesis, degradation and signal transduction. Subsequently, genetic and biochemical approaches were applied to characterize functions of these genes in EPS synthesis, motility inhibition, tolerance to disinfection and desiccation, invasiveness in mammalian cells, and virulence in a mouse model of listeriosis.

Results

Bioinformatic Analysis of the c-Di-GMP Signaling System in *Listeria*

C-di-GMP is synthesized by diguanylate cyclases (DGCs), which contain GGDEF domains ("GGDEF" disclosed as SEQ ID NO: 3), and degraded by c-di-GMP-specific phosphodiesterases (PDEs), which contain either EAL or HD-GYP catalytic domains. The currently sequenced strains of *L. monocytogenes*, and the majority of related listerial species, encode four GGDEF domain proteins ("GGDEF" disclosed as SEQ ID NO: 3), three EAL domain proteins, and no HD-GYP domain proteins (FIG. 1).

The sequence analysis indicated that three of the four GGDEF proteins ("GGDEF" disclosed as SEQ ID NO: 3) from *L. monocytogenes* EGD-e, Lmo1911 (DgcA), Lmo1912 (DgcB), and Lmo2174 (DgcC), contain conserved residues associated with DGC activity, and therefore they possess DGC activities. The three indicated DGCs have similar domain architectures with a GGDEF domain ("GGDEF" disclosed as SEQ ID NO: 3) preceded by either six or eight transmembrane helices (FIG. 1). This domain architecture indicates that c-di-GMP synthesis is regulated by external signals or signals derived from the cell wall or cytoplasmic membrane. The three proteins share approximately 30% identity to each other over their entire lengths, and may have resulted from ancient gene duplications. The EAL domain proteins in strain EGD-e, Lmo0131 (PdeB), Lmo1914 (PdeC), and Lmo0111 (PdeD), have conserved residues required for c-di-GMP binding and hydrolysis, and therefore are believed to possess PDE activities (FIG. 1). These putative PDEs contain only single EAL domains, indicating their cytoplasmic localization.

The dgcA and dgcB genes are codirectional and separated from each other by 20 bp, which indicates that they form an operon. The pdeC gene appears to belong to the same dgcA-dgcB-lmo1913-pdeC (lmo1911-1914) operon. Tiling microarray expression data support an operonal structure of this gene cluster. The intervening gene, lmo1913, encodes a protein of as-of-yet unknown function. Based on structural predictions, Lmo1913 belongs to the six-hairpin glycosidase superfamily (FIG. 1). Therefore, DgcA, DgcB, and PdeC may represent a signaling module involved in c-di-GMP synthesis and degradation, and this module may be involved in controlling synthesis of an unknown EPS.

The GGDEF domain ("GGDEF" disclosed as SEQ ID NO: 3) of the fourth GGDEF protein ("GGDEF" disclosed as SEQ ID NO: 3), Lmo0531, is degenerate. The signature GG(D/E)EF motif (SEQ ID NO: 5) in Lmo531 is $^{208}$DKDDA (SEQ ID NO: 6), which should make this protein incapable of c-di-GMP synthesis (FIG. 1). Five amino acids upstream of the signature motif is an RxxD motif that represents a part of a c-di-GMP-binding sequence known as an I-site. Therefore, without wishing to be bound by theory, it is believed that Lmo0531 acts as a c-di-GMP receptor/effector protein similar to the I-site containing degenerate GGDEF domain proteins ("GGDEF" disclosed as SEQ ID NO: 3). It is peculiar that Lmo0531 is the only c-di-GMP receptor that can be predicted based on genome sequence analysis.

To test functions of the *L. monocytogenes* DGC and PDE proteins and a single identifiable c-di-GMP receptor, these genes were cloned and expressed in *E. coli* indicator strains that respond to changes in intracellular c-di-GMP concentrations in a predictable fashion. Where necessary, proteins were purified to test their activities in vitro.

*L. monocytogenes* PdeB-D Proteins Possess c-Di-GMP PDE Activities

Figure 2A:
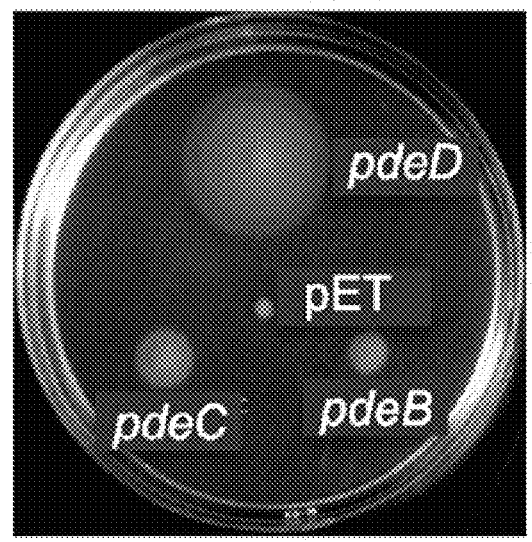

*L. monocytogenes* pdeB, pdeC, and pdeD were expressed in *E. coli* MG1655 ΔyhjH. This mutant lacks a major c-di-GMP PDE, YhjH, and as a result, is impaired in motility in semi-solid agar. It was found that expression of any one of the pde genes was sufficient to partially restore swim zones of MG1655 ΔyhjH in semi-solid agar (FIG. 2A). These results are consistent with all three proteins, PdeB, PdeC, and PdeD, functioning as c-di-GMP PDEs. However, overexpressed but enzymatically inactive EAL domain proteins that retain the ability to bind (but not to hydrolyze) c-di-GMP also can lower intracellular c-di-GMP concentration, thus mimicking the phenotypes of overexpressed PDEs.

Figure 2B:
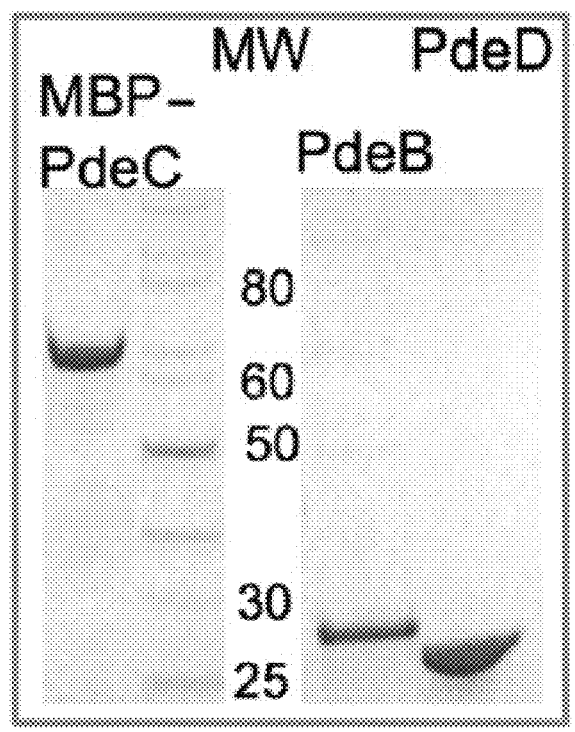
Figure 2C:
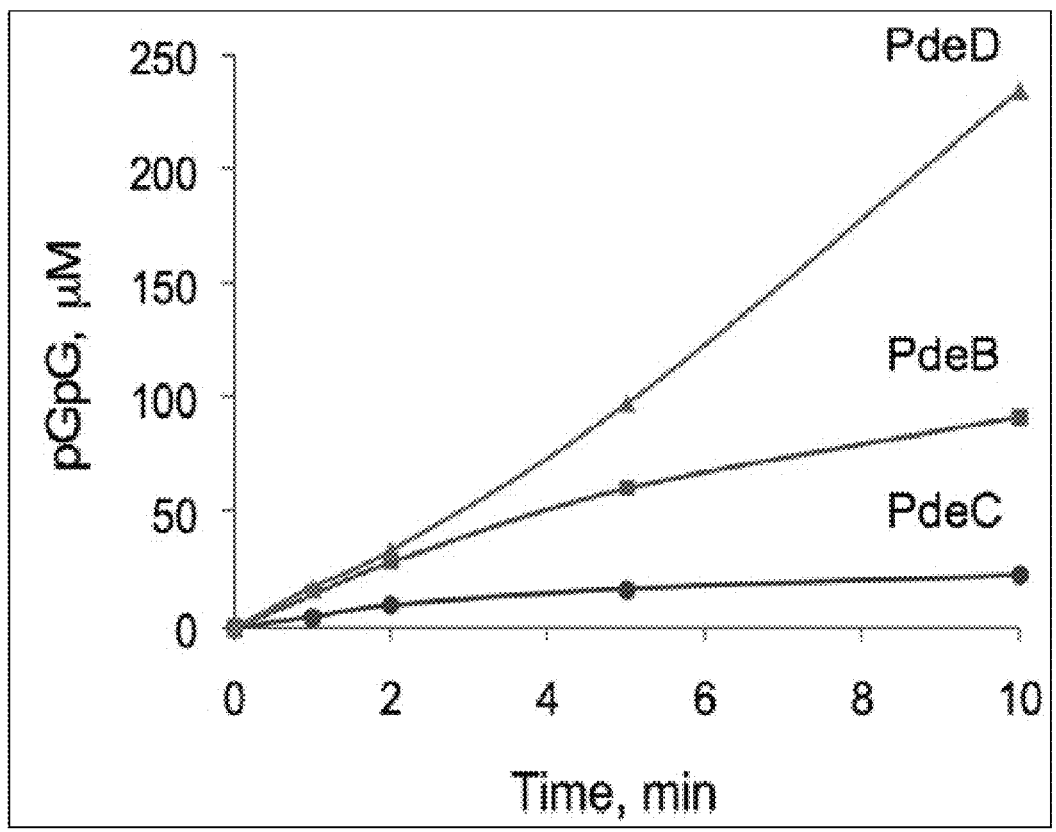

To resolve the ambiguity regarding the enzymatic activity of the PdeB-D proteins, each protein was purified and tested for its ability to hydrolyze c-di-GMP in vitro. The PdeB and PdeD proteins were overexpressed and purified as N-terminal His$_6$-tagged fusions ("His$_6$" disclosed as SEQ ID NO: 4). Since the His$_6$-tagged PdeC fusion ("His$_6$" disclosed as SEQ ID NO: 4) proved to be insoluble, PdeC was purified as a fusion to maltose-binding protein (MBP) (FIG. 2B). The ability of purified PdeB, PdeC, or PdeD to hydrolyze c-di-GMP was assessed by measuring the substrate and products of reactions over time using HPLC. FIG. 2C shows that all three recombinant proteins possess c-di-GMP PDE activities in vitro.

*L. monocytogenes* DgcA-C Proteins Possess DGC Activities

Figure 3A:
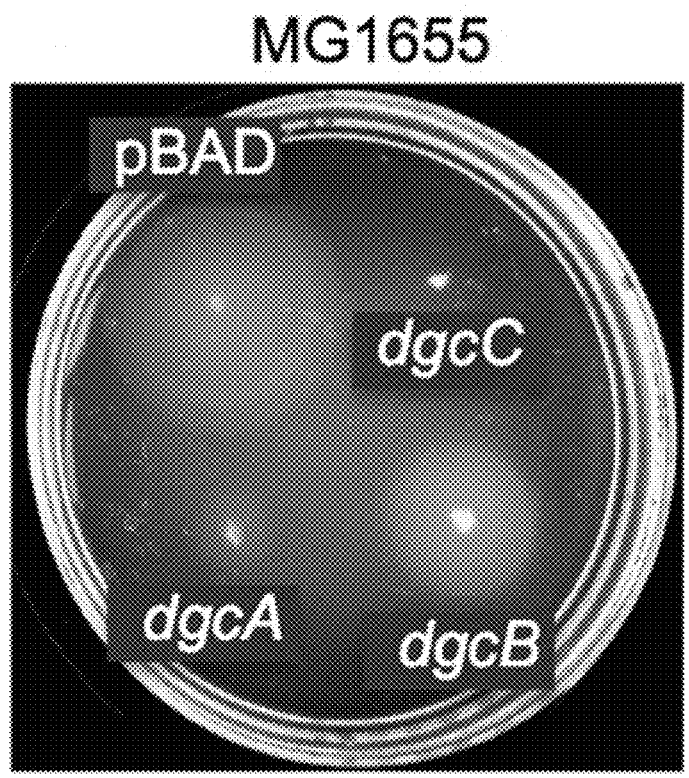

The functionality of putative *L. monocytogenes* DGC proteins was assessed by monitoring swim zone sizes in semi-solid agar. The three dgc genes were cloned into the pBAD/Myc-His vector under the control of an arabinose-inducible promoter. Each of the three dgc genes decreased, to various degrees, the sizes of the swim zones of strain MG1655, which is highly motile in the absence of heterologous DGCs (FIG. 3A).

Figure 3B:
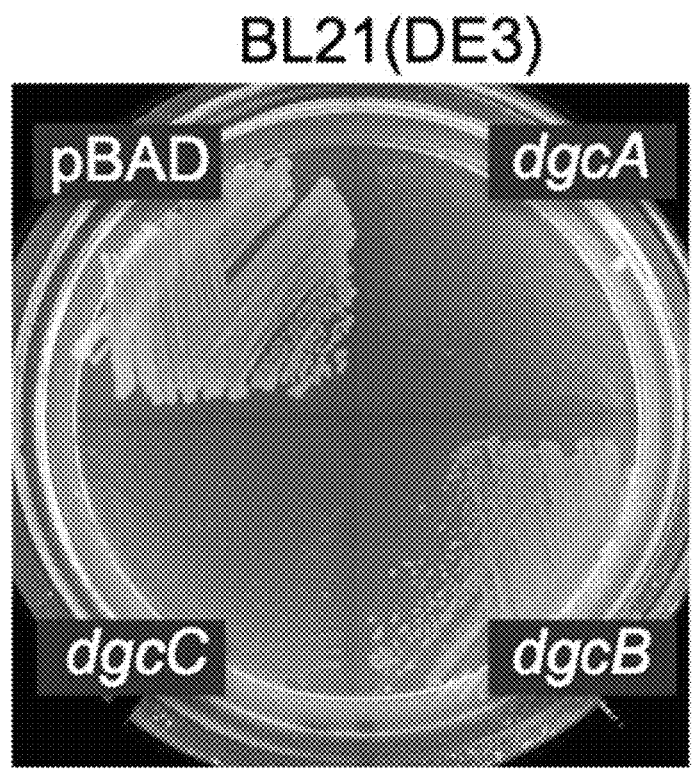

To exclude the possibility of nonspecific motility inhibition (e.g., due to protein toxicity), a second c-di-GMP-dependent phenotype that is independent of motility inhibition was assessed. In *E. coli* BL21 (DE3), c-di-GMP induces synthesis of curli fimbriae that can be detected by staining with Congo red dye. As shown in FIG. 3B, BL21 (DE3) strains expressing each of the three Dgc proteins individually exhibited more intensely colored colonies on Congo red agar compared to the negative control expressing an empty vector. Together, these results indicate that the DgcA-C proteins possess DGC activity.

*L. monocytogenes* Phenotypes Associated with Perturbed Intracellular c-Di-GMP Levels Having established that *L. monocytogenes* EGD-e possesses functional components for c-di-GMP-mediated signaling, phenotypes associated with elevated and decreased intracellular c-di-GMP levels were examined. To perturb c-di-GMP levels, two c-di-GMP metabolizing enzymes, DGC (Slr1143 from *Synechocystis* sp.) and PDE (YhjH from *E. coli*), were expressed in the EGD-e strain and assessed for their role in swimming motility and EPS production. The use of heterologous proteins allowed the effects of changing intracellular c-di-GMP levels to be assessed without undesired changes in protein-protein interactions that may have occurred if listerial DGC and PDE enzymes were overexpressed.

*L. monocytogenes* uses flagella for motility. Expression of Slr1143 blocked swimming of strain EGD-e in semi-solid agar, whereas expression of YhjH had no effect (FIG. 4A, top). Expression of Slr1143 also resulted in more pigmented *L. monocytogenes* colonies on Congo red agar, whereas expression of YhjH had no observable phenotype (FIG. 4B, sectors 10 versus 1 and 9). Later in this Example, it is shown that YhjH is expressed and functional as a PDE in *L. monocytogenes*. Therefore, the lack of a phenotype associated with YhjH overexpression is interpreted as an indication that intracellular c-di-GMP levels in strain EGD-e are already low, and that c-di-GMP does not play a significant role under the conditions used in these assays. Since *L. monocytogenes* is not known to synthesize pili, and the genome of strain EGD-e has no candidate pili genes, Congo red staining was indicative of EPS production. An EPS has been suspected in some naturally occurring *L. monocytogenes* isolates. Further, Congo red staining rings within *L. monocytogenes* colonies exposed to dark-light cycles has been observed. However, the nature of the Congo red-binding extracellular polymer was not investigated.

Construction and Characterization of the *L. monocytogenes* Dgc and Pde Mutants

Having identified two phenotypes associated with elevated c-di-GMP levels, the *L. monocytogenes* pdeB-D genes were inactivated, individually and in combination. Based on the inhibition of swim zones in semi-solid agar by the heterologous DGC, Slr1143, it was believed that pdeB-D mutations would result in smaller swim zones. However, inactivation of individual pde genes did not significantly affect swim zone sizes (FIG. 4C). Inactivation of pairs of pde genes produced relatively minor decreases in swim zones sizes, while simultaneous deletion of all three pde genes, ΔpdeB/C/D, produced a mutant severely impaired in swimming in semi-solid agar (FIG. 4C). This phenotype is similar to the phenotype of the wild type EGD-e expressing the heterologous DGC, Slr1143 (FIG. 4A, top). These results indicate that the PDEs have at least partially overlapping functions in degrading intracellular c-di-GMP.

Expression of Slr1143 in the triple ΔpdeB/C/D mutant did not affect the already inhibited motility any further (FIG. 4A, bottom). However, expression of YhjH in this mutant fully restored the swim zone to the size of the wild-type strain, thus showing that YhjH is expressed and functional in *L. monocytogenes* (FIG. 4A, bottom), and that motility inhibition in semi-solid agar was due to elevated c-di-GMP levels in the triple ΔpdeB/C/D mutant.

The effects of *L. monocytogenes* pde mutations on Congo red binding were tested. The triple ΔpdeB/C/D mutant showed significant accumulation of Congo red (FIG. 4B, sector 2 versus 1), similar to the wild type strain expressing Slr1143 (FIG. 4B, sector 10). Expression of YhjH, but not Slr1143, in the triple ΔpdeB/C/D mutant, inhibited Congo red accumulation (FIG. 4B, sector 6 versus 5 or 7). Individual pde mutants did not affect Congo red staining, while among double mutants, the pdeB/C mutant showed some staining.

In addition to Congo red binding, the colonies of the ΔpdeB/C/D mutant were found to have rough edges, compared to smooth-edged colonies of the wild type strain (FIG. 4D). The observed changes in colony morphology in the ΔpdeB/C/D mutant were not as pronounced as the wrinkled or rough colony morphologies reported in the proteobacterial species overexpressing EPS, however, when combined with enhanced Congo red binding, these changes are indicative of EPS production.

Inactivation of the dgc genes, individually or in combination, resulted in no observable phenotypes, just like the expression of YhjH in the wild type strain produced no phenotype. It is therefore concluded that c-di-GMP plays little, if any, role in strain EGD-e grown under these laboratory conditions.

Bioinformatics-based Identification of the Putative EPS Biosynthesis pssA-E Operon in *L. monocytogenes*

The *L. monocytogenes* genome was searched for EPS biosynthesis genes that could be responsible for c-di-GMP-induced Congo red binding. The lmo0527-0531 operon, designated here pssA-E (polysaccharide synthesis) (FIG. 1), emerged as the prime candidate for this role based on the following reasoning. The last gene of the operon, pssE (lmo0531), encodes a degenerate GGDEF domain protein ("GGDEF" disclosed as SEQ ID NO: 3), believed to function as a c-di-GMP receptor (FIG. 1). If this belief is correct, PssE may be involved in a c-di-GMP-dependent activation of EPS synthesis, similar to activation of cellulose, alginate, and Pel EPS synthesis in Proteobacteria. An additional reason to implicate the pssA-E cluster in EPS biosynthesis was based on the presence of the putative glycosidase gene, lmo1913, in the dgcA-dgcB-lmo1913-pdeC operon that encodes enzymes for synthesis and hydrolysis of c-di-GMP (FIG. 1). Glycosidases counterbalance glycosyltransferases and are integral components of EPS synthesis and degradation apparati.

Without wishing to be bound by theory, it is believed the pssA-E operon encodes enzymes associated with biosynthesis of poly-β-1,6-N-acetyl-D-glucosamine (PNAG) or poly-β-1,4-D-glucopyranose (cellulose), either of which is capable of binding Congo red, or yet another EPS. The key player in this operon is PssC (Lmo0529), which is believed to function as type 2 glycosyltransferase responsible for the polymerization reaction. PssC shows the highest (~30%) identity (over an ~300 amino acid region) to the N-acetylglycosyltransferases involved in PNAG synthesis from *S. aureus* (IcaA) and *Yersinia pestis* (HmsR). However, no other genes found in the staphylococcal ica or yersinial hms gene clusters are present in the pssA-E operon. Instead, the gene downstream of pssC, pssD (lmo530), encodes an ortholog of the BcsB subunit of bacterial cellulose synthases. The BcsB proteins have thus far been associated exclusively with cellulose synthases, yet they are involved in the membrane passage of the polysaccharide polymer not its synthesis, therefore BcsB is believed to be able to accommodate polymers of different composition than cellulose. It is noteworthy that the glycosyltransferases catalyzing cellulose synthesis also belong to type 2 glycosyltransferases, like the PNAG synthases [63]. Further, PssC shares ~25% identity with the type 2 glycosyltransferase BcsA of the cellulose synthase complex of *Rhodobacter sphaeroides*. The almost equal similarity of the listerial glycosyl transferase to PNAG- and cellulose synthases makes predictions of the composition of the listerial EPS unreliable.

The pssA-E Gene Cluster is Responsible for Listerial EPS Synthesis

To test the involvement of the pssA-E gene cluster in EPS biosynthesis, the believed glycosyltransferase gene, pssC, was deleted in the ΔpdeB/C/D background. It was found that the constructed ΔpdeB/C/D ΔpssC mutant no longer bound Congo red (FIG. 4B, sector 4). This result indicates that the pssA-E operon is responsible for c-di-GMP-induced EPS biosynthesis. To verify it further, whether inactivation of pssE in the ΔpdeB/C/D background will also impair EPS synthesis was tested. Indeed, the constructed ΔpdeB/C/D ΔpssE mutant did not bind Congo red either (FIG. 4B, sector 3). It is concluded that PssE, a putative c-di-GMP receptor, plays a critical role in EPS synthesis. Complementation of the ΔpdeB/C/D ΔpssC and ΔpdeB/C/D ΔpssE mutants with individually cloned pssC and pssE, respectively, restored Congo red binding, verifying that the ΔpssC and ΔpssE mutations were responsible for the mutant phenotypes. The ΔpssC and ΔpssE mutations in the ΔpdeB/C/D mutant background reversed the rough colony phenotype back to a smooth appearance (FIG. 4D).

Biochemical Evidence that the PssE Protein is a c-Di-GMP Receptor

To test the prediction that the PssE protein acts as a c-di-GMP receptor, its GGDEF domain ("GGDEF" disclosed as SEQ ID NO: 3) containing the I-site as an MBP fusion (MBP-GGDEF$_{pssE}$) ("GGDEF" disclosed as SEQ ID NO: 3) was overexpressed, and this protein was purified (FIG. 5A) and analyzed for its ability to bind c-di-GMP in vitro using equilibrium dialysis. MBP-GGDEF$_{pssE}$ ("GGDEF" disclosed as SEQ ID NO: 3) was found to bind c-di-GMP with an apparent $K_d$ of 0.79±0.17 μM (FIG. 5B). This value falls within the range of physiologically relevant intracellular c-di-GMP concentrations measured in other bacteria that are believed to be in the submicromolar to low micromolar range. The binding capacity of the MBP-GGDEF$_{pssE}$ protein ("GGDEF" disclosed as SEQ ID NO: 3), $B_{max}$, was calculated to be 2.03±0.12 μM c-di-GMP (μM protein)$^{-1}$ indicating that each PssE molecule can bind two c-di-GMP molecules at saturation. This result is consistent with the observation of an intercalated c-di-GMP dimer bound to the I-sites of crystallized GGDEF domain proteins ("GGDEF" disclosed as SEQ ID NO: 3). Therefore, PssE is a bonafide c-di-GMP receptor that is predicted to transfer the c-di-GMP signal to activate synthesis of the listerial Pss EPS.

C-Di-GMP-Induced Listerial EPS Promotes Cell Aggregation but Plays Limited Role in Biofilm Formation on Abiotic Surfaces PNAG and cellulose increase biofilm formation by the proteobacterial species on abiotic surfaces. To test the effect of c-di-GMP-induced EPS in L. monocytogenes, a conventional Crystal violet dye-binding assay that measures the biomass of cells attached to the wells of microtiter plates following removal of liquid cultures was performed. Surprisingly, an increase in biofilm levels in the ΔpdeB/C/D mutant, compared to the wild type, was not observed when these strains were grown in LB medium (where biofilm formation of strain EGD-e is low). Only a marginal increase in surface-attached biofilm levels in LB supplemented with glycerol (where biofilms are greatly stimulated) was observed (FIG. 6A). Interestingly, this increase in biofilm levels was observed in all ΔpdeB/C/D strains grown in LB plus glycerol, whether or not they produced EPS (FIG. 6A).

These results indicate that, instead of the anticipated stimulation of biofilms, listerial EPS actually inhibits biofilm formation, at least under certain conditions. These results also implicate a c-di-GMP-activated non-EPS component in biofilm stimulation. Similar to the results on polystyrene surfaces, the ΔpdeB/C/D mutant produced no more biofilm in LB medium on glass or metal (aluminum foil or steel coupons) surfaces than did the wild type.

It was noticed that incubation of the ΔpdeB/C/D mutant (but not the wild type, ΔpdeB/C/D ΔpssC or ΔpdeB/C/D ΔpssE mutants) in liquid glucose-rich minimal HTM medium resulted in cell clumping (FIG. 6B). This indicates that listerial EPS strengthens intercellular interactions but not bacterial interactions with abiotic surfaces. The pssC and pssE gene deletions in the ΔpdeB/C/D background completely abolished clumping, just like they decreased Congo red binding in BHI plates. This result confirms that listerial EPS is responsible for clumping.

C-Di-GMP-dependent EPS Impairs L. monocytogenes Motility in Semi-solid Agar

Since the EPS producing ΔpdeB/C/D mutant was impaired in swimming in semi-solid agar (FIG. 4C), the effect of EPS on motility was evaluated. Surprisingly, inactivation of EPS synthesis by the pssC or pssE mutations, restored swimming of the ΔpdeB/C/D mutant in semi-solid agar to the wild-type levels (FIG. 4E). Therefore, swimming in semi-solid agar was impaired exclusively due to listerial EPS.

To gain additional insight into this issue, the motility of the wild type, the ΔpdeB/C/D mutant, and the ΔpdeB/C/D ΔpssC mutant were analyzed in liquid medium where clumping is minimal and not detectable by the naked eye. Phase contrast microscopic observations revealed that single cells of the ΔpdeB/C/D and ΔpdeB/C/D ΔpssC mutants were as motile as the wild-type cells. These results favor the scenario whereby EPS accumulated on cell surfaces results in cell aggregation, which inhibits spreading of the cells in semi-solid agar.

C-Di-GMP-induced EPS Significantly Enhances L. monocytogenes Tolerance to Disinfectants and Desiccation EPS is known to protect bacteria from environmental insults. Here, the role of L. monocytogenes EPS in providing tolerance to disinfection and desiccation was evaluated. The wild-type strain EGD-e as well as its ΔpdeB/C/D mutant synthesizing EPS and grown under clump-forming conditions were subjected to selected disinfectants commonly used in the food-processing industry and produce storage facilities: sodium hypochlorite (bleach), benzalkonium chloride (a quaternary ammonium compound), and hydrogen peroxide. To distinguish between the contribution of EPS versus EPS-independent c-di-GMP-responsive agents, included in the tests were the ΔpdeB/C/D ΔpssC mutant characterized by elevated intracellular c-di-GMP levels but defective in EPS production.

The sodium hypochlorite treatment applied here was highly effective in killing the wild-type strain, but not the EPS producing ΔpdeB/C/D mutant, whose survival was approximately >$10^6$-fold higher than the survival of the wild type (FIG. 6C). Tolerance of the ΔpdeB/C/D mutant to hydrogen peroxide and benzalkonium chloride treatments was also highly, approximately $10^2$-fold, higher, compared to the wild type or the EPS-deficient ΔpdeB/C/D ΔpssC mutant (FIG. 6C). These observations indicate that the c-di-GMP-induced EPS is a critical factor responsible for increased tolerance to these agents.

EPS also enhanced survival of *L. monocytogenes* to long-term desiccation. In this Example, the liquid-grown cultures were centrifuged, and the pellets were kept in a desiccator for 7 or 21 days. It was found that the desiccation survival rates of the EPS producing ΔpdeB/C/D strain were significantly higher, compared to those of the wild type or the ΔpdeB/C/D ΔpssC mutant (FIG. 6D). These results indicate that EPS provides superior protection not only against various commonly used disinfectants in food processing plants but also to desiccation, which may enhance listerial survival during food transportation and storage.

Elevated C-di-GMP Levels Inhibit *L. monocytogenes* Invasion into Mammalian Cells As a foodborne pathogen, *L. monocytogenes* is expected to use gut epithelial cells for primary invasion. The consequences of elevated c-di-GMP levels on bacterial invasion into HT-29 human colon adenocarcinoma cells were examined. As shown in FIG. 7A, the strains with elevated c-di-GMP levels were significantly impaired in invasion, whether elevated c-di-GMP was caused by expression of the heterologous DGC, Slr1143, or by the ΔpdeB/C/D mutations. Consistent with the inhibitory role of c-di-GMP, invasion was increased, by approximately 2-fold, in the *L. monocytogenes* strain expressing a c-di-GMP PDE, YhjH.

Next, what role the c-di-GMP-induced EPS may have played in invasion inhibition was tested. It was observed that the ΔpdeB/C/D ΔpssC and ΔpdeB/C/D ΔpssE mutants showed approximately 2-2.5-fold greater invasiveness compared to the ΔpdeB/C/D mutant (FIG. 7B), but remained approximately 10-fold less invasive than the wild type strain. These results indicate that while EPS moderately inhibits invasion, the major reason for the defective invasion is a c-di-GMP-induced component(s) different from EPS. The nature of this component(s) and the mechanisms through which it inhibits listerial invasion remain to be investigated.

Elevated C-di-GMP Levels Reduce Systemic Spread of *L. monocytogenes* in Mice Infected Via an Oral Route To assess the role of c-di-GMP signaling in vivo, we used a newly developed mouse model of foodborne listeriosis. Groups of BALB/c/By/J mice were fed either wild-type EGD-e or the ΔpdeB/C/D mutant, and the bacterial load in various tissues was assessed 60 h post infection. There was no significant difference in colonization of the ileum, colon or spleen at this time point (FIG. 8). However, the ΔpdeB/C/D triple mutant was significantly impaired in colonizing both the liver and the gallbladder. The decreased bacterial load in the liver appears to be linked to EPS, since the ΔpssC mutation in the ΔpdeB/C/D background restored the bacterial load to the wild-type level (FIG. 8). In fact, no significant differences in bacterial loads in the liver were observed when the same *L. monocytogenes* strains were injected intravenously, indicating that increased levels of c-di-GMP may alter the ability of the bacteria to disseminate from the gut.

Discussion

It was speculated that the *L. monocytogenes* EGD-e genome encodes three GGDEF domain DGCs ("GGDEF" disclosed as SEQ ID NO: 3), one inactive GGDEF domain protein ("GGDEF" disclosed as SEQ ID NO: 3) and three EAL domain PDEs. This belief was verified by a combination of genetic and biochemical tests. Interestingly, all of the enzymes involved in c-di-GMP metabolism are highly conserved not only in the genomes of *L. monocytogenes* isolates but also in other *Listeria* species, e.g. *L. innocua, L. ivanovii, L. seeligeri*, and *L. welshimeri*. The high conservation of these proteins indicates that c-di-GMP signaling pathways play important roles in the evolutionary success of *Listeria*. Such conservation is striking in light of the flexibility in the organization of c-di-GMP signaling pathways observed in other Firmicutes. For example, in the genus *Bacillus*, the number of enzymes involved in c-di-GMP synthesis and hydrolysis varies from three to eleven; it varies from eight to forty in the genus *Clostridium*.

It was determined that c-di-GMP regulation affects at least two targets in *L. monocytogenes*. One of these targets is a novel EPS (FIGS. 4B, 4D, 6B). This finding resolves the long-standing controversy regarding the ability of *listeria* to produce EPS. The second, and possibly additional, target of c-di-GMP regulation, whose identity remains unknown, appears to be responsible for the drastic inhibition of listerial invasiveness in mammalian cells (FIG. 7), modest stimulation of biofilm formation on abiotic surfaces in LB supplemented with glycerol (FIG. 6A), and lower pathogen accumulation in certain mouse organs following oral infection (FIG. 8).

In this Example, it is revealed that the c-di-GMP induced EPS is synthesized by the pssA-E operon. The composition of the listerial EPS is difficult to predict because, while some Pss proteins share similarity to the components of cellulose synthases and PNAG synthases, other components are unique. Interestingly, in contrast to cellulose or PNAG, both of which promote biofilm formation on abiotic surfaces, listerial EPS either does not affect or inhibits biofilm formation on abiotic surfaces. Instead, it promotes cell aggregation, in minimal media (FIG. 6B). These observations indicate that the composition of listerial EPS is different from cellulose or PNAG.

This Example identifies the mechanism through which c-di-GMP activates EPS synthesis in *L. monocytogenes*. C-di-GMP binds to the I-site receptor PssE, whose gene is located in the pss operon, and whose function is essential for EPS biosynthesis. Bacterial cellulose synthases studied thus far are activated via c-di-GMP-binding PilZ domains linked to the C-termini of BcsA subunits. The PNAG synthase of *E. coli* is activated by c-di-GMP binding to two subunits, PgaD and PgaC, one of which, PgaD, is proteolytically degraded in the absence of c-di-GMP. Perhaps the most similar c-di-GMP-dependent mechanism to that operating in *L. monocytogenes* Pss synthase involves the *Pseudomonas aeruginosa* Pel EPS synthase, which is activated via an I-site c-di-GMP receptor protein.

This Example shows that the *L. monocytogenes* Pss EPS is responsible for multiple phenotypes, i.e., cell aggregation, decreased motility in semi-solid media, moderate inhibition of invasiveness in mammalian cells, and drastically elevated tolerance to disinfectants and desiccation. The latter effects of c-di-GMP-induced listerial EPS are particularly noteworthy in light of the increasing frequency of listerial outbreaks associated with produce. Without wishing to be bound by theory, it is believed that EPS contributes to enhanced survival of *listeria* on produce surfaces during washing with disinfectants as well as during transportation and storage of *listeria*-contaminated produce. It is also believed that listerial EPS contributes to bacterial survival in food-processing facilities.

C-di-GMP-induced motility inhibition is common in Proteobacteria. One of the best-understood mechanisms of c-di-GMP-induced motility inhibition involves YcgR, the PilZ-domain c-di-GMP backstop brake that operates in *E. coli* and related enteric bacteria. YcgR binds to the flagellar switch complex and, at elevated c-di-GMP concentrations, introduces a rotational bias that decreases the frequency of flagella reversals and therefore, the frequency of changes in swimming direction. The smooth, almost unidirectional, swimming results in bacteria being trapped in blind alleys of semi-solid agar. YcgR may also slow down rotating flagella. A similar mechanism has been proposed for a PilZ domain protein in *B. subtilis*, however important details have yet to be elucidated. A different mechanism of c-di-GMP-induced motility inhibition was described in *Caulobacter crescentus*, where a PilZ domain receptor affects the abundance of a flagellum assembly regulatory subunit. *B. subtilis* has yet another mechanism of motility inhibition that involves a bifunctional protein EpsE that acts as a glycosyl transferase involved in EPS synthesis and as a molecular clutch that disengages the flagellum rotor from the membrane-localized energy-supplying stator. Whether an EpsE-like clutch operates in *L. monocytogenes* remains unknown, however it is clear that no clutch or break is induced by c-di-GMP because liquid-grown cells show no obvious motility defects. The most striking observation is that inactivation of Pss synthesis is sufficient to restore motility in semi-solid agar. Therefore, listerial spreading in semi-solid agar appears to be inhibited due to cell aggregation and possibly flagella trapping in the EPS. A similar mechanism has been described in *S. enterica*, which at high c-di-GMP levels, secretes cellulose.

Listerial EPS inhibits bacterial invasiveness in mammalian cells, however, only modestly, 2-2.5-fold, whereas an as yet unidentified c-di-GMP pathway is responsible for a much larger component of invasiveness inhibition. The composition of this new c-di-GMP signaling pathway remains unknown. In this regard, it is noteworthy that PssE is the only c-di-GMP receptor that can be predicted based on the genome sequence analysis. *Listeria* lack other identifiable c-di-GMP receptor proteins or c-di-GMP-sensing riboswitches.

In addition to uncovering the role of c-di-GMP in vitro, its role in virulence was tested using a food borne mouse disease model that closely mimics human infection. It was found that elevated c-di-GMP levels decreased listerial infection in the liver, and that this defect could be restored by abolishing EPS biosynthesis. Thus, it is possible that c-di-GMP induced EPS impairs the ability of *L. monocytogenes* to either efficiently disseminate from the intestine or to replicate and spread from cell-to-cell in hepatocytes. While a significant defect in the ability of the ΔpdeB/C/D mutant to invade HT-29 colon carcinoma cells in vitro was observed, there was no difference in the ability of the ΔpdeB/C/D mutant to colonize the murine intestines, compared to the wild type strain. Thus, increased c-di-GMP levels may impair the direct invasion of intestinal epithelial cells mediated by InlA/E-cadherin interactions, but does not significantly impede the ability of *L. monocytogenes* to translocate across the gut mucosa barrier, presumably because the bacteria use alternate mechanisms of invasion. *L. monocytogenes* can transcytose across M cells, specialized epithelial cells that are found both overlying Peyer's patches and scattered elsewhere throughout the epithelium. It is also possible that specialized subsets of dendritic cells in the intestinal lamina propria can engulf *L. monocytogenes* by extending dendrites into the gut lumen, a process that has been demonstrated during oral *S. enterica* infection.

Another issue pertaining to this Example concerns the role of cyclic dinucleotides as bacterial biomarkers recognized by the innate immune system and in the stimulation of the host intracytoplasmic surveillance response. The listerial second messenger c-di-AMP, which is structurally related to c-di-GMP, has been shown to be secreted into the cytosol of infected mammalian cells where it triggers interferon (IFN) production via the STING-signaling cascade. A robust IFNβ response promotes the growth of *L. monocytogenes* administered intravenously. This Example shows that the ΔpdeB/ C/D mutant, which likely has the highest c-di-GMP production achievable during *L. monocytogenes* intracellular growth, was overall less infective following oral infection. This indicates that elevated c-di-GMP levels play a negative role in *L. monocytogenes* virulence, in an apparent contrast with the role of c-di-AMP.

Materials and Methods

This work was performed in accordance with the recommendations in the Guide for the Care and Use of Laboratory Animals published by the National Institutes of Health. All procedures were approved by the Institutional Animal Care and Use Committee (IACUC) at the University of Kentucky (permit number A-3336-01)

Bacterial Strains, Plasmids and Growth Conditions

The bacterial strains and plasmids used in this study are listed in Table 1. The primers used in this study are listed in Table 2. *E. coli* was routinely grown in LB medium supplemented with appropriate antibiotics at 25, 30 or 37° C., as indicated. *L. monocytogenes* was grown in Brain Heart Infusion (BHI) medium (Difco), HTM (minimal medium containing 3% glucose) or LB, supplemented with appropriate antibiotics at 25, 30, 37, or 42° C., as indicated.

TABLE 1

Strains and plasmids used in this Example (Table discloses "GGDEF" and "His$_6$" as SEQ ID NOS 3 and 4, respectively)

| Strain and plasmid | Relevant genotype or description |
|---|---|
| Strains | |
| *Escherichia coli* | |
| DH5α | Strain used for plasmid maintenance and overexpression of MBP-fusions |
| BL21(DE3)pLys5 | Strain used for overexpression of the His$_6$-fusions |
| MG1655 | Wild type |
| MG1655 ΔyhjH | MG1655 ΔyhjH::Km$^r$ |
| *Listeria monocytogenes* | |
| EGD-e | Wild type |
| ΔdgcAB | In-frame deletion of the dgcAB genes |
| ΔdgcC | In-frame deletion in dgcC |
| ΔdgcA/B/C | Deletion of the dgcAB and dgcC genes |
| ΔpdeB | In-frame deletion in pdeB |
| ΔpdeC | In-frame deletion in pdeC |
| ΔpdeD | In-frame deletion in pdeD |
| ΔpdeB/C | Deletion of the pdeB and pdeC genes |
| ΔpdeB/D | Deletion of the pdeD and pdeB genes |
| ΔpdeC/D | Deletion of the pdeD and pdeC genes |
| ΔpdeB/C/D | Deletion of the pdeB, pdeC and pdeD genes |
| ΔpdeB/C/D ΔpssC | ΔpdeB/C/D and in-frame deletion in pssC |
| ΔpdeB/C/D ΔpssE | ΔpdeB/C/D and in-frame deletion in pssE |
| ΔpdeB/C/D::pIMK | ΔpdeB/C/D::pIMK2 |
| ΔpdeB/C/D::yhjH | ΔpdeB/C/D::(pIMK2::yhjH) |
| ΔpdeB/C/D::slr | ΔpdeB/C/D::(pIMK2::slr1143) |
| WT::pIMK | EGD-e::pIMK2 |
| WT::slr | EGD-e::(pIMK2::slr1143) |
| WT::yhjH | EGD-e::(pIMK2::yhjH) |
| Plasmids | |
| pBAD/Myc-His-C | Vector for arabinose-inducible expression |
| pBAD-dgcA | pBAD::dgcA |
| pBAD-dgcB | pBAD::dgcB |
| pBAD-dgcC | pBAD::dgcC |
| pET23a | Vector for T7-inducible His$_6$-fusion protein overexpression |
| pET-pdeD | pET23a::pdeD |
| pET-pdeB | pET23a::pdeB |
| pET-pdeC | pET23a::pdeC |
| pIMK2 | *L. monocytogenes* chromosome integrated expression vector |
| pIMK::slr | pIMK2::slr1143 |
| pIMK::yhjH | pIMK2::yhjH |
| pKSV7 | Vector for gene replacements in *L. monocytogenes* |
| pKSV7-ΔdgcAB | Plasmid for in-frame deletion of dgcAB |

TABLE 1-continued

Strains and plasmids used in this Example (Table discloses "GGDEF" and "His$_6$" as SEQ ID NOS 3 and 4, respectively)

| Strain and plasmid | Relevant genotype or description |
|---|---|
| pKSV7-ΔdgcC | Plasmid for in-frame deletion of dgcC |
| pKSV7-ΔpdeB | Plasmid for in-frame deletion of pdeB |
| pKSV7-ΔpdeC | Plasmid for in-frame deletion of pdeC |
| pKSV7-ΔpdeD | Plasmid for in-frame deletion of pdeD |
| pKSV7-ΔpssC | Plasmid for in-frame deletion of pssC |
| pKSV7-ΔpssE | Plasmid for in-frame deletion of pssE |
| pLysS | Lysozyme expressing plasmid in T7-expression systems |
| pMAL-c2x | Vector for MBP-fusion protein overexpression |
| pMAL-pdeC | pMAL-c2x::pdeC |
| pMAL-GGDEF$_{pssE}$ | pMAL-c2x::pssE(GGDEF domain) |

Plasmid and Mutant Construction

Genomic DNA of L. monocytogenes EGD-e was purified from bacterial cells using a Bactozol kit (Molecular Research Center, OH). L. monocytogenes genes were PCR amplified using genomic DNA, Vent DNA polymerase (New England Biolabs), and gene-specific primers (Table 5). PCR fragments were gel purified with the Gel Purification kit (Qiagen), digested with the appropriate restriction enzymes, and cloned into vector pMAL-c2x (New England Biolabs) in strain DH5α or into vector pET23a (Invitrogen) in strain BL21(DE3) containing pLysS (Invitrogen).

In-frame deletions in the pdeB/C/D, dgcA/B/C, pssC, and pssE genes were generated by site-directed mutagenesis by splice-by-overlap extension PCR. The PCR products containing genes with in-frame deletions were cloned into the temperature-sensitive shuttle vector pKSV7. The recombinant sequences were used to replace the corresponding wild type sequences in the chromosome of the L. monocytogenes EGD-e strain by allelic exchange. L. monocytogenes was electroporated.

Motility and Congo Red Dye Binding Assays

Briefly, for the analysis of swimming in semi-solid agar, 2 μl of overnight cultures was inoculated onto soft agar plates containing 0.25% agar, 1% tryptone, and 0.5% NaCl. Diameters of the swimming zones were assessed after 6-h incubation at 37° C. for E. coli and 12-18-h incubation at 30° C. for L. monocytogenes.

For Congo red binding assays, LB (E. coli) or BHI (L. monocytogenes) agar plates containing 40-80 μg ml$^{-1}$ Congo red were incubated at 30° C. for 48-72 h.

Biofilm Assays

Surface-adhered biofilm formation was assayed in a 96-well format using a modified version of a previously published protocol. Briefly, overnight cultures grown in BHI at 30° C. ($A_{600}$, 2.5-3.5) were diluted into freshly made BHI, LB or LB supplemented with 3% glycerol to an initial $A_{600}$ of 0.05-0.1, and 150 μl aliquots of each culture were inoculated into each of six wells. Biofilms attached to wells were measured following growth for 1-6 days at 30° C. Biofilms were stained with a 0.1% aqueous solution of Crystal violet dye, which was subsequently dissolved in 33% acetic acid and quantified by measurement of $A_{595}$.

Protein Overexpression and Purification

For purification of PdeB::His$_6$ ("His$_6$" disclosed as SEQ ID NO: 4) and PdeD::His$_6$ ("His$_6$" disclosed as SEQ ID NO: 4), isopropyl-β-D-thiogalactopyranoside (IPTG) (final concentration, 0.2 mM) was added to exponentially ($A_{600}$, 0.6-0.7) growing cultures of E. coli BL21 (DE3) pLysS containing appropriate overexpression plasmids. After 2 to 4 h of induction at 30° C., the cells were chilled to 4° C. and collected by centrifugation. The cell pellets were resuspended in buffer (pH 8.0) containing 300 mM NaCl, 50 mM NaH$_2$PO$_4$, and 10 mM imidazole and protease inhibitors (phenylmethylsulfonyl fluoride and P8849 protease inhibitor cocktail) at the concentrations specified by the manufacturer (Sigma-Aldrich). The cell suspensions were passed through a French press mini-cell (Spectronic Instruments, NJ), followed by a brief sonication using a Sonifier 250 (Branson Ultrasonics, CT). The crude cell extracts were centrifuged at 15,000×g for 45 min. Soluble protein fractions were collected and mixed with preequilibrated Ni$^{2+}$ resin (Qiagen) for 1 h at 4° C., which was placed into a column and extensively washed with the resuspension buffer containing 20 mM imidazole. The proteins were subsequently eluted using 200 mM imidazole. The buffer was exchanged with PDE buffer using desalting columns according to the instructions of the manufacturer (Pierce Biotechnology). Protein purity was assessed by SDS-PAGE and protein concentration was determined using a BCA protein assay kit (Pierce Biotechnology).

For purification of MBP::PdeC and MBP::GGDEF$_{pssE}$ fusions ("GGDEF" disclosed as SEQ ID NO: 3), IPTG (final concentration, 0.2 mM) was added to exponentially ($A_{600}$, 0.6-0.8) growing E. coli DH5α containing appropriate plasmids. After 2-h induction, cells were collected by centrifugation. Cell pellets were resuspended in a buffer containing 200 mM NaCl, 0.5 mM EDTA, 5 mM MgCl$_2$, 20 mM Tris-HCl (pH 7.6), and 5% glycerol that also contained protease inhibitors. Following cell disruption and clearing of the crude cell extracts, as described above, soluble protein fractions were mixed with pre-equilibrated amylose resin (New England Biolabs) for 1 h at 4° C., which was subsequently extensively washed with the resuspension buffer. MBP fusions were eluted with maltose and the buffer was exchanged for PDE or c-di-GMP binding assay buffer using desalting columns.

PDE Assays

Briefly, assays were performed by adding a PDE enzyme (1-5 μM) to PDE reaction buffer (final volume, 100 μl) containing 250 μM c-di-GMP, and the reaction was allowed to proceed at 37° C. Aliquots were withdrawn at various time points; the reaction was stopped by addition of CaCl$_2$ (final concentration, 10 mM), and the sample was boiled for 3 min and centrifuged. The supernatant was then filtered through a 0.22-μm filter, and the reaction products were analyzed by reversed-phase HPLC (Summit HPLC system; Dionex) using a Supelcosil LC-18-T column (Sigma-Aldridge). The buffer system and gradient elution program were described previously.

Equilibrium Dialysis

Equilibrium dialysis experiments were performed as previously described. Briefly, MBP-GGDEF$_{PssE}$ ("GGDEF" disclosed as SEQ ID NO: 3) (20 μM) was injected into one of the two chambers of a Dispo-Biodialyzer cassette (10 kD cutoff, The Nest Group, MA) filled with dialysis buffer. c-di-GMP (concentrations from 1 to 50 μM) was injected into the opposite cell of the cassette. The cassettes were maintained for 25 h at room temperature under agitation, after which samples from each chamber were withdrawn, boiled for 3 min, centrifuged, and supernatants were filtered through a 0.22-μm microfilter. The nucleotide concentrations were quantified by HPLC. Binding constants were calculated by the GraphPad Prism software, version 4.03 (GraphPad Software, San Diego, Calif.) using a nonlinear regression model.

Invasion Assay

*L. monocytogenes* invasion properties were analyzed using a gentamicin-based assay with HT-29 human colon adenocarcinoma cell monolayers in 24-well plates. Briefly, overnight cultures of *L. monocytogenes* grown in BHI at 37° C. were centrifuged, washed, and resuspended in DMEM medium. Monolayers of HT-29 cells were inoculated with 100 μl of the *L. monocytogenes* suspensions (~5×10$^8$ CFU ml$^{-1}$) at a multiplicity of infection of 100 and incubated for 1.5 h at 37° C. in a 7% $CO_2$ atmosphere. The monolayers were then washed and incubated in the presence of 100 μg gentamicin ml$^{-1}$ (final concentration) for 1.5 h. Following this incubation, the cell monolayers were washed again and lysed with 0.1% Triton X-100. Appropriate dilutions were plated on BHI plates for enumeration of intracellular bacteria. Each experiment was done in triplicate, and experiments were performed at least three times independently. Statistical analysis was performed by using Tukey's test at p of <0.05.

Foodborne Infection of Mice

Female BALB/c/By/J mice were purchased from The Jackson Laboratory (Bar Harbor, Me.) at 5 weeks of age and used in experiments when they were 6-9 weeks old. Mice were maintained in a specific pathogen free facility at the University of Kentucky and all procedures were performed in accordance with IACUC guidelines. Aliquots of early stationary phase bacteria were prepared and stored at −80° C. To prepare the inoculum, aliquots were thawed on ice, cultured standing in BHI broth for 1.5 h at 30° C., washed once in PBS and then suspended in 5 μl of melted, salted butter (Kroger) and used to saturate a 2-3 mm piece of white bread (Kroger). Infection by the natural feeding route was carried out at night. Briefly, mice were given unrestricted access to water but denied food for 22 h, then placed in an empty cage, and given 5-10 minutes to pick up the contaminated bread piece and eat all of it. Mice were then returned to their original cages with raised wire flooring to prevent coprophagy, and normal mouse chow was replenished.

Processing of Tissue Samples

Colon contents were removed by squeezing with sterile forceps and then flushing with 8 ml of PBS through a 25 g needle. Washed tissues were cut longitudinally and homogenized for 1 min in 2 ml of sterile water using a PowerGen 1000 homogenizer (Fisher) at 60% power. The total number of cell-associated (adherent plus intracellular) *L. monocytogenes* cells was determined by plating serial dilutions on BHI agar supplemented with 15 g LiCl l$^{-1}$ and 10 g glycine l$^{-1}$ (BHI/L+G). Colonies were counted after 48 h incubation at 37° C. This selective agar inhibited the growth of most intestinal microbiota; suspect colonies were confirmed to be *L. monocytogenes* by plating on CHROMagar *Listeria* plates (Becton Dickinson). Spleens and livers were harvested aseptically and homogenized for 30 sec in 2 ml of sterile water. Gallbladders were ruptured with sterile scissors in a microfuge tube containing 1 ml of sterile water and vortexed for 30 sec. Dilutions of each tissue were plated on BHI/L+G agar.

Disinfection and Desiccation Tolerance

Solutions of sodium hypochlorite, hydrogen peroxide, and benzalkonium chloride (Sigma-Aldrich and Sigma Life Sciences) were prepared in sterile phosphate-buffered saline with disinfection concentrations of 1600 ppm, 200 mM, and 100 ppm, respectively. Cultures were grown in HTM with 3% glucose at 37° C. for 24 h, at which point small uniform clumps are formed by the ΔpdeB/C/D strain. Aliquots (250 μl; 10$^8$ cfu/ml) of these cultures were mixed with disinfectants at 1:1 vol ratios in small glass tubes that also contained 0.1 g of acid washed glass beads (Sigma Life Sciences). Following a 10-min exposure to disinfectants at room temperature, D/E neutralizing broth (500 μl; Difco) was added. Samples were vigorously vortexed (for 5 min) and clumps of the ΔpdeB/C/D strain were dispersed due to the action of the glass beads. Serial dilutions were plated on BHI agar and colonies were counted following a 48-h incubation at 37° C.

To assess desiccation tolerance, strains were grown as described above. One milliliter of cultures (5×10$^8$ cfu/ml) was centrifuged in 1.5 ml eppendorf microtubes containing 0.1 g glass beads. After supernatant removal, the tubes were stored at room temperature in a desiccator jar containing anhydrous calcium sulfate. After 7 and 21 days, the pellets were resuspended in phosphate buffered saline, vigorously vortexed, and plated on BHI agar. Colonies were counted following 48-h incubation at 37° C.

Example II

Elevated levels of the second messenger c-di-GMP activate biosynthesis of an exopolysaccharide (EPS) of previously unknown composition in the food-borne pathogen *Listeria monocytogenes*. This EPS protects cells against disinfectants and desiccation, indicating its significance for listerial persistence in the environment and for food safety. The phylogenetic origin of this EPS was analyzed, its composition was determined, the genes involved in its biosynthesis and hydrolysis were characterized and diguanylate cyclases activating its synthesis were identified. Phylogenetic analysis of EPS biosynthesis proteins indicates they have evolved within monoderms. Scanning electron microscopy revealed that *L. monocytogenes* EPS is cell surface-bound. Secreted carbohydrates represent exclusively cell-wall debris. The purified EPS has a unique composition, i.e., N-acetylmannosamine (ManNAc) and galactose (Gal) in a 2:1 ratio. Linkage analysis revealed 4-ManNac, 4,6-ManNAc, and terminal-Gal residues. All genes of the pssA-E operon are required for EPS production and so is a separately located pssZ gene. The examples show that PssZ has an EPS-specific glycosylhydrolase activity. The exogenously added PssZ prevents EPS-mediated cell aggregation and disperses preformed cell aggregates, whereas the E72Q mutant in the presumed catalytic residue, is much less active. The diguanylate cyclases DgcA and DgcB, whose genes are located next to pssZ, are dedicated to EPS regulation.

All *L. monocytogenes* pssA-E Operon Genes are Required for Biosynthesis of Cell-bound EPS The *L. monocytogenes* ΔpdeB/C/D mutant, in which all c-di-GMP phosphodiesterase (PDE) genes are deleted, and therefore intracellular c-di-GMP levels are expected to be elevated compared with the wild type, produces copious amounts of EPS in minimal HTM medium with 3% glucose (HTM/G). This EPS is responsible for aggregation of the ΔpdeB/C/D strain (FIG. 9A), which indicates that at least some EPS is cell bound. Therefore, attempts to visualize it via scanning electron microscopy (SEM) were made. Intercellular fiber-like connections between ΔpdeB/C/D cells were observed, whereas no intercellular connections were seen with the EPS-negative ΔpdeB/C/D ΔpssC strain containing a deletion of the glycosyltransferase gene, or in the wild-type strain, EGD-e (FIGS. 9A-9C). The cell surface-attached EPS synthesized by ΔpdeB/C/D cells apparently accounts for the formation of large cell aggregates in HTM/G medium. These aggregates settle out from the culture medium when flasks/test tubes are not agitated. The aggregates are not easily dispersed by vortexing but can be dispersed by vortexing in the presence of glass beads. Following dispersion, the aggregates do not reform.

Two genes of the pssA-E operon, pssC and pssE, are indispensable for EPS biosynthesis. In order to test the involvement of other pss genes, in-frame deletions in the remaining genes of this operon (FIG. 10A) were constructed and used cell aggregation in HTM/G liquid medium and Congo red dye binding in HTM/G agar medium to assess EPS production. As shown in FIGS. 10B-10C, deletions in pssA, pssB and pssD in the ΔpdeB/C/D genetic background abrogated both phenotypes, thereby indicating that all pssA-E genes are involved in listerial EPS biosynthesis.

The Listerial EPS Biosynthesis Machinery has Evolved within Monoderms and the Listerial EPS has a Unique Composition The PssC and glycosyltransferases involved in cellulose and PNAG biosynthesis are approximately similar. The PssD and the BcsB proteins (Pfam protein domain: BcsB), which have thus far been associated exclusively with cellulose synthases, are also approximately similar. Phylogenetic analysis of key listerial EPS biosynthetic proteins were conducted. Phylogenetic trees were constructed for PssC, PssD, and PssZ (an EPS-specific glycosylhydrolase). It was found that sequences of these three listerial proteins clustered within a branch of Firmicutes (and include homologs from *Bacillus, Clostridium*, and *Lactobacillus*) and are closer related to proteins from Actinobacteria and/or Green filamentous bacteria, sister monoderm (single-membrane bacteria) branches, to the exclusion of proteobacterial sequences (FIGS. 11A-11C).

Comparative genomic analysis identified gene clusters in other *Listeria* species (e.g. *L. innocua, L. seeligeri* and *L. ivanovii*), bacilli, including the model firmicute *Bacillus subtilis* (ydaJ-ydaN), and clostridia, including the emerging pathogen *Peptoclostridium difficile* (CD630_10280-D630_10310), which are homologous to the listerial pss operon. Therefore, listerial EPS biosynthesis proteins have evolved within monoderms rather than being acquired via horizontal gene transfer from other branches such as the proteobacteria. This analysis indicates that the composition of the listerial EPS is unique and unrelated to PNAG or cellulose.

The c-Di-GMP-Activated *L. monocytogenes* EPS is Composed of ManNAc and Gal

To purify the cell-bound EPS, the ΔpdeB/C/D strain was used, whereas the ΔpdeB/C/D ΔpssC mutant impaired in the EPS synthesis was used as a negative control. The cell-bound EPS was removed from cells by boiling followed by ethanol precipitation. The insoluble cell-bound EPS was isolated from the ΔpdeB/C/D strain but not from the ΔpdeB/C/D ΔpssC strain. This EPS contained carbohydrates, based on the anthrone reaction, but was not affected by cell-wall hydrolases (lysozyme and mutanolysin) or nucleases (DNase I and RNase A).

Glycosyl composition analysis performed at the Complex Carbohydrate Research Center showed that the purified listerial EPS is made of N-acetylmannosamine (64.9%) and galactose (33.6%) (Table 2). The preparation also contains trace amounts of other sugars (1.4% of its molar mass) that are unlikely to be genuine components of the polymer. Linkage analysis demonstrated the pyranose forms of terminal galactose (t-Galp), 4-linked N-acetyl mannosamine (4-ManpNAc), and 4,6-linked N-acetyl mannosamine (4,6-ManpNAc). Based on the presence of N-acetylmannosamine in approximately twofold abundance over terminal galactose, listerial EPS consists of a heteropolymer with a trisaccharide repeat unit of {4)-ManpNAc-(1-4)-[Galp-(1-6)]-ManpNAc-(1-}, which is referred to herein as ManNAc-Gal EPS (FIG. 12). To confirm this repeat unit and determine the configurations of the linkages between ManNAc and galactose residues, the structure of ManNAc-Gal EPS was analyzed by NMR spectroscopy.

TABLE 2

| Monosaccharide composition of *L. monocytogenes* EPS | | |
|---|---|---|
| Glycosyl residue | Mass (μg) | Mol % |
| Rhamnose (Rha) | 1.2 | 0.4 |
| Mannose (Man) | 0.8 | 0.3 |
| Galactose (Gal) | 102.2 | 33.6 |
| Glucose (Glc) | 2.2 | 0.7 |
| N-acetyl mannosamine (ManNAc) | 242.3 | 64.9 |
| Sample carbohydrate content, Σ | 348.7 | 99.9 |

Identification and Chemical Shift Assignment of Monosaccharide Residues in ManNAc-Gal EPS The ManNAc-Gal EPS was completely insoluble, precluding liquid-state NMR analysis on the native material. Considering that chitin, a polymer of β-1,4-linked N-acetyl-glucosamine, is also insoluble, but chitosan, which is obtained from chitin by N-deacetylation, is soluble in dilute acid, ManNAc-Gal EPS may also be made soluble by N-deacetylation. Sodium hydroxide treatment of ManNAc-Gal EPS removed about 80% of N-acetyl groups (estimated by integration of the acetyl-$CH_3$ signal at 2.08 ppm) and resulted in EPS-N, which was freely soluble in dilute acid. The 1-D proton NMR spectrum of EPS-N (FIG. 13A) showed two broad, partially overlapping anomeric signals at a chemical shift above 5 ppm and several broad peaks between 4.2 and 3.7 ppm. To identify the sugars belonging to the anomeric signals, a series of 2-D NMR spectra was acquired. COSY and TOCSY spectra were used to assign the proton chemical shifts, and an HSQC spectrum was obtained to assign the carbon chemical shifts of the monosaccharide residues present in EPS-N. The residues and their linkage positions were identified from the proton and carbon chemical shifts. A NOESY spectrum was used to determine the monosaccharide sequence. The spectra clearly identified one of the anomeric peaks as belonging to a terminal α-galactopyranose (α-Galp) residue (Table 3).

TABLE 3

| NMR chemical shifts of N-deacetylated listerial EPS | | | | | | | | |
|---|---|---|---|---|---|---|---|---|
| | | | Chemical shift (ppm) | | | | | |
| Sample | | Residue | 1 | 2 | 3 | 4 | 5 | 6 |
| EPS-N | A | 4,6-β-ManN•HCl | 5.115 | 3.98 | 4.21 | 3.95 | 3.89 | 3.98/3.86 |
| | | | *99.1* | *56.8* | *70.6* | *78.5* | *76.1* | *68.7* |
| | B | 4-β-ManN•HCl | 5.106 | 3.97 | 4.19 | 3.91 | 3.70 | 3.93/3.80 |
| | | | *99.4* | *56.8* | *70.7* | *78.4* | *77.7* | *62.9* |

TABLE 3-continued

NMR chemical shifts of N-deacetylated listerial EPS

| Sample | | Residue | Chemical shift (ppm) | | | | | |
| --- | --- | --- | --- | --- | --- | --- | --- | --- |
| | | | 1 | 2 | 3 | 4 | 5 | 6 |
| | C | α-Gal | 5.080 | 3.89 | 3.90 | 4.00 | 3.88 | 3.78/3.76 |
| | | | *101.5* | *70.9* | *72.3* | *72.0* | *74.1* | *64.1* |
| EPS-H | A' | 4,6-β-ManN•HCl | 5.113 | 3.98 | 4.21 | 3.95 | 3.91 | 3.99/3.86 |
| | | | *99.1(168 Hz)* | *56.8* | *70.6* | *78.5* | *76.3* | *68.7* |
| | B' | 4-β-ManN•HCl | 5.096 | 3.97 | 4.20 | 3.92 | 3.71 | 3.94/3.80 |
| | | | *99.4 (168 Hz)* | *56.8* | *70.7* | *78.2* | *77.6* | *62.9* |
| | C' | α-Gal | 5.076 | 3.89 | 3.90 | 4.00 | 3.88 | 3.78/3.76 |
| | | | *101.5 (172 Hz)* | *70.9* | *72.3* | *72.0* | *74.1* | *64.1* |
| Monosaccharide standards | | α-ManN•HCl | 5.40 | 3.68 | 4.17 | 3.61 | 3.92 | 3.84/3.83 |
| | | | *93.1 (171 Hz)* | *57.2* | *69.5* | *69.0* | *74.7* | *63.1* |
| | | β-ManN•HCl | 5.20 | 3.72 | 4.01 | 3.54 | 3.47 | 3.90/3.76 |
| | | | *93.7 (167 Hz)* | *58.3* | *72.1* | *68.8* | *78.8* | *63.2* |

Carbon chemical shifts are in italics;
downfield carbon shifts indicating glycosylation are in bold.
Measured $^1J_{CH}$ coupling constants are in parentheses.

The residue to which the second anomeric signal belonged was difficult to identify due to spectral overlap. However, the signals that could be observed were consistent with mannosamine hydrochloride (ManpN.HCl). In order to obtain a complete assignment of the mannosamine residues, EPS-N was subjected to partial acid hydrolysis (obtaining EPS-H). The 1-D proton NMR spectrum of the resulting EPS-H confirmed that the galactose side chains were cleaved more readily than the mannosamine backbone, showing considerable reduction of the galactose anomeric proton signal (FIG. 13A), as well as complete loss of residual N-acetyl groups. The 2-D NMR analysis of EPS-H allowed the chemical shifts of the mannosamine residues to be completely assigned. These chemical shifts were identified as 4-linked, based on the downfield chemical shift of C4 (Table 3). The spectra of EPS-H still showed a minor amount of α-galactose, and therefore a branching mannosamine residue to which the galactose is attached (FIG. 13A) was also seen. The linkage data of the native EPS had shown the presence of 4,6-linked mannosamine, and as the backbone was 1→4-linked, branching was seen on O-6 of mannosamine. The HSQC spectrum (FIG. 13B) displayed a weak set of CH$_2$ signals at 68.7 ppm, exhibiting downfield displacement typical of glycosylation and indicating the residual presence of 4,6-linked mannosamine. Similar signals were present in the HSQC spectrum of EPS-N where they had about equal intensity with those from 4-linked mannosamine (FIG. 13B), indicating that branching occurs on every other mannosamine residue. In addition to identifying the H/C-6 mannosamine signals, the comparison of the spectra of EPS-N with those from EPS-H allowed the assignment of the remaining mannosamine signals in EPS-N, and this assignment is summarized in Table 3. NOESY confirmed the putative sequence by detecting correlations between the anomeric proton of galactose and H-6 of 4,6-ManN, and between the anomeric protons of the ManN residues with H-4 of ManN (FIG. 13C).

Anomeric Configurations of Monosaccharide Residues in ManNAc-Gal EPS

It is difficult to determine the anomeric configuration of sugars with manno-stereochemistry because the H1-H2 coupling constants and the chemical shifts of both anomers are similar. The anomeric 1-bond C—H J-coupling constants have been shown to often provide a more unambiguous distinction between α- and β-configurations of pyranoses and methylpyranosides. Thus, α-anomeric pyranoses typically have 1JCH values between 169 and 173 Hz, and β-pyranoses between 158 and 162 Hz. In order to measure the 1JCH coupling constant of the mannosamine anomeric C—H pair, an HSQC spectrum of EPS-H without decoupling during acquisition was acquired using a narrow spectral width in the carbon dimension, covering only the anomeric carbons (FIG. 14). The 1JCH coupling constants of the mannosamine residues were 168 Hz, and that of the galactose residue was 172 Hz, indicating that galactose was in the α-anomeric configuration, but giving no conclusive answer regarding the anomeric configuration of mannosamine. For the galactose residue, this was in agreement with the assigned chemical shifts. Although the 1JCH coupling constant of 168 Hz was closer to the typical range of α-pyranoses, the chemical shifts of the mannosamine residues seemed to agree better with the β-configuration as C-5 of both of the mannosamine residues resonated further downfield than would be expected for the α-anomer. Furthermore, the NOESY spectrum reveals NOE contacts of the anomeric proton with H2, H3, H4, and H5 (FIG. 13C), which is only possible in the β-anomer. Of these correlations, H1-H2, H1-H3, and H1-H5 are with protons of the same residue, whereas the correlation H1-H4 reveals a short distance between the anomeric proton and H4 of the neighboring ManN residue.

The 1JCH coupling constants of both anomers of fully acylated mannosamine have been reported as 178.4 and 166.7 Hz for α and β, respectively. However, O1-acylation increases the anomeric 1JCH coupling constant by about 5 Hz. No 1JCH coupling constants for α- and β-mannosamine hydrochloride have been reported previously. In order to obtain these values, mannosamine hydrochloride was synthesized from N-acetylmannosamine by acid hydrolysis, and sufficient NMR data to assign both α- and β-pyranose anomers and to measure their anomeric 1JCH coupling constants was acquired. The results are demonstrated in FIG. 14 and listed in Table 3, and show that β-ManN. HCl has an unusually large 1JCH coupling constant of 167 Hz between C1 and H1. This, together with the better agreement of the carbon chemical shifts with the β-anomer of the standard as well as the multiple NOESY cross peaks, indicates that the ManN in the EPS has the β-configuration. The EPS trisaccharide repeating unit structure is therefore as follows:

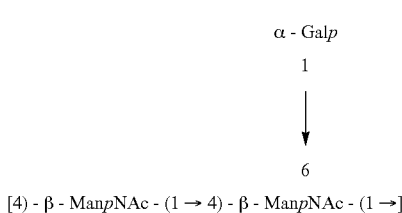

[4] - β - ManpNAc - (1 → 4) - β - ManpNAc - (1 →]

The Secreted *L. monocytogenes* Carbohydrates are Pss Independent

Whether some of the listerial EPS is also secreted in the growth medium, in addition to being cell-surface attached, was tested. To extract secreted carbohydrates, culture supernatants of the ΔpdeB/C/D and ΔpdeB/C/D ΔpssC strains, from which cell wall debris, extracellular DNA, and proteins were removed, were used. Soluble carbohydrates were precipitated with ethanol. It was found that the re-solubilized ethanol precipitants derived from culture supernatants of the two strains contained the same amounts of total carbohydrates (as determined by the anthrone reaction). This result indicates that secreted carbohydrates do not depend on the glycosyltransferase PssC and pss operon.

To further investigate the nature of these secreted carbohydrates, they were subjected to NMR spectroscopic analyses. The proton NMR spectra in $D_2O$ revealed identical compositions for the secreted carbohydrates from the ΔpdeB/C/D and ΔpdeB/C/D ΔpssC strains, which were dominated by rhamnose and N-acetylglucosamine (FIG. 15A). The identity of sugar residues was confirmed by 2D proton TOCSYNMR (FIGS. 15B-15D). Because rhamnose and N-acetylglucosamine are abundant in teichoic acids in strain EGD-e and in the peptidoglycan, and because PssC does not affect the abundance of extracellular soluble carbohydrates, the conclusion is that they are derived from the *L. monocytogenes* cell-wall debris and are unrelated to the ManNAc-Gal EPS. Hence, ManNAc-Gal EPS is produced exclusively in an insoluble, cell surface-attached form.

Genetic Evidence that pssZ (Lmo1913) Encodes a ManNAc-Gal EPS-specific Glycosylhydrolase The pss operon lacks an identifiable gene for a ManNAc-Gal EPS hydrolase necessary for EPS processing. It was previously noticed that the lmo1913 gene located in the gene cluster involved in c-di-GMP synthesis and degradation, dgcA-dgcB-lmo1913-pdeC (FIG. 16A), encodes a putative glycosylhydrolase. In this operon, dgcA and dgcB encode DGC enzymes and pdeC encodes a c-di-GMP PDE.

To test whether lmo1913 encodes a ManNAc-Gal EPS-specific glycosylhydrolase, lmo1913 was overexpressed in the ΔpdeB/C/D strain by integrating an additional copy of lmo1913 downstream of a strong promoter in the chromosome (strain ΔpdeB/C/D-pssZ, Table 3). Overexpression of the lmo1913 gene did not change Congo red binding significantly; however, it reduced cell aggregation in liquid HTM/G medium (FIGS. 16B and 16C, strains 1 and 5; FIG. 16D). The deletion of the wild-type lmo1913 gene in the ΔpdeB/C/D background (strain ΔpdeB/C/D ΔpssZ) drastically reduced Congo red binding and abolished cell aggregation (FIGS. 16B-16C, strains 1 and 2). These observations are consistent with the EPS glycosylhydrolase function of Lmo1913, which is herein designated PssZ [in accord with other glycosylhydrolases, e.g. BcsZ]. Notably, the ΔpdeB/C/D ΔpssZ strain was not impaired in ManNAc-Gal EPS synthesis and produced some ManNAc-Gal EPS, which can be inferred from its higher Congo red staining, compared with the staining of EGD-e and the EPS negative ΔpdeB/C/D ΔpssC strain (FIG. 16B, strains 2, 6, and 7). These results indicate that PssZ is not essential for ManNAc-Gal EPS biosynthesis but is necessary for optimal ManNAc-Gal EPS production.

Biochemical Evidence that PssZ has ManNAc-Gal EPS-specific Glycosylhydrolase Activity To test the ManNAc-Gal EPS-specific glycosylhydrolase activity of PssZ more directly, a fragment of this protein lacking the transmembrane domain but retaining the presumed catalytic domain was overexpressed in *E. coli* and purified as a C-terminal His6-fusion ("His6" disclosed as SEQ ID NO: 4) (FIG. 17A). In addition, the PssZ point mutant E72Q, which is believed to be impaired in hydrolytic activity, was constructed and purified (FIG. 17A). As shown in FIG. 9B, Glu72 is conserved in PssZ and its homolog from the bacterial species *L. innocua*, and is also conserved among other members of the glycosylhydrolase family 8, to which PssZ may belong. The complementation of the ΔpdeB/C/D ΔpssZ strain with the wild-type pssZ gene (strain ΔpdeB/C/D ΔpssZ-pssZ) restored Congo red binding and cell aggregation phenotypes, whereas complementation with pssZ E72Q (strain ΔpdeB/C/D ΔpssZ-pssZ E72Q) failed to do so (FIG. 16B-16C, strains 2, 3, and 4).

Next, purified insoluble ManNAc-Gal EPS was treated with PssZ and PssZ E72Q. The anthrone assay did not detect any PssZ activity, indicating that PssZ is not able to solubilize and hydrolyze ethanol precipitated EPS. However, the addition of purified PssZ to the inoculum of the ΔpdeB/C/D strain inhibited cell aggregation in a dose-dependent manner, i.e., 0.13 μg $ml^{-1}$ (final concentration) inhibited aggregation partially, whereas a 10-fold higher level of PssZ (1.3 μg $ml^{-1}$) inhibited it completely (FIG. 17C). When purified PssZ E72Q was tested in the same assay, it had only a minimal effect on cell aggregation possibly due to its residual hydrolytic activity (FIG. 17C). These results indicate that PssZ hydrolyzes listerial EPS.

Whether PssZ can disperse preformed cell aggregates of the ΔpdeB/C/D strain was also tested. Cell aggregates from a stationary phase culture were mixed with the PssZ and PssZ E72Q proteins in medium containing HTM salts lacking a carbon source and incubated at 30° C. PssZ (32 μg $ml^{-1}$, final concentration) dispersed cell aggregates almost completely after 6 h of incubation (FIG. 17D), whereas PssZ E72Q, used at the same concentration, decreased cell aggregates to a much lesser degree (FIG. 17D). The presence of reducing sugars in the supernatants obtained after treatment of cell aggregates with the wild-type PssZ protein was able to be detected. These results show that PssZ is a ManNAc-Gal EPS-specific glycosylhydrolase.

Contributions of Listerial DGCs to ManNAc-Gal EPS Biosynthesis

Given that the pssZ gene is located next to the dgcA and dgcB genes encoding DGCs, it was questioned whether these dgc genes were primarily responsible for stimulating ManNAc-Gal EPS biosynthesis. To analyze the role of these DGCs in EPS production, individual in-frame deletions were constructed in dgcA and dgcB, as well as a deletion in both genes in the ΔpdeB/C/D mutant background. A deletion in the third DGC gene present in *L. monocytogenes*, dgcC, was also constructed for comparison. Deletions of either dgcA or dgcB genes drastically decreased Congo red binding as well as cell aggregation in HTM/G liquid medium (FIGS. 18I-18C). Deletion of both genes resulted in a more severe defect in cell aggregation than the individual deletions, although this was not as pronounced in the Congo red binding assay. In contrast, deletion of the dgcC gene did not decrease Congo red binding (FIG. 18A) or cell aggregation (FIG. 18B and FIG. 18C). Therefore, DgcA and DgcB are the two DGCs primarily responsible for regulating ManNAc-Gal EPS synthesis.

Discussion

The ability of *L. monocytogenes* to produce EPS has been controversial for a long time. Indirect evidence of EPS production by various listerial strains has been previously demonstrated using various techniques, e.g. staining with ruthenium red and Congo red, fluorescein-conjugated lectin binding, fluorescent dye-conjugated antibody binding, phenolic sulfuric acid analysis, and fibril or matrix analysis via SEM. Earlier, a putative EPS biosynthesis cluster responsible for Congo red binding and cell aggregation, as well as drastically increased tolerance of *L. monocytogenes* to commonly used disinfectants and to desiccation, was identified. It was also shown that EPS biosynthesis is activated by c-di-GMP via the I-site c-di-GMP receptor PssE. This example elucidates the relationship between listerial EPS and other EPSs, the composition and structure of listerial EPS, the genes involved in the synthesis and hydrolysis of listerial EPS, and the DGCs involved in c-di-GMP-dependent regulation of EPS biosynthesis.

It was determined that listerial EPS produced by the pssA-E operon proteins is exclusively cell bound, as carbohydrates secreted in culture media contained sugars characteristic of cell-wall material, and their quantities were independent of the glycosyltransferase PssC. The listerial EPS has a unique structure. Based on composition, linkage, and NMR analysis, listerial EPS is a heteropolymer with a trisaccharide repeat unit consisting of {4)-β-ManpNAc-(1-4)-[α-Galp-(1-6)]-β-ManpNAc-(1-}. This structural analysis provides extra information indicating that the glycosyltransferase PssC belongs to the glycosyl hydrolase family 2 proteins, which utilize an inversion mechanism during polymerization of activated sugar residues (in this case, UDP-α-ManNAc). The resulting polymer synthesized by PssC therefore contains β1-4 linked ManNAc residues. Finally, the ManNAc-Gal EPS structure is further supported by the sequence information of the dedicated glycosylhydrolase PssZ that belongs to the class of β1-4 linkage-specific glycosylhydrolases.

The phylogenetic analyses (FIGS. 11A-11C) indicate that ManNAc-Gal biosynthesis has evolved in monoderms, rather than being recently brought in by a horizontal gene transfer, as supported by the similarities of PssC to cellulose and PNAG synthases from the proteobacteria, and the similarity of PssD to the BcsB protein. It is noteworthy that BcsB has previously been found to be associated only with cellulose biosynthesis. The recent structure of the cellulose synthase from *R. sphaeroides* showed that BcsB facilitates movement of the growing cellulose chain through the cell wall and periplasmic space. Without wishing to be bound by theory, it is believed that PssD performs a similar function in ManNAc-Gal EPS extrusion through the cell wall. Therefore, the BcsB domain present in the BcsB and PssD proteins in itself is not specific toward a given polysaccharide; instead, it forms an EPS extrusion scaffold.

The functions of the PssA and PssB proteins encoded in the pss operon are less clear, although, as we determined here, all of them are required for ManNAc-Gal EPS synthesis. Although the function of PssA cannot be predicted, the PssB protein seems to belong to the carbohydrate esterase 4 superfamily that contains enzymes performing deacetylation of chitin, peptidoglycan, and xylan. Therefore, it is believed that PssB deacetylates some of the ManNAc residues in the listerial EPS. Such residues would not have been detected in the listerial EPS due to the methodology used to determine its monosaccharide composition. Surprisingly, deletion of PssB, which is believed to be nonessential, abolished ManNAc-Gal EPS synthesis. Without wishing to be bound by theory, it is believed that this occurs due to a requirement for the PssB protein (and perhaps PssA) for assembly of the EPS biosynthetic machinery. Similar to this observation, PelA, which also belongs to the carbohydrate esterase 4 superfamily, is necessary for Pel biosynthesis by *P. aeruginosa*. One enzyme critical for ManNAc-Gal EPS synthesis that so far has escaped identification is the α-galactosyl transferase that decorates the ManNAc chain.

In addition to biosynthesis proteins, the ManNAc-Gal EPS-specific glycosylhydrolase was identified and characterized. PssZ belongs to the GH8 family, whose members cleave β1-4 linkages through an inverting mechanism wherein carboxylate containing amino acid residues (i.e., Glu and Asp) perform the hydrolysis of glycosidic bonds. A conserved Glu residue present in the presumed catalytic site of PssZ was identified to be important for hydrolytic activity of PssZ (FIG. 17). The PssZ E72Q mutation largely, but not completely, abolished hydrolytic activity. This finding is consistent with the outcomes observed for mutations made in the similarly positioned Glu residues in the active sites of the cellulase BcsZ and endoglucanase K. This example also shows that exogenously added PssZ protein prevents listerial aggregation and disperses preformed cell aggregates (FIG. 17) but is inactive toward purified insoluble ManNAc-Gal EPS. A similar observation was reported for BcsZ, i.e., no hydrolytic activity was detected on carboxymethylcellulose in solution, whereas activity was shown on an agar plate containing carboxymethylcellulose. The soluble fragment of PssZ retains partial hydrolytic activity after 3 day incubation at 30° C. Given its relative stability, PssZ can be used for dispersing listerial EPS aggregates in food storage or processing plants, which would make *listeria* more susceptible to disinfectants. According to the results observed, listerial EPS-embedded aggregates are several orders of magnitude more tolerant to commonly used disinfectants than planktonic cells.

Without wishing to be bound by theory, it is believed ManNAc-Gal EPS biosynthesis in *L. monocytogenes* occurs according to the model illustrated in FIG. 19. According to this model, an unknown signal(s) induces the DGC activity of DgcA and/or DgcB, which may be physically associated with the Pss biosynthetic machinery. The locally generated c-di-GMP binds to the PssE receptor and stabilizes the PssE-PssC complex in a catalytically favorable conformation for ManNAc-Gal EPS synthesis. The c-di-GMP PDE, PdeC, possibly together with other PDEs, prevents nonspecific activation of the EPS synthesis via DgcC. During EPS synthesis, PssD assists the movement of the growing polysaccharide chain onto the cell surface, similar to the BcsB subunit of cellulose synthases. PssB may modify EPS through deacetylation, whereas PssZ periodically cleaves the ManNAc-Gal EPS chain to facilitate an unobstructed extrusion of the polymer and hydrolyzes it more rigorously for bacterial escape from aggregates.

Experimental Procedures

Bacterial Strains, Plasmids, and Growth Conditions

Bacterial strains, plasmids and their characteristics are listed in Table 4. *L. monocytogenes* EGD-e and derivatives of this strain were aerobically grown in brain hearth infusion (BHI) broth (Difco) with appropriate antibiotics, when needed, at 37° C. *Escherichia coli* DH5α (Invitrogen), S17-1 and BL21 (DE3) pLysS (Invitrogen) were used for cloning, conjugation, and protein purification experiments, respectively. These strains were routinely cultured in Luria-Bertani broth (LB) (Difco) with appropriate antibiotics. pKSV7, pIMK2, and pET23a vectors were used for construction of in-frame deletions in L. monocytogenes, protein overexpression in L. monocytogenes, and protein purifications in E. coli, respectively.

TABLE 4

Strains and plasmids used in this example ("His6" disclosed as SEQ ID NO: 4)

| Strain or plasmid | Description |
| --- | --- |
| Strains | |
| *Escherichia coli* | |
| DH5α | Strain for plasmid construction and maintenance |
| S17-1 | Strain for conjugative transformation of L. monocytogenes strains with pIMK2 constructs |
| BL21 [DE3] pLysS | Strain for protein purification |
| *Listeria monocytogenes* | |
| EGD-e | Wild-type (WT) |
| ΔpdeB/C/D | In-frame deletion of pdeB (lmo0131), pdeC (lmo1914) and pdeD (lmo0111) genes. High c-di-GMP and EPS overproducer |
| ΔpdeB/C/D ΔdgcA | In-frame deletion of dgcA in ΔpdeB/C/D |
| ΔpdeB/C/D ΔdgcB | In-frame deletion of dgcB in ΔpdeB/C/D |
| ΔpdeB/C/D ΔdgcC | In-frame deletion of dgcC in ΔpdeB/C/D |
| ΔpdeB/C/D ΔdgcA/B | In-frame deletion of the dgcA-dgcB locus in ΔpdeB/C/D |
| ΔpdeB/C/D ΔpssA | In-frame deletion of pssA in ΔpdeB/C/D |
| ΔpdeB/C/D ΔpssB | In-frame deletion of pssB in ΔpdeB/C/D |
| ΔpdeB/C/D ΔpssC | High c-di-GMP and impaired EPS production |
| ΔpdeB/C/D ΔpssD | In-frame deletion of pssD in ΔpdeB/C/D |
| ΔpdeB/C/D ΔpssE | High c-di-GMP and impaired EPS production |
| ΔpdeB/C/D ΔpssZ | In-frame deletion of pssZ in ΔpdeB/C/D |
| ΔpdeB/C/D ΔpssZ-pssZ | Complementation of ΔpssZ mutation by wild-type pssZ; ΔpdeB/C/D ΔpssZ ::pIMK2::pssZ |
| ΔpdeB/C/D ΔpssZ-pssZ E72Q | Complementation of ΔpssZ mutation by pssZ E72Q, ΔpdeB/C/D ΔpssZ ::pIMK2::pssZ E72Q |
| ΔpdeB/C/D-pIMK2 | Control strain for overexpression studies; ΔpdeB/C/D::pIMK2 |
| ΔpdeB/C/D-pssZ | Chromosomal overexpression of PssZ in ΔpdeB/C/D; ΔpdeB/C/D::pIMK2::pssZ |
| Plasmids | |
| pET23a | Plasmid for His6 tagged protein purification |
| pET23a-PssZ | pET23a::pssZ; PssZ-His6 overexpression plasmid |
| pET23a-PssZ E72Q | pET23a::pssZ E72Q; PssZ E72Q-His6 overexpression plasmid |
| pIMK2 | Vector for chromosomal expression in L. monocytogenes |
| pIMK2-pssZ | pIMK2::pssZ; chromosomal complementation with WT PssZ |
| pIMK2-pssZ E72Q | pIMK2::pssZ E72Q; chromosomal complementation with the single amino acid substitution copy of PssZ |
| pKSV7 | Vector for gene deletion in L. monocytogenes |
| pKSV7-ΔpssA | Plasmid for in-frame deletion of pssA |
| pKSV7-ΔpssB | Plasmid for in-frame deletion of pssB |
| pKSV7-ΔpssD | Plasmid for in-frame deletion of pssD |
| pKSV7-ΔpssZ | Plasmid for in-frame deletion of pssZ |

Bioinformatics Analysis

According to the Pfam database, L. innocua Lin2027 belongs to the GH8 family proteins, whereas PssZ (Lmo1913) is not recognized as a member of the GH8 family. In order to detect conserved residues in PssZ potentially involved in catalysis, the consensus sequence of GH8 proteins was aligned with the sequences of Lin2027 and PssZ. The phylogenetic analyses were performed as follows. Seed domain sequences were downloaded from phylogenetic trees in the Pfam domain database and aligned with the proteins of interest using Muscle (http://www.ebi.ac.uk/Tools/msa/muscle/). The Prot-Test server was utilized to predict models for protein evolution using multiple sequence alignments. Finally, phylogenetic trees were constructed according to the model of protein evolution for each multiple sequence alignment by the PhyML 3.0 server. Trees were visualized in the Dendroscope 3 program. The TMHMM Server v/2.0 was used for predicting protein membrane localization.

Purification of Cell-bound EPS

For EPS purification, the EPS overproducing ΔpdeB/C/D strain (Table 4), which lacks all listerial c-di-GMP PDE genes, pdeB, pdeC, and pdeD, was used. The ΔpdeB/C/D ΔpssC strain, in which the pssC gene encoding a glycosyltransferase was deleted, is impaired in EPS production and was used as a negative control. Listerial EPS was purified according to known procedures with the following modifications. An overnight ΔpdeB/C/D BHI culture was transferred to 1 l of Hsiang-Ning Tsai medium supplemented with 3% (wt/v) glucose (HTM/G) (5×200 ml in 2 l flasks) at an OD600 of 0.01 and incubated with gentle shaking (125 rpm) at 30° C. for 48 h. Both dispersed cells and aggregates were collected by centrifugation (5,000 rpm, 15 min, 4° C.) and resuspended in 20 ml deionized water. The cell suspension was boiled for 5 min and centrifuged (15,000 rpm, 45 min, 4° C.). The supernatant was collected and precipitated with 4 volumes of cold (4° C.) ethanol overnight at 4° C. After washing the precipitant with water, the sample was treated with lysozyme (4 mg ml$^{-1}$; Sigma), mutanolysin (25 μg ml$^{-1}$; Sigma), DNase I (0.5 mg ml$^{-1}$; Sigma) and RNase A (0.5 mg ml$^{-1}$; Qiagen) at 37° C. for 24 h. Following enzymatic digestion, the insoluble fraction was collected by centrifugation, washed with water, and dried at 41° C.

Purification of Extracellular Carbohydrates

Culture supernatants of HTM/G-grown cultures of the ΔpdeB/C/D and ΔpdeB/C/D ΔpssC strains were collected and precipitated overnight with cold ethanol. After resuspension, pellets were digested with lysozyme and mutanolysin as described above. The protein and nucleic acid contaminants were removed from the preparations by trichloroacetic acid (TCA) (Sigma-Aldrich) (20%, final TCA concentration) precipitation. After removal of the insoluble material by centrifugation (15,000 rpm, 1 h, 4° C.), cold ethanol was used to precipitate water-soluble carbohydrates. The precipitate was solubilized in deionized water and extensively dialyzed against deionized water over 24 h. Carbohydrate samples were lyophilized and stored at −80° C. prior to NMR analysis.

Total Carbohydrate Content Determination

Total carbohydrates were determined using an anthrone assay. Dried EPS samples were transferred to 0.4 ml of water and mixed with an ethyl acetate solution containing anthrone reagent (2% w/v). Then, 1 ml of concentrated sulfuric acid was added to the mixture for color development. Samples were read at a wavelength of 620 nm, and glucose was used as a standard to estimate carbohydrate levels in the samples. Finally, dried EPS samples were sent to the Complex Carbohydrate Research Center (Athens, Ga., USA) for determination of monosaccharide composition, linkage, and NMR analysis.

NMR Spectroscopy of Extracellular Soluble Carbohydrates

Extracellular soluble carbohydrate samples from the ΔpdeB/C/D and ΔpdeB/C/D ΔpssC strains were dissolved in 650 μL D$_2$O (99.9% d, Sigma-Aldrich). Samples in H$_2$O were prepared in a 10% D$_2$O/90% H$_2$O mixture to a total volume of 650 μL. Reference samples were prepared by dissolving the standards N-acetyl-D-glucosamine and L-rhamnose in $D_2O$ to final volumes of 650 μL and final concentrations of 50 mM.

NMR spectra were collected at 600 MHz in a BrukerAvance II 600 spectrometer (Bruker BioSpin Corp, Billerica, Mass., USA) with a 5.0 mm multi-nuclear broad-band observe probe. All NMRspectra were collected at 298 K. Solvent suppression for all samples was performed using a pre-saturation sequence incorporated into the one- (1D) and two-dimensional (2D) experiments. 1D spectra were obtained using a 12 μs 90° pulse with 32 K data points. 2D total correlation spectroscopy (TOCSY) experiments for samples in $D_2O$ and $H_2O$ were recorded with an 80 ms mixing time, 512 t1 points and 2,048 complex points for each free induction decay.

Processing and analysis of the 2D NMR data were performed using NMRPipe, NMRViewJ, and Topspin 3.0 (Bruker BioSpin Corp, Billerica, Mass., USA) software. Spectra were Fourier transformed using Lorentzian-to-Gaussian weighting and phase shifted sine-bell window functions.

NMR Spectroscopy of Cell Surface-bound Insoluble EPS

N-deacetylation was performed to obtain soluble EPS material for NMR studies. The insoluble EPS sample was suspended in 300 μl of 50% NaOH and heated to 80° C. for 1 h. After cooling to room temperature, the sample was diluted with 1 ml of water and acidified with glacial acetic acid (final pH~4-5). The sample was dialyzed against running deionized water for 36 h using a 3,500 Da regenerated cellulose membrane and lyophilized. This material was designated 'EPS-N'. EPS-N was dissolved in 5 ml of 0.4 M HCl and heated at 110° C. for 2 h for partial hydrolysis. After cooling to room temperature, the sample was dialyzed twice against 4 l deionized water (6 h and 24 h, respectively) using a 1,000 Da regenerated cellulose membrane and then lyophilized. This material was designated 'EPS-H'.

To determine 1JCH coupling constants for both α- and β-anomers, mannosamine hydrochloride was synthesized. Briefly, 40 mg N-acetylmannosamine was dissolved in 300 μl 2.4 M HCl and heated in a sealed tube for 5 h at 100° C. The mixture was dried with a stream of nitrogen, dissolved in $D_2O$, and lyophilized. For NMR, the sample was dissolved in 700 μl $D_2O$.

The samples were deuterium exchanged by dissolving in 20 mM DCl in $D_2O$ and lyophilization and were subsequently dissolved in 0.27 ml of 20 mM DCl in $D_2O$. 1-D proton and 2-D COSY, TOCSY, NOESY, HSQC spectra were obtained on a Varian Inova-600 MHz spectrometer (Agilent Technologies, Santa Clara, Calif., USA) at 50° C. using standard Varian pulse sequences. The spectral window was from 5.76 to 1.07 ppm (2815 Hz) in the proton dimensions and from 120 to 40 ppm (1263 Hz) in the carbon dimension. Scan/increment combinations were 4/400 (COSY), 8/128 (TOCSY), 400/80 (HSQC) and 16/128 (NOESY) for EPS-N and 8/400 (COSY), 16/128 (TOCSY), 128/80 (HSQC) and 16/128 (NOESY) for EPS-H. Mixing times were 80 ms for TOCSY and 300 ms for NOESY. The HSQC experiment without decoupling during acquisition for the determination of 1JCH coupling constants was acquired with a spectral window of 110-90 ppm (3,017 Hz) in 16 increments of 256 scans each. The spectra were processed using the MNova NMR software. Line fitting was performed in MNova using a Lorentzian-Gaussian line shape type and simulated annealing with a maximum number of 500 coarse and 100 fine iterations. Proton chemical shifts were measured relative to an internal acetone standard (611H=2.218 ppm, δC=33.0 ppm).

Phenotypic Assays

Cell aggregation analysis was carried out at 30° C. with gentle shaking (125 rpm) for 48 h in HTM/G using overnight BHI cultures to inoculate HTM/G cultures at an OD600 level of 0.01. The extent of cell aggregation was also determined by measuring the reduction in OD600 values of HTM/G cultures standing for 2 min periods. To visualize EPS production by *L. monocytogenes* strains, overnight BHI cultures were streaked on HTM/G with 40 μg/ml Congo red dye (Sigma) and incubated at 30° C. for 48 h.

Scanning Electron Microscopy (SEM)

The EPS overproducer strain ΔpdeB/C/D, the EPS negative strain ΔpdeB/C/D ΔpssC, and the wild-type strain EGD-e grown in HTM/G media were mounted on polylysine-treated microscope slides (Thermo Scientific). SEM samples were prepared according to known methods with minor modifications. Briefly, cells were fixed with 3% gluteraldehyde and 0.1% ruthenium red in PBS at room temperature for 2 h. After washing three times with PBS, cells were dehydrated in 50 ml of a series of 30, 50, 60, 70, 90 and 95% ethanol solutions for 10 min at each dilution. The dehydration steps were completed by immersing slides three times in 100% ethanol for 10 min. Cells were then subjected to critical point drying and immediately coated with gold. SEM images of cells were acquired in HV mode using an accelerating voltage of 20 kV, a spot size of 3, and a working distance of 11 mm on a Quanta FEG MK2 Scanning Electron Microscope (FEI, Eindhoven, The Netherlands).

Construction of In-frame Deletion Strains

The EPS synthesis genes pssA, pssB, and pssD in the pssA-E operon, pssZ, a gene encoded within a c-di-GMP signaling module (dgcA-dgcB-pssZ-pdeC), and three DGCs (dgcA, dgcB and dgcC) were deleted in-frame in the ΔpdeB/C/D strain using the splice-by-overlap extension PCR method. Briefly, two 400 bp fragments flanking and overlapping the coding regions at the 5' and 3' ends of the gene of interest were amplified and combined by PCR amplifications using EGD-e genomic DNA, Pfu Turbo DNA polymerase (Agilent), and primers listed in Table 5.

TABLE 5

Primers used (SEQ ID NOS 7-46, respectively, in order of appearance)

| | | |
|---|---|---|
| In-frame deletion | pssA.PA | gggctgcagaatttgttgtaa tttgtcgaca |
| | pssA.PB | ttacgcattccgctcaccgga tttaactttccttatcat |
| | pssA.PC | ggtgagcggaatgcgtaa |
| | pssA.PD | gggggatccagaagcatctgt aattgcttt |
| | pssB.PA | gggctgcagaaactttgaaaa ggcgacag |
| | pssB.PB | atatttcttcatgtaaagccg aatacttataatcattttta cg |
| | pssB.PC | cggctttacatgaagaaatat |
| | pssB.PD | gggggatccgcctgtaatatt atcggtatt |
| | pssD.PA | gggctgcagtaggcgcgttcg ctttga |
| | pssD.PB | gctccggcgatatttacgcag ccacattacagtaaattt |
| | pssD.PC | cgtaaatatcgccggagc |
| | pssD.PD | gggggatcctttcgtgttttc ttcttgaag |

TABLE 5-continued

Primers used (SEQ ID NOS 7-46, respectively, in order of appearance)

| | | |
|---|---|---|
| | pssZ.PA | gggctgcagaaagaaataatt tgattttcatgg |
| | pssZ.PB | ttatttcttaagagttatttc tttaattaggatgaatcgttt cat |
| | pssZ.PC | aaagaaataactcttaagaaa taa |
| | pssZ.PD | ggggtcgacaaagaaataaat gattttcatgg |
| | dgcA.PA | gatcacctgcagccgtcctgt atctccttcgactc |
| | dgcA.PB | gcgaatatgtacttgcgccat gctgttccataatgaatcaag |
| | dgcA.PC | tggaacagcatggcgcaagta catattcgcgaaacagaacca g |
| | dgcA.PD | tcgatagaattcgcagttaca aagaacagcaagaaatactcg |
| | dgcB.PA | gatcacctgcagcctttgatg ctgcattcaaccatg |
| | dgcB.PB | ctgatgaacagcaatattttg gaaccaattagggcgatatgt c |
| | dgcB.PC | aattggttccaaaatattgct gttcatcagggggaac |
| | dgcB.PD | tcgatagaattctctgttgca ttgcttggatatttagatagc |
| | dgcC.PA | atagatctgcagcggcatctg gaatggggcaacaaattgc |
| | dgcC.PB | taacgttctagacaactgttc gaccaaaaagcatc |
| | dgcC.PC | attgcatctagagtatgtatt gcagacggaaattagtctg |
| | dgcC.PD | gtcataggtacccttacctcg ccagtttcaagcactcg |
| | dgcAB.PA | atcgatctgcaggaaattcgc taaaattaagttctagc |
| | dgcAB.PB | gctctaggatccccataatga atcaagaatatttggc |
| | dgcAB.PC | cgagatggatccgaactcgaa tgaaacgattcatc |
| | dgcAB.PD | atctcggaattctacggaggg cttttcatttgtc |
| Chromosomal expression | pssZ.FP | gggccatggggatgaaacgat tcatcctaatt |
| | pssZ.RP | gggctgcagttatttcttaag agttatttctttatt |
| | pssZ::E72Q.PA | gggccatggggatgaaacgat tcatcctaatt |
| | pssZ::E72Q.PB | catataaagtccaatgctctg ggctagatagtggggttc |
| | pssZ::E72Q.PC | cagagcattggactttatatg |
| | pssZ::E72Q.PD | gggctgcagttatttcttaag agttatttctttt |
| PssZ and PssZ E72Q purification | FP | ggggctagccgaccagagtct aaaaag |
| | RP | gggaagcttttcttaagagt tatttctttatt |

The resulting 800 bp DNA in-frame deletion fragments and the suicide shuttle vector pKSV7 were digested with PstI and BamHI (New England Biolabs) and ligated with T4 DNA ligase (New England Biolabs) overnight at 18° C. The resulting deletion constructs were introduced into and maintained in DH5α and were subsequently transferred to *L. monocytogenes* strains via electroporation. To insert the constructs via homologous recombination, four consecutive passages were carried out at 41° C. in the presence 10 μg ml$^{-1}$ of chloramphenicol. To excise the vector from the chromosome, six to eight passages were performed at 30° C. with no antibiotics. Revertants (wild-type or deletion mutants) were screened for on BHI agar plates supplemented with 10 μg ml$^{-1}$ chloramphenicol. In-frame deletion mutants were identified by colony PCR analysis of chloramphenicol sensitive clones.

Construction of PssZ Chromosomal Expression Mutants

The pssZ gene was introduced into the ΔpdeB/C/D and ΔpdeB/C/D ΔpssZ strains for overexpression and complementation purposes, respectively. A DNA fragment prepared by PCR amplification encoding pssZ was digested with NcoI and BamHI (New England Biolabs) and ligated into the pIMK2 expression vector digested with the same restriction enzymes. This expression construct, pIMK2-pssZ, was transformed into *E. coli* S17-1 strain, which was used in conjugation with the *L. monocytogenes* strains. Briefly, *L. monocytogenes* strains (recipients) and S17-1 harboring the expression construct (donor) were grown in BHI and LB with 50 μg ml$^{-1}$ kanamycin, respectively, overnight at 37° C. Overnight cultures were diluted in fresh medium and grown until the OD600 reached 0.5. The donor (2.5 ml) and recipient (1.5 ml) cultures were mixed, centrifuged, washed to eliminate kanamycin, and the final pellets were resuspended in 25 μL BHI and spotted on BHI agar plates. After 24 h of incubation at 30° C., the conjugation mixtures were resuspended in PBS and plated on BHI agar plates supplemented with 100 μg ml$^{-1}$ nalidixic acid and 50 μg ml$^{-1}$ kanamycin. Transformed strains with the chromosomal expression construct were observed after 48 h of incubation at 30° C. pIMK2::pssZ::E72Q was introduced into *L. monocytogenes* genomes using the same procedure as pIMK2::pssZ.

Purification of PssZ Proteins

The glycosylhydrolase activity against listerial EPS was tested in vitro using purified PssZ and PssZ E72Q proteins. Primers were designed to exclude the transmembrane domains from the N-terminal ends of the proteins and add C-terminal His6-tags (SEQ ID NO: 4) (Table 5). The pssZ and pssZ::E72Q genes were cloned into pET23a using NheI and HindIII sites and transformed into BL21 (DE3) pLysS. The two proteins were purified by a batch method using Ni-NTA affinity resin from 100 ml of LB medium supplemented with 100 μg ml$^{-1}$ ampicillin and 25 μg ml$^{-1}$ chloramphenicol after induction with 0.1 mM IPTG for 3 h at room temperature. Following induction, cells were harvested, resuspended in a binding buffer [20 mM sodium phosphate, 0.5 M NaCl and 20 mM imidazole, protease inhibitor cocktail (Roche), pH 7.4], and lysed via French Press disruption and sonication. Cleared lysates were loaded onto Ni-NTA resin, incubated at 4° C. overnight, washed, and eluted (20 mM sodium phosphate, 0.5 M NaCl and 250 mM imidazole, pH 7.4). Fractions with recombinant proteins were desalted with Thermo Scientific Zeba Spin Desalting Columns and concentrated with Amicon Ultra Centrifugal Units (30 kDa cutoff). Final concentrates were filter sterilized using a 0.2 μm syringe filter (Life Sciences). Final protein preparations were analyzed by sodium dodecyl sulfate polyacrylamide gel electrophoresis, and concentrations were determined by a Bio-Rad protein assay using BSA standard.

Glycosylhydrolase Activity Assays

The EPS hydrolytic activities of PssZ and PssZ E72Q were assessed by the ability of these proteins: (i) to prevent aggregation of the growing ΔpdeB/C/D strain in HTM/G medium, (ii) to disperse nongrowing ΔpdeB/C/D aggregates; and (iii) to release soluble carbohydrates from the purified insoluble EPS fibers. (i) Different concentrations (0.13 and 1.3 μg ml$^{-1}$) of the purified PssZ and PssZ E72Q proteins were added at the beginning of strain incubation. (ii) Aggregates were washed twice and resuspended in HTM salts-MOPS medium. Proteins were added to 1 ml of aggregate suspension (32 µg ml⁻¹, final concentration), and samples were incubated at 30° C. with gentle shaking. The turbidity of the samples was used as an indication of cell dispersion. (iii) Purified EPS fibers were incubated with PssZ or PssZ E72Q at 32 µg ml⁻¹ (final concentration). Released soluble carbohydrates were assayed using the anthrone reaction.

Example III

This Example describes methods for identifying and producing PssZ homologs.

Proteins homologous to *L. monocytogenes* PssZ are present in diverse bacteria, including extremophiles capable of living at temperatures from −10° C. to 65° C. Some of these bacteria live at high salinity (up to 20% [w/v] NaCl) and alkalinity (up to pH 9). *L. monocytogenes* PssZ is located on the outer surface of bacteria where PssZ hydrolyzes Pss exopolysaccharide. The PssZ homologs likely function in a similar manner, therefore they can be predicted to withstand the pH and salinity of environment. The relatively high percent sequence similarity among PssZ homologs indicates that the PssZ homologs are suitable for hydrolyzing listerial Pss exopolysaccharide at the temperatures, salinity, and pH in which their hosts can grow. These PssZ proteins can therefore be used for hydrolyzing listerial EPS-coated aggregates and for preventing formation of such aggregates in cleaning and washing solutions at the temperatures ranging from sub-zero to 65° C., salinity from 0 to 20% [w/v] NaCl, and alkaline conditions up to pH 9.0 or higher.

Examples of selected PssZ homologs from representative bacteria with desirable properties are shown below (as BLAST alignments to PssZ).

```
1. Exiguobacterium undae, a psychrophile isolated from a lake in Antarctica.
                                                              [SEQ ID NO: 47]
    1       mfmtrqqdpv iggvetvymk egliraydre eaqrlseslg qymvylleig dadrfaeqvd 61       ilrkqflvtt eegdfikwel tpktatnaiv ddfrisnalf aaakrfdepd yqqlsrridd 121       givehmkvsg vpidfydwnl kmqtnelrin yldatalkrl nlvepvqevl qaaprsgpff 181       heiylpedkr yktaddkevn midgaliaiv seeltgqqde afyafidqem kkgklyaryd 241       rstasprsdd esssvyalll pyvseevqrk mterldgidl tdaatthvfd ylneaiarvq 301       tsmpnk
(referred to herein as Exiguobacterium undae PssZ)

>ref|WP_051523998.1| hypothetical protein [Exiguobacterium undae]
Length = 306
Score = 206 bits (525), Expect = 4e-60, Method: Compositional matrix adjust.
Identities = 122/309 (39%), Positives = 186/309 (60%), Gaps = 27/309 (9%)
(SEQ ID NOS 48 and 49, respectively, in order of appearance)
Query     34      KETTPTSTSVQT-YVKENYTAKNGLIMDYKNTEEPHYLAESIGLYMEYLVEVNDSKTFQK    92
                  ++  P     V+T Y+KE      GLI  Y + EE    L+ES+G YM YL+E+ D+  F +
Sbjct      5      RQQDPVIQQVETVYMKE------GLIRAY-DREEAQRLSESLGQYMVYLLEIGDADRFAE     57

Query     93      QVNHLEKYFIA---EDNFIKWEATDSTTTNAIVDDFRITEALYQASEKFSFPSYKKMADK   149
                  QV+ L K F+    E +FIKWE T  T TNAIVDDFRI+ AL+ A+++F  P Y++++ +
Sbjct     58      QVDILRKQFLVTTEEGDFIKWELTPKTATNAIVDDFRISNALFAAAKRFDEPDYQQLSRR    117

Query    150      FLTNTKKYSAEQGVPVDFYDFVHKKKADTLHLSYLNIQAMQQINYRDKAYLPIQTI----   205
                          ++    GVP+DFYD+  K + L L+YL+  A++++N    +   P+Q  +
Sbjct    118      IDDGIVEHMKVSGVPIDFYDWNLKMQTNELRLNYLDATALKRLNLVE----PVQEVLQAA   173

Query    206      -NADPFFTEVF--QNGQFKFADQKEVNMIDQMLIAIAYYDENGDIEPNFDNFLQTELASK   262
                   + PFF E++  ++ ++K AD KEVNMIDQ LIAI   G   F  F+  E+    K
Sbjct    174      PRSGPFFHEIYLPEDKRYKTADDKEVNMIDQALIAIVSEELTGQQDEAFYAFIDQEM-KK   232

Query    263      GKIYARYQRETKKPSSENESTAVYAFLTQYFNKTNQAKNGKITKELLEKMDTSNPETTHF   322
                  GK+YARY R T  P S++ES++VYA L  Y ++    Q K       E L+++D ++  TTH
Sbjct    233      GKLYARYDRSTASPRSDDESSSVYALLLPYVSEEVQRK----MTERLDQIDLTDAATTHV   288

Query    323      FDYINKEIT                                                     331
                  FDY+N+ I
Sbjct    289      FDYLNEAIA                                                     297

2. Carnobacterium mobile, a psychrophile isolated from Siberian permafrost.
                                                              [SEQ ID NO: 50]
    1       mnkkrfylil vlillissll alsfhqkigv qevvnnkyen nkgliknyak ngkvqylses 61       igqylsylll vedekefkqq vavlkknflv kqadgtfiqw vatnqtttna svddfriiav 121       lkkaseqfqe payqiladel eetliskqlt dglivdfydw elqkkaavlh lsyiddqiik 181       tdskvnkaky qkilmesvds dtpffkevyt leeqtyqlad kksvnlidql miaiqyvklt 241       nqtpaqfdqw lkaewdangk ffggylrtdl tpavpyessa vyalatlyfk lvheeayaeq 301       lhqvllkqsp fdknadyati hffdymwvkt vdvlykkdli dk
(referred to herein as Carnobacterium mobile PssZ)
```

```
>ref|WP_051929818.1| hypothetical protein [Carnobacterium mobile]
Length = 342
Score = 182 bits (463), Expect = 2e-50, Method: Compositional matrix adjust.
Identities = 112/298 (38%), Positives = 168/298 (56%), Gaps = 13/298 (4%)
(SEQ ID NOS 51 and 52, respectively, in order of appearance)
Query      42      SVQTYVKENYTAKNGLIMDYKNTEEPHYLAESIGLYMEYLVEVNDSKTFQKQVNHLEKYF   101
                   VQ  V   Y    GLI +Y     + YL+ESIG Y+ YL+ V D K F++QV  L+K F
Sbjct      29      GVQEVVNNKYENNKGLIKNYAKNGKVQYLSESIGQYLSYLLLVEDEKEFKQQVAVLKKNF    88

Query     102      I---AEDNFIKWEATDSTTTNAIVDDFRITEALYQASEKFSFPSYKKMADKFLTNTKKYS   158
                   +    A+  FI+W AT+ TTTNA VDDFRI   L +ASE+F  P+Y+ +AD+
Sbjct      89      LVKQADGTFIQWVATNQTTTNASVDDFRIIAVLKKASEQFQEPAYQILADELEETLISKQ   148

Query     159      AEQGVPVDFYDFVHKKKADTLHLSYLNIQAMQ---QINYRDKAYLPIQTINAD-PFFTEV   214
                     G+ VDFYD+  +KKA  LHLSY++ Q  ++    ++N      +  ++++++D PFF EV
Sbjct     149      LTDGLIVDFYDWELQKKAAVLHLSYIDDQIIKTDSKVNKAKYQKILMESVDSDTPFFKEV   208

Query     215      F--QNGQFKFADQKEVNMIDQMLIAIAYYDENGDIEPNFDNFLQTELASKGKIYARYQRE   272
                   +  +    ++ AD+K VN+IDQ++IAI Y        FD +L+  E  + GK + +Y R
Sbjct     209      YTLEEQTYQLADKKSVNLIDQLMIAIQYVKLTNQTPAQFDQWLKAEWDANGKFFGGYLRT   268

Query     273      TKKPSSENESTAVYAFLTQYFNKTNQAKNGKITKELLEKMD----TSNPETTHFFDYI    326
                   P+    ES+AVYA  T YF  ++     + ++L K         ++  T HFFDY+
Sbjct     269      DLTPAVPYESSAVYALATLYFKLVHEEAYAEQLHQVLLKQSPFDKNADYATIHFFDYM    326

3. Carnobacterium jeotgali, a bacterium able to grow at 4-37° C., at pH 5.5-9.0
and in the presence of 0-5% (w/v) NaCl.
                                                                        [SEQ ID NO: 53]
   1     mskkrffmil lvillitilt llfsynkrev qeviennykn ddnliknyak nnqieylses 61     tggylyylll vkdekefkgq vdslknnfiv krsdgtyikw ttsdqtttna svddfriiev 121     lrkggkyfge pdyvilanel eetlnskqlt dglivdfydw elqkkattvh lsyindqiik 181     gnarvdpady qkllagstns qnpffkeiyt vdkhsylsad kntvnmidqf miaigylkfm 241     nqvppefdqw vkqewdtngk lfggyvkstr tpavpyessa vyalaylyfk qaneekyade 301     lyamiltqps fdknpdyski hffdyiwiet anaiyktrdk tq
(referred to herein as Carnobacterium jeotgali PssZ)

>ref|WP_029276582.1| hypothetical protein [Carnobacterium jeotgali]
Length = 342
Score = 172 bits (435), Expect = 2e-46, Method: Compositional matrix adjust.
Identities = 110/301 (37%), Positives = 164/301 (54%), Gaps = 21/301 (7%)
(SEQ ID NOS 54 and 55, respectively, in order of appearance)
Query      43      VQTYVKENYTAKNGLIMDYKNTEEPHYLAESIGLYMEYLVEVNDSKTFQKQVNHLEKYFI   102
                   VQ  ++ NY    + LI +Y       + YL+ES G Y+ YL+ V D K F++QV+ L+  FI
Sbjct      30      VQEVIENNYKNDDNLIKNYAKNNQIEYLSESTGQYLYYLLLVKDEKEFKQQVDSLKNNFI    89

Query     103      ---AEDNFIKWEATDSTTTNAIVDDFRITEALYQASEKFSFPSYKKMADKFLTNTKKYSA   159
                       ++  +IKW +D TTTNA VDDFRI  E L +  + F  P Y  +A++
Sbjct      90      VKRSDGTYIKWTTSDQTTTNASVDDFRIIEVLRKGGKYFQEPDYVILANELEETLNSKQL   149

Query     160      EQGVPVDFYDFVHKKKADTLHLSYLNIQAMQQINYRDKA----YLPIQTINADPFFTEVF   215
                     G+ VDFYD+  +KKA T+HLSY+N Q  ++        D A       L  T  +PFF E++
Sbjct     150      TDGLIVDFYDWELQKKATTVHLSYINDQIIKGNARVDPADYQKLLAGSTNSQNPFFKEIY   209

Query     216      QNGQFKF--ADQKEVNMIDQMLIAIAYYDENGDIEPNFDNFLQTELASKGKIYARYQRET   273
                   +   +  +   AD+   VNMIDQ +IAI Y      + P FD +++ E  + GK++  +Y + T
Sbjct     210      TVDKHSYLSADKNTVNMIDQFMIAIQYLKFMNQVPPEFDQWVKQEWDTNGKLFGGYVKST   269

Query     274      KKPSSENESTAVYAFLTQYFNKTNQAKNGK------ITKELLEKMDTSNPETT--HFFDY   325
                   + P+    ES+AVYA   YF + N+ K        +T+   +K    NP+ +   HFFDY
Sbjct     270      RTPAVPYESSAVYALAYLYFKQANEEKYADELYAMILTQPSFDK----NPDYSKIHFFDY   325

Query     326      I                                                            326
                   I
Sbjct     326      I                                                            326

4. Jeotgalibacillus campisalis, a halophilic bacterium capable of growth in the
presence of 0-20% (w/v) NaCl.
>ref|WP_041061425.1| hypothetical protein [Jeotgalibacillus campisalis]
Length = 304
Score = 155 bits (393), Expect = 1e-40, Method: Compositional matrix adjust.
Identities = 112/290 (39%), Positives = 151/290 (52%), Gaps = 14/290 (5%)
                                                                        [SEQ ID NO: 56]
   1     mfstdptlqv vkegytngeg lihayplqqd seylsesigl ymeylvlvkd eerfseqyei 61     lmnnyqiqqg dlifigwvlk mntkanalid dvriisalhd astlfeepky aesanqltla
```

```
121      itsnqksngy tvdfydwsln mpakritlsy ltneffqstt dtdnmkdllk nlddttvffp 181      eyfdvtkrky reseevhmid qlliainren igypseifkt wclnewkheg kiygrydrqt 241      ktasvtyesl avyyylntyf qkinepdlak evlehaella sestigeahf fdyihfqlmk 301      knme
```
(referred to herein as *Jeotgalibacillus campisalis* PssZ)
(SEQ ID NOS 57 and 58, respectively, in order of appearance)

```
Query    47    VKENYTAKNGLIMDYKNTEEPHYLAESIGLYMEYLVEVNDSKTFQKQVNHL-EKYFIAED  105
               VKE YT + GLI  Y    ++  YL+ESIGLYMEYLV V D + F +Q    L   Y I +
Sbjct    11    VKEQYTNQEGLIHAYPLQQDSEYLSESIGLYMEYLVLVKDEERFSEQYEILMNNYQIQQG   70

Query    106   N--FIKWEATDSTTTNAIVDDFRITEALYQASEKFSFPSYKKMADKFLTNTKKYSAEQGV  163
               +  FI+W     +T  NA++DD RI  AL+ AS  F   P Y + A++          G
Sbjct    71    DLIFIQWVLKMNTKANALIDDVRIISALHDASTLFEEPKYAESANQLTLAITSNQKSNGY  130

Query    164   PVDFYDFVHKKKADTLHLSYLNIQAMQQINYRDKAYLPIQTI-NADPFFTEVFQNGQFKF  222
               VDFYD+     A  + LSYL  +  Q     D    ++ + +   FF E F   + K+
Sbjct    131   TVDFYDWSLNMPAKRITLSYLTNEFFQSTTDTDNMKDLLKNLDDTTVFFPEYFDVTKRKY  190

Query    223   ADQKEVNMIDQMLIAIAYYDEN-GDIEPNFDNFLQTELASKGKIYARYQRETKKPSSENE  281
               + +EV+MIDQ+LIAI    EN G     F  + E    +GKIY RY R+TK   S   E
Sbjct    191   RESEEVHMIDQLLIAIN--RENIGYPSEIFKTWCLNEWKHEGKIYGRYDRQTKTASVTYE  248

Query    282   STAVYAFLTQYFNKTNQAKNGKITKELLEKMDTSNPETT----HFFDYIN           327
               S AVY +L  YF K N+      + KE+LE  +     E+T     HFFDYI+
Sbjct    249   SLAVYYYLNTYFQKINEP---DLAKEVLEHAELLASESTIGEAHFFDYIH           295
```

5. *Bacillus thermotolerans*, a thermophilic bacterium capable of growth up to 65° C. and pH 6.0-9.0.
>gb|KKB33529.1| hypothetical protein QY97_03202 [*Bacillus thermotolerans*]
gb|KKB35790.1| hypothetical protein QY95_03280 [*Bacillaceae bacterium* MTCC 8252]
Length = 298
Score = 108 bits (269), Expect = 2e-23, Method: Compositional matrix adjust.
Identities = 84/258 (33%), Positives = 122/258 (47%), Gaps = 30/258 (12%)

[SEQ ID NO: 59]
```
  1      mqkdteaaws eeefirivhq yymddsgkir sygteeneey llesmglymk wlsghnreee 61      vgelrktvqs efayehasdv flswrvegdq qasvnawidd arilsvlgpa dplfnkiadt 121      lkkyqvqngl ivdfydweqe aaservvlsy gtreedalrl tsmdrlylea strsdpfype 181      fydvkekkfi esdevhmvdq lliaiqleke kgdnhefwqw lvsewekhqa isgrydrnsh 241      kgngiesgav ygiaaewall kgeeelaekw khkgfqlvnp kdhqfdhihf fdliwnap
```
(referred to herein as *Bacillus thermotolerans* PssZ) (SEQ ID NOS 60 and 61, respectively, in order of appearance)

```
Query    47    VKENYTAKNGLIMDYKNTEEPHYLAESIGLYMEYLVEVNDSKTFQKQVNHLEKYFI---A  103
               V + Y  +G I  Y    E     YL ES+GLYM++L  N  + Q+     ++ F   A
Sbjct    18    VHQYYMDDSGKIRSYGTEENEEYLLESMGLYMKWLSGHNREEEVQELRKTVQSEFAYEHA   77

Query    104   EDNFIKW--EATDSTTTNAIVDDFRITEALYQASEKFSFPSYKKMADKFLTNTKKYSAEQ  161
                D F+ W  E      + NA +DD RI   L  A      P + K+AD     KKY +
Sbjct    78    SDVFLSWRVEGDQQASVNAWIDDARILSVLGPAD-----PLFNKIADTL----KKYQVQN  128

Query    162   GVPVDFYDFVHKKKADTLHLSY-------LNIQAMQQINYRDKAYLPIQTINADPFFTEV  214
               G+ VDFYD+   +  ++ + LSY       L + +M     D+ YL  T +DPF+ E
Sbjct    129   GLIVDFYDWEQEAASERVVLSYGTREEDALRLTSM------DRLYLEAST-RSDPFYPEF  181

Query    215   FQNGQFKFADQKEVNMIDQMLIAIAYYDENGDIEPNFDNFLQTELASKGKIYARYQRETK  274
               +   + KF + +  EV+M+DQ+LIAI     E GD   F  +L +E       I  RY R +
Sbjct    182   YDVKEKKFIESDEVHMVDQLLIAIQLEKEKGD-NHEFWQWLVSEWEKHQAISGRYDRNSH  240

Query    275   KPSSENESTAVYAFLTQY                                           292
               K +   ES AVY       ++
Sbjct    241   KGNG-IESGAVYGIAAEW                                           257
```

Example IV

This Example describes methods of producing a PssZ enzyme or a polysaccharide in an isolated and substantially purified form.

In nature, both the polysaccharide and the PssZ enzyme degrading it are bound to a living *L. monocytogenes* cell surface. In contrast, the PssZ enzyme for use in embodiments of the invention is provided without viable *L. monocytogenes* cells, and preferably in a purified form.

In an embodiment, the PssZ coding sequence from *L. monocytogenes* is expressed in a host cell, such as *E. coli*. A feature of embodiments of the invention is the expression of the sequences encoding PssZ. As is well-known in the art, DNA sequences may be expressed by operatively linking them to an expression control sequence in an appropriate expression vector and employing that expression vector to transform an appropriate host cell.

A coding sequence is operatively linked to an expression control sequence when the expression control sequence controls and regulates the transcription and translation of that coding sequence. The term expression control sequences refer to DNA sequences that control and regulate the transcription and translation of another DNA sequence (i.e., a coding sequence). Expression control sequences include, but are not limited to, promoters, enhancers, promoter-associated regulatory sequences, transcription termination and polyadenylation sequences, and their positioning and use is well understood by the ordinary skilled artisan. The term "operatively linked" includes having an appropriate start signal (e.g., ATG) in front of the DNA sequence to be expressed, and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene. The combination of the expression control sequences and the PssZ coding sequence form a PssZ expression cassette.

As used herein, an exogenous or heterologous nucleotide sequence is one which is not in nature covalently linked to a particular nucleotide sequence, e.g., an PssZ coding sequence. Examples of exogenous nucleotide sequences include, but are not limited to, plasmid vector sequences, expression control sequences not naturally associated with particular PssZ coding sequences, and viral or other vector sequences. A non-naturally occurring DNA molecule is one which does not occur in nature, and it is thus distinguished from a chromosome, for example. As used herein, a non-naturally occurring DNA molecule comprising a sequence encoding an expression product with PssZ activity is one which comprises said coding sequence and sequences which are not associated therewith in nature.

Similarly, as used herein an exogenous gene is one which does not naturally occur in a particular recombinant host cell but has been introduced in using genetic engineering techniques well known in the art. An exogenous gene as used herein can comprise a PssZ coding sequence expressed under the control of an expression control sequence not associated in nature with said coding sequence.

A wide variety of host/expression vector combinations may be employed in expressing the DNA sequences of this invention. Useful expression vectors, for example, may consist of segments of chromosomal, nonchromosomal, and synthetic DNA sequences. Suitable vectors include derivatives of SV40 and known bacterial plasmids, e.g., *Escherichia coli* plasmids colE1, pCR1, pBR322, pMB9, and their derivatives, plasmids such as RP4; phage DNAs, e.g., M13 derivatives, the numerous derivatives of phage λ, e.g., Agt11, and other phage DNA; yeast plasmids derived from the 2µ circle; vectors useful in eukaryotic cells, such as insect or mammalian cells; vectors derived from combinations of plasmids and phage DNAs, such as plasmids that have been modified to employ phage DNA or other expression control sequences; baculovirus derivatives; and the like. For mammalian cells there are a number of well-known expression vectors available to the art.

Any of a wide variety of expression control sequences may be used in these vectors to express the DNA sequences of this invention. Such useful expression control sequences include, for example, the early and late promoters of SV40 or adenovirus for expression in mammalian cells, the lac system, the trp system, the tac or trc system, the major operator and promoter regions of phage λ, the control regions of fd coat protein, the promoter for 3-phosphoglycerate kinase of phosphatase (e.g., pho5), the promoters of the yeast α-mating factors, and other sequences known to control the expression of genes of prokaryotic or eukaryotic cells or their viruses, and various combinations thereof. The skilled artisan understands which expression control sequences are appropriate to particular vectors and host cells.

A wide variety of host cells are also useful in expressing the DNA sequences of this invention. These hosts may include well-known prokaryotic and eukaryotic hosts, such as strains of *E. coli, Pseudomonas, Bacillus, Streptomyces*, fungi such as yeasts, and animal cells, such as Chinese Hamster Ovary (CHO), R1.1, B-W and L-M cells, African Green Monkey kidney cells (e.g., COS 1, COS-7, BSC1, BSC40, and BMT10), insect cells (e.g., Sf9), and human cells and plant cells in culture.

It is understood that not all combinations of vector, expression control sequence and host cell will function equally well to express the DNA sequences of this invention. However, one skilled in the art will be able to select the proper vector, expression control sequence, and host cell combination without undue experimentation to accomplish the desired expression without departing from the scope of this invention.

In selecting a suitable expression control sequence, a variety of factors will normally be considered. These include, for example, the relative strength of the promoter, its controllability, and its compatibility with the particular DNA sequence or gene to be expressed, e.g., with regard to potential secondary structure. Suitable hosts will be selected by consideration of factors including compatibility with the chosen vector, secretion characteristics, ability to fold proteins correctly, and fermentation requirements, as well as any toxicity to the host of the product encoded by the DNA sequences to be expressed, and the ease of purification of the expression products. The practitioner will be able to select the appropriate host cells and expression mechanisms for a particular purpose.

Several strategies are available for the isolation and purification of recombinant PssZ after expression in a host system. One method involves expressing the proteins in bacterial cells, lysing the cells, and purifying the protein. Alternatively, one can engineer the DNA sequences for secretion from cells. An PssZ protein can be readily engineered to facilitate purification and/or immobilization to a solid support of choice. For example, a stretch of 6-8 histidines can be engineered through polymerase chain reaction or other recombinant DNA technology to allow purification of expressed recombinant protein over a nickel-charged nitrilotriacetic acid (NTA) column using commercially available materials. Other oligopeptide "tags" which can be fused to a protein of interest by such techniques include, without limitation, strep-tag (Sigma-Genosys, The Woodlands, Tex.), which directs binding to streptavidin or its derivative streptactin (Sigma-Genosys); a glutathione-S-transferase gene fusion system which directs binding to glutathione coupled to a solid support (Amersham Pharmacia Biotech, Uppsala, Sweden); a calmodulin-binding peptide fusion system which allows purification using a calmodulin resin (Stratagene, La Jolla, Calif.); a maltose binding protein fusion system allowing binding to an amylose resin (New England Biolabs, Beverly, Mass.); and an oligo-histidine fusion peptide system which allows purification using a $Ni^{2+}$-NTA column (Qiagen, Valencia, Calif.).

Hybridization conditions appropriate for detecting various extents of nucleotide sequence homology between probe and target sequences and theoretical and practical consideration are given, for example in B. D. Hames and S. J. Higgins (1985) Nucleic Acid Hybridization, IRL Press, Oxford, and in Sambrook et al. (1989). Under particular hybridization conditions the DNA sequences of this invention will hybridize to other DNA sequences having sufficient homology, including homologous sequences from different species. It is understood in the art that the stringency of hybridization conditions is a factor in the degree of homology required for hybridization. The skilled artisan knows how to manipulate the hybridization conditions so that the stringency of hybridization is at the desired level (high, medium, low). If attempts to identify and isolate the PssZ gene from another *Listeria* species or strain fail using high stringency conditions, the skilled artisan will understand how to decrease the stringency of the hybridization conditions so that a sequence with a lower degree of sequence homology will hybridize to the sequence used as a probe. The choice of the length and sequence of the probe is readily understood by the skilled artisan.

The DNA sequences of this invention refer to DNA sequences prepared or isolated using recombinant DNA techniques. These include cDNA sequences, sequences isolated using PCR, DNA sequences isolated from their native genome, and synthetic DNA sequences. As used herein, this term is not intended to encompass naturally-occurring chromosomes or genomes. These sequences can be used to direct recombinant synthesis of PssZ for enzymatic hydrolysis of EPS, especially from *L. monocytogenes.*

Isolated PssZ enzyme and/or polysaccharide is separated from the cells and culture medium from which it was produced. Further purification is optional and within the realm of the skilled artisan. The enzyme source can be a purified or partly purified enzyme or it can be present in a cell extract, recombinantly produced, or otherwise.

It is well-known in the biological arts that certain amino acid substitutions can be made within a protein without affecting the functioning of that protein. Preferably, such substitutions are of amino acids similar in size and/or charge properties. For example, Dayhoff et al. (1978) in Atlas of Protein Sequence and Structure, Volume 5, Supplement 3, Chapter 22, pages 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

It will be a matter of routine experimentation for the ordinary skilled artisan to use the DNA sequence information presented herein to optimize PssZ expression in a particular expression vector and cell line for a desired purpose. A cell line genetically engineered to contain and express an PssZ coding sequence is useful for the recombinant expression of protein products with the characteristic enzymatic activity of the specifically exemplified enzyme. Any means known to the art can be used to introduce an expressible PssZ coding sequence into a cell to produce a recombinant host cell, i.e., to genetically engineer such a recombinant host cell. Recombinant host cell lines which express high levels of PssZ are useful as sources for the purification of this enzyme.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gin, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, a DNA which has the sequence of part of a naturally occurring genomic DNA molecule but is not flanked by both of the coding or noncoding sequences that flank that part of the molecule in the genome of the organism in which it naturally occurs; a nucleic acid incorporated into a vector or into the genomic DNA of a prokaryote or eukaryote in a manner such that the resulting molecule is not identical to any naturally occurring vector or genomic DNA; a separate molecule such as a cDNA, a genomic fragment, a fragment produced by polymerase chain reaction (PCR), or a restriction fragment; and a recombinant nucleotide sequence that is part of a hybrid gene, i.e., a gene encoding a fusion protein. Specifically excluded from this definition are nucleic acids present in mixtures of DNA molecules, transformed or transfected cells, and cell clones, e.g., as these occur in a DNA library such as a cDNA or genomic DNA library.

In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer molecule is present in the medium in or on which the organism is cultivated.

One DNA portion or sequence is downstream of a second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a PssZ-encoding polynucleotide which is substantially separated from other polynucleotide sequences which naturally accompany it in the *L. monocytogenes* genome. The term embraces a polynucleotide sequence which has been removed from its naturally occurring environment, and includes recombinant or cloned DNA isolates, chemically synthesized analogs, and analogs biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other PssZ coding sequences, for example, those from others strains of *L. monocytogenes*. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction, or with fluors or other detectable moieties.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially cultured mammalian cells, wherein protein expression is desired. Usually, the construct is suitable for replication in a host cell, such as cultured mammalian cell or a bacterium, but a multicellular eukaryotic host may also be appropriate, with or without integration within the genome of the host cell. Commonly used prokaryotic hosts include strains of *Escherichia coli*, although other prokaryotes, such as *Bacillus subtilis* or a pseudomonad, may also be used. Eukaryotic host cells include mammalian cells, yeast, filamentous fungi, plant, insect, amphibian, and avian cell lines. Such factors as ease of manipulation, ability to appropriately glycosylate expressed proteins, degree and control of recombinant protein expression, ease of purification of expressed proteins away from cellular contaminants, or other factors that influence the choice of the host cell.

Example V

This Example describes materials and methods useful in degrading biofilms and controlling pathogenic bacteria. Described are uses of a produced *Listeria monocytogenes* PssZ protein, homolog, variant, or fragment, in preventing bacterial exopolysaccharide-dependent aggregation, in degrading a biofilm, and in inhibiting biofilm formation on a surface.

Bacterial biofilms are predominantly composed of a polysaccharide matrix which may further incorporate proteins, organic and mineral residues, and environmental particulates. An example of steps of forming a biofilm are as follows. A substratum surface is in contact with a liquid and the surface may be preconditioned by ambient molecules. Cells come in contact with the surface and some are adsorbed. A plurality of cells attach to the substratum surface and produce exopolysaccharides and quorum sensing may occur with concomitant changes in. Nutrients and oxygen diffuse into the biofilm matrix. Cells in the matrix replicate and grow. The cells continue to produce exopolysaccharides. As the biofilm grows, fragments may detach and be sloughed. The fragments carrying cells embedded in the matrix may be carried in the liquid to a new location to form a biofilm on another surface.

To control contamination and combat biofilms in food production, such as in the dairy industry, cleaning-in-place (CIP) procedures are usually employed in equipment for processing lines. The basic sequence of operations is: 1. a pre-rinse with cold water to remove gross residues; 2. a circulation of detergent to remove remaining minor residues; 3. an intermediate cold water rinse to flush out detergent; 4. a circulation of disinfectant to inactivate and kill any residual microorganisms; 5. a final cold water rinse to flush out detergent. The steps may include elevated temperatures and acidic or caustic solutions, for example: water rinse, 1% sodium hydroxide at 70 C for 10 min, water rinse, 0.8% nitric acid at 70° C. for 10 min, water rinse, followed by exposure to chlorine or combinations of nisin, lauricidin, and lactoperoxidase.

Addition of the PssZ enzyme at one or more rinse or detergent steps aids in degrading or digesting biofilms to make the biofilms more susceptible to cleaning and sanitizing agents. In an embodiment, a cleaning process comprises PssZ application followed by, or used in conjunction with, one or more of: water, hydrogen peroxide, alcohol, iodophor, quaternary ammonia compounds, chlorine solutions, peracetic acid, peroctanoic acid, nitric acid, benzoic acid, sodium hydroxide, dimethyl benzyl lauryl ammonium bromide, cationic surfactants, anionic surfactants, non-ionic surfactants, zwitterionic surfactants, nisin, lauricidin, lactoperoxidase, ampicillin, vancomycin, ciprofloxacin, azithromycin, or a proteolytic enzyme.

In an embodiment, the PssZ enzyme has at least 90 percent identity to *Listeria monocytogenes* PssZ [SEQ ID NO 1] or 90 percent identity to the *L. monocytogenes* PssZ protein lacking the transmembrane domain [SEQ ID NO 2]. In an embodiment, the PssZ enzyme has at least 90 percent identity to a PssZ homolog derived from at least one extremophile described in Example III [SEQ ID NOs 47, 50, 53, 56, 59]. In other embodiments, the PssZ enzyme has at least 80% identity to *L. monocytogenes* PssZ [SEQ ID NO 1], *L. monocytogenes* PssZ protein lacking the transmembrane domain [SEQ ID NO 2], or a PssZ homolog derived from at least one extremophile described in Example III. In other embodiments, the PssZ enzyme has at least 70% identity to *L. monocytogenes* PssZ [SEQ ID NO 1], *L. monocytogenes* PssZ protein lacking the transmembrane domain [SEQ ID NO 3], or a PssZ homolog derived from at least one extremophile described in Example III. In other embodiments, the PssZ enzyme has at least 60% identity to *L. monocytogenes* PssZ [SEQ ID NO 1], *L. monocytogenes* PssZ protein lacking the transmembrane domain [SEQ ID NO 2], or a PssZ homolog derived from at least one extremophile described in Example III. In other embodiments, the PssZ enzyme is a PssZ homolog, or fragment thereof, identified using BLAST alignment to a known PssZ sequence.

In an embodiment, the temperature of a PssZ solution is maintained at a temperature ranging from about 0° C. to about 65° C. In an embodiment, the pH of a PssZ solution ranges from about 4.0 to about 10.0. In an embodiment, the concentration of a PssZ enzyme in a PssZ solution ranges from about 0.1 nM to about 500 mM, or from about 1 nM to about 100 mM, or from about 0.1 mM to about 50 mM. In an embodiment of a method of cleaning, a PssZ contact time with a surface to be cleaned ranges from about 5 seconds to about 1 hour, or from about 30 seconds to about 30 minutes, or from about 60 minute to about 2 days.

In an embodiment of the invention, a PssZ application is used to prevent, degrade, or mitigate biofilms on equipment or in a facility. In an embodiment, the equipment is selected from: conveyors, slicers, peelers, sorters, packaging equipment, milking equipment, vats, tanks, condensing units, drip pans, utensils, sponges, and cleaning brushes. In an embodiment, facility application of PssZ is made to one or more of: floors, walls, ceilings, sink drains, tables, countertops, food contact surfaces, air filters, boot baths, floor trenches, and floor drains.

In some embodiments, the PssZ enzyme is stabilized. In some embodiments, a stabilized enzyme solution or compound comprises boric acid, propylene glycol, phenylboronic acid, glycerol. In some embodiments, the PssZ enzyme is stabilized by adsorbtion, covalent binding, crosslinking, entrapment, reversed micelleation, chemical modification, lyophilization, protein engineering, propanol rinsed preparation, ionic liquid coating, or stabilizing additives.

In an embodiment, a purified PssZ enzyme is applied directly to a food product. Listeriosis is of particular concern in ready-to-eat refrigerated foods because *L. monocytogenes* can grow at cool temperatures. An example for application includes rinsing or soaking food products, such as leafy greens, melons, or fresh cheeses in an aqueous solution containing PssZ. In another example, the foods are sprayed with a solution or aerosol containing purified PssZ. In another example, PssZ is incorporated into a food wax, emulsifier, sausage casing, waxed carton, or packaging. PssZ may be consumed by humans or animals with no anticipated adverse impact.

In an embodiment, a purified PssZ enzyme is applied directly to animal silage. In an embodiment, the application is performed prior to long-term storage of the silage.

In an embodiment, a non-pathogenic *Listeria* species is engineered to express the PssZ enzyme. *Listeria* species selected may include: *L. fleischmannii, L. grayi, L. innocua, L. marthii, L. rocourtiae, L. seeligeri, L. weihenstephanensis*, or *L. welshimeri*. In an embodiment, the produced enzyme is harvested. In another embodiment, the engineered *Listeria* sp. is inoculated into a system where it competes with the pathogenic *L. monocytogenes* and/or *L. ivanovii* and aids in the degradation of biofilms.

It is understood that even though the E72Q mutant is less catalytically active than certain other PssZ proteins, fragments, or variants, the E72Q mutant can nonetheless be used in any of the embodiments described herein.

Example VI

This Example describes uses of a polysaccharide having the composition of a trisaccharide repeating unit of {4)-β-ManpNAc-(1-4)-[α-Galp-(1-6)]-β-ManpNAc-(1-}, wherein ManpNAc is N-acetylmannosamine and Galp is galactose. The resistance of the listerial polysaccharide to desiccation and chemical degradation is evident from the persistent challenges in controlling listerial contamination. These same characteristics, in conjunction with the disclosed methods for degrading the polysaccharide, provide opportunities for controlled utilization of a polysaccharide matrix.

The present disclosure, providing the structure of the polysaccharide, further provides an edible compound. In an embodiment, the polysaccharide is used as an encapsulating compound for transporting particulates or probiotics to the intestine. In another embodiment, the polysaccharide is used as a food additive or filler. As one non-limiting example, the polysaccharide can be used in ice cream or other emulsion to prevent the product from developing frost crystals.

Example VII

Embodiments of the present disclosure can be formulated as part of a kit or kits. A non-limiting example of such a kit is a kit for ameliorating a bacterial contamination, which includes a PssZ enzyme solution and a disinfectant solution in separate containers, where the containers may or may not be present in a combined configuration. Many other kits are possible. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of hydrolyzing a listerial exopolysaccharide, the method comprising:
   contacting the listerial exopolysaccharide with a sufficient amount of a PssZ enzyme, wherein the PssZ enzyme has functional activity to hydrolyze a ManNAc-Gal exopolysaccharide, comprising a trisaccharide repeating unit of {4)-β-ManpNAc-(1-4)-[α-Galp-(1-6)]-β-ManpNAc-(1-}, wherein ManpNAc is N-acetylmannosamine and Galp is galactose; and
   hydrolyzing the listerial exopolysaccharide.

2. The method of claim 1, wherein the PssZ enzyme has at least 80% amino acid sequence identity to SEQ. ID NO: 2.

3. The method of claim 1, wherein the method further comprises treating a food container, a food equipment surface, a surface in a food production facility, a food product, or animal silage, with the PssZ enzyme.

4. The method of claim 1, further comprising:
   applying a sufficient amount of the PssZ enzyme to a bacterial aggregate, wherein the bacterial aggregate comprises at least one bacterial species from the Listeria genus, and disintegrating the bacterial aggregate.

5. A method of degrading a biofilm on a surface, wherein the biofilm comprises a listerial exopolysaccharide, the method comprising:
   identifying a PssZ homolog using BLAST alignment to a known PssZ sequence;
   producing the PssZ homolog, or a variant thereof, to form a produced PssZ substance;
   testing the produced PssZ substance for listerial exopolysaccharide-specific glycosyl-hydrolase activity; and
   applying the produced PssZ substance having listerial exopolysaccharide-specific glycosyl-hydrolase activity to the surface, thereby degrading the biofilm.

6. The method of claim 5, wherein the listerial exopolysaccharide comprises: a polysaccharide having the composition of a trisaccharide repeating unit of {14)-β-ManpNAc-(1-4)-[α-Galp-(1-6)]-β-ManpNAc-(1-}, wherein ManpNAc is N-acetylmannosamine and Galp is galactose.

7. The method of claim 5, wherein the known PssZ sequence is a PssZ sequence from a species in the Listeria genus.

8. The method of claim 5, wherein the known PssZ sequence is a sequence selected from the set consisting of: SEQ ID NO: 2, SEQ ID NO: 47, SEQ ID NO: 50, SEQ ID NO: 53, SEQ ID NO: 56, SEQ ID NO: 59, and SEQ ID NO: 64.

9. The method of claim 5, wherein the surface comprises: a food container surface, a food equipment surface, a food article surface, animal silage, or a surface in a food production facility.

10. A method of degrading a biofilm on a surface, wherein the biofilm comprises a listerial exopolysaccharide, the method comprising:
    applying a composition to the surface, wherein the composition comprises a PssZ enzyme, wherein the PssZ enzyme is a glycosyl hydrolase having specific functional activity to hydrolyze a listerial exopolysaccharide comprising a trisaccharide repeating unit of {4)-β-ManpNAc-(1-4)-[α-Galp-(1-6)]-β-ManpNAc-(1-}, wherein ManpNAc is N-acetylmannosamine and Galp is galactose.

11. The method of claim 10, wherein:
    the PssZ enzyme is an isolated PssZ enzyme produced from at least one of: a L. monocytogenes PssZ protein, a Listeria PssZ protein, a Listeria PssZ protein homolog, a Listeria PssZ protein variant, or a Listeria PssZ protein fragment, and
    the isolated PssZ enzyme has hydrolytic activity to hydrolyze the listerial exopolysaccharide.

12. The method of claim 10, further comprising:
    applying the composition in an amount sufficient to disperse a preformed listerial exopolysaccharide aggregate.

13. The method of claim 10, further comprising:
    contacting the surface with a detergent; and
    rinsing the surface with an aqueous solution.

14. The method of claim 10, further comprising:
    contacting the surface with a detergent after applying the composition; and
    rinsing the surface with an aqueous solution after contacting the surface with the detergent.

15. The method of claim 10, wherein
    the composition is applied to the surface in a solution; and
    the concentration of the PssZ enzyme in the solution ranges from about 0.1 nM to about 500mM.

16. The method of claim 10, wherein:
the composition is applied to the surface in a solution, and applying the composition to the surface further comprises contacting the solution to the surface for a period of time ranging from about 5 seconds to about 2 days.

17. The method of claim 10, further comprising:
contacting the surface with an antibacterial agent, wherein the antibacterial agent includes at least one agent selected from the group consisting of: sodium hypochlorite, hydrogen peroxide, an alcohol, an iodophor, a quaternary ammonia compound, a chlorine solution, a peracetic acid, a peroctanoic acid, a nitric acid, a benzoic acid, sodium hydroxide, dimethyl benzyl lauryl ammonium bromide, a cationic surfactant, an anionic surfactant, a non-ionic surfactant, a zwitterionic surfactant, nisin, lauricidin, lactoperoxidase, ampicillin, vancomycin, ciprofloxacin, azithromycin, or a proteolytic enzyme.

18. The method of claim 10, wherein the surface comprises: a food container surface, a food equipment surface, a food article surface, animal silage, or a surface in a food production facility.

* * * * *

UNITED STATES PATENT AND TRADEMARK OFFICE
CERTIFICATE OF CORRECTION

PATENT NO. : 10,383,338 B2
APPLICATION NO. : 15/522949
DATED : August 20, 2019
INVENTOR(S) : Mark Gomelsky, Kurt Miller and Volkan Köseoğlu Page 1 of 1

It is certified that error appears in the above-identified patent and that said Letters Patent is hereby corrected as shown below:

In the Claims

Column 99, Claim 6, Lines 60 - 61, correct:
"of a trisaccharide repeating unit of { 14)-β-ManpNAc-(1-4)-[α-Galp-(1-6)]-β-ManpNAc-(1-},"
To:
-- of a trisaccharide repeating unit of {4)-β-Man*p*NAc-(1-4)-[α-Gal*p*-(1-6)]-β-Man*p*NAc-(1-}, --.

Signed and Sealed this
Tenth Day of December, 2019

Andrei Iancu
*Director of the United States Patent and Trademark Office*